US012605413B2

(12) United States Patent
Kotagiri et al.

(10) Patent No.: US 12,605,413 B2
(45) Date of Patent: Apr. 21, 2026

(54) ENGINEERED PROBIOTICS FOR TREATMENT AND IMMUNITY AGAINST VIRUSES

(71) Applicant: University of Cincinnati, Cincinnati, OH (US)

(72) Inventors: Nalinikanth Kotagiri, West Chester, OH (US); Nitin S. Kamble, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 582 days.

(21) Appl. No.: 17/919,424

(22) PCT Filed: Apr. 19, 2021

(86) PCT No.: PCT/US2021/028027
§ 371 (c)(1),
(2) Date: Oct. 17, 2022

(87) PCT Pub. No.: WO2021/212122
PCT Pub. Date: Oct. 21, 2021

(65) Prior Publication Data
US 2025/0026812 A1     Jan. 23, 2025

Related U.S. Application Data

(60) Provisional application No. 63/011,446, filed on Apr. 17, 2020.

(51) Int. Cl.
| | |
|---|---|
| *A61K 35/741* | (2015.01) |
| *A61P 31/14* | (2006.01) |
| *C07K 16/104* | (2026.01) |
| *A61K 35/00* | (2006.01) |

(52) U.S. Cl.
CPC ............ *A61K 35/741* (2013.01); *A61P 31/14* (2018.01); *C07K 16/104* (2026.01); *A61K 2035/115* (2013.01); *C07K 2317/569* (2013.01)

(58) Field of Classification Search
CPC .......... C07K 2317/569; C07K 16/1003; A61K 2035/115; A61K 35/741; A61P 31/14
See application file for complete search history.

(56) References Cited

U.S. PATENT DOCUMENTS

| | | | |
|---|---|---|---|
| 2016/0264647 A1* | 9/2016 | Dimitrov ................. | C12N 7/00 |
| 2019/0202931 A1 | 7/2019 | Chen et al. | |
| 2019/0336544 A1 | 11/2019 | Falb et al. | |
| 2023/0183295 A1* | 6/2023 | Gao ....................... | A61K 39/12 424/186.1 |

FOREIGN PATENT DOCUMENTS

| | | |
|---|---|---|
| WO | 0234906 A2 | 5/2002 |
| WO | 2018045184 A1 | 3/2018 |

OTHER PUBLICATIONS

Hanke, Leo, et al. "An alpaca nanobody neutralizes SARS-CoV-2 by blocking receptor interaction." Nature communications 11.1 (2020): 4420. (Year: 2020).*
Tang. Application Progress of the Single Domain Antibody in Medicine. Int J Mol Sci. Feb. 20, 2023;24(4):4176. doi: 10.3390/ijms24044176. PMID: 36835588; PMCID: PMC9967291). (Year: 2023).*
Hanke, L. et al. "An alpaca nanobody neutralizes SARS-CoV-2 by blocking receptor interaction" Nature Communications, Sep. 4, 2020, pp. 1-9, vol. 11, DOI: https://doi.org/10.1038/s41467-020-18174-5.
Ho, M. "Perspectives on the development of neutralizing antibodies against SARS-CoV-2" Antibody Therapeutics, May 20, 2020, pp. 109-114, vol. 3, No. 2, DOI: 10.1093/abt/tbaa009.
Huang, C. et al. "Clinical features of patients infected with 2019 novel coronavirus in Wuhan, China" The Lancet, Jan. 24, 2020, pp. 497-506, vol. 395, DOI: https://doi.org/10.1016/S0140-6736(20)30183-5.
Zhang, Y. et al. "Wuhan seafood market pneumonia virus isolate Wuhan-Hu-1, complete genome" Database EMBL [Online] EBI, Jan. 13, 2020, pp. 1-16, Database accession No. MN908947.
EP Extended European Search Report dated May 28, 2024 pertaining to EP application No. 21788410.5 filed Oct. 17, 2022, pp. 1-8.
International Search Report mailed Oct. 12, 2021 in reference to co-pending PCT/US2021/028027 filed Apr. 19, 2021. 13 pgs.
Zhang, W. et al. Molecular and serological investigation of 2019-nCoV infected patients: implication of multiple shedding routes. Emerg Microbes Infect 9, 386-389 (2020).
Chen, Y., Guo, Y., Pan, Y. & Zhao, Z.J. Structure analysis of the receptor binding of 2019-nCoV. Biochem Biophys Res Commun (2020).
Vuille-Dit-Bille, R.N. et al. Human intestine luminal ACE2 and amino acid transporter expression increased by ACE-inhibitors. Amino Acids 47, 693-705 (2015).
Chen, P. et al. Dendritic cell targeted vaccines: Recent progresses and challenges. Hum Vaccin Immunother 12, 612-22 (2016).
Rescigno, M., Granucci, F., Citterio, S., Foti, M. & Ricciardi-Castagnoli, P. Coordinated events during bacteria-induced DC maturation. Immunol Today 20, 200-3 (1999).
Jones, H.E., Klein, N. & Dixon, G.L. Human dendritic cell culture and bacterial infection. Methods Mol Biol 799, 217-35 (2012).
Glass, D.S. & Riedel-Kruse, I.H. A Synthetic Bacterial Cell-Cell Adhesion Toolbox for Programming Multicellular Morphologies and Patterns. Cell 174, 649-658.e16 (2018).
Pinero-Lambea, C. et al. Programming controlled adhesion of E. coli to target surfaces, cells, and tumors with synthetic adhesins. ACS Synth Biol 4, 463-73 (2015).

(Continued)

*Primary Examiner* — Robert J Yamasaki
*Assistant Examiner* — Trevor Kane
(74) *Attorney, Agent, or Firm* — DINSMORE & SHOHL LLP

(57)     ABSTRACT

The present invention involves an engineered probiotic bacterium comprising a heterologous nucleic acid, where the heterologous nucleic acid comprises a nucleic acid sequence encoding an anti-spike glycoprotein nanobody of a coronavirus. In one embodiment, the bacterium is *Escherichia coli* Nissle 1917. In another embodiment, the anti-spike glycoprotein nanobody appears on the surface of the probiotic bacteria.

9 Claims, 15 Drawing Sheets

Specification includes a Sequence Listing.

(56)        References Cited

OTHER PUBLICATIONS

Jervis, A.J. et al. SelProm: A Queryable and Predictive Expression Vector Selection Tool for *Escherichia coli*. ACS Synthetic Biology 8, 1478-1483 (2019).

He, L. et al. Enhanced Ability of Oligomeric Nanobodies Targeting MERS Coronavirus Receptor-Binding Domain. Viruses 11(2019).

Zhao, G. et al. A Novel Nanobody Targeting Middle East Respiratory Syndrome Coronavirus (MERSCoV) Receptor-Binding Domain Has Potent Cross-Neutralizing Activity and Protective Efficacy against MERS-CoV. J Virol 92(2018).

Morgan, H. et al. Evaluation of in vitro Assays to Assess the Modulation of Dendritic Cells Functions by Therapeutic Antibodies and Aggregates. 10(2019).

Genbank Accession No. MH492377 .1, Cloning vector pDSG289, complete sequence, Jul. 6, 2018,Sep. 2018 [online]. [Retrieved on Sep. 13, 2021]. Retrieved from the internet: <URL: https://www. ncbi.nlm.nih.gov/nuccore/MH492377> Entire document.

\* cited by examiner cat promoter   J23105
                RBS

CmR lambda t0 terminator

-35
-10

Intimin pNKLab001_Intimin-TyNb
5875 bp

TEV site
Ty Nanobody
TEV site
FLAG
Strep-Tag II

T7Te terminator        rrnB T1 terminator pNKLab003-OmpA-TyNb
4336 bp pNKLab004_OmpA_VHH72 Codon-optimised
4363 bp

Nanobody ← OmpA 159 aa

Outer membrane

Periplasm

Lpp 1-9 aa ⟶

OmpA 46 aa ⟶

VHH72 Nanobody ⟶

D0 domain ⟶

D00 domain ⟶

Intimin

Exterior

Outer membrane

Periplasm

Ty1 Nanobody

D0 domain

D00 domain

Intimin

Exterior

Outer membrane

Membrane

Periplasm

VHH72 Nanobody

OmpA 159 aa

Outer membrane

Periplasm

Lpp 1-9 aa

OmpA 46 aa

Spike + Anti-S2 + Alexa Fluor ® 647

ENGINEERED PROBIOTICS FOR TREATMENT AND IMMUNITY AGAINST VIRUSES

CROSS REFERENCE TO RELATED APPLICATIONS

This application is a continuation of PCT Application No. PCT/US21/28027 filed Apr. 19, 2021, which claims benefit of U.S. Provisional Application Ser. No. 63/011,446, filed Apr. 17, 2020, which application is hereby incorporated by reference in its entirety.

SEQUENCE LISTING

A CRF sequence listing in ASCII format, having file name "2024-08-02_Sequence_Listing_ST25.txt" (51,486 bytes), created on Aug. 2, 2024, is incorporated herein by reference in its entirety.

TECHNICAL FIELD

The present invention relates to a novel engineered probiotic.

BACKGROUND OF THE INVENTION

The Covid-19 pandemic has revealed that the SARS-Cov-2 has multiple routes of transmission, including the fecal-oral route, as evidenced by persistent diarrhea, and shedding via feces. Structural analysis has revealed that the receptor binding domain (RBD) of the spike glycoprotein on SARS-Cov-2 interacts strongly with angiotensin converting enzyme 2 (ACE2). Besides lung, ACE2 is predominantly expressed in intestines, testis, and kidney. Therefore, strategies involving blocking the interaction of ACE2 with spike proteins might help in combating the virus. While such strategies that involve development of antibodies and small molecules could prove to be immensely beneficial in the short run as therapeutics, a more holistic approach is needed to both treat and provide long-lasting immunity against such viruses, such that recurrence is prevented and new transmissions effectively blocked.

SUMMARY OF THE INVENTION

The present invention involves an engineered probiotic bacterium comprising a heterologous nucleic acid, where the heterologous nucleic acid comprises a nucleic acid sequence encoding an anti-spike glycoprotein nanobody of a corona-virus. In one embodiment, the bacterium is *Escherichia coli* Nissle 1917. In another embodiment, the nucleic acid sequence is selected from the group consisting of SEQ ID NO: 1, SEQ ID NO: 2, SEQ ID NO: 3 and SEQ ID NO: 4. In another embodiment, the anti-spike glycoprotein nano-body appears on the surface of the probiotic bacteria.

In one embodiment, the heterologous nucleic acid is located in a plasmid. In another embodiment, the plasmid is selected from the group consisting of pNKLab001, pNKLab002, pNKLab003 and pNKLab004. In one embodiment, the plasmid further incorporates a surface display signal. In another embodiment, the surface display signal is selected from the group consisting of Intimin and Lpp-OmpA. In another embodiment, the plasmid has a sequence selected from the group consisting of SEQ ID NO: 5, SEQ ID NO: 6, SEQ ID NO: 7, SEQ ID NO: 8, SEQ ID NO: 9 and SEQ ID NO: 10.

In another embodiment, the present invention involves a plasmid that expresses one or more surface displayed nano-bodies where the one or more surface displayed nanobodies have a sequence selected from the group consisting of SEQ ID NO: 1, SEQ ID NO: 2, SEQ ID NO: 3 and SEQ ID NO: 4.

In one embodiment, the plasmid further incorporates a surface display signal. In another embodiment, the surface display signal is selected from the group consisting of Intimin and Lpp-OmpA. In one embodiment, the plasmid has a nucleic acid sequence selected from the group consisting of SEQ ID NO: 5, SEQ ID NO: 6, SEQ ID NO: 7, SEQ ID NO: 8, SEQ ID NO: 9 and SEQ ID NO: 10. In another embodiment, the plasmid is a CJ23 plasmid. In one embodiment, the plasmid has the nucleic acid sequence of SEQ ID NO: 11.

In one embodiment, the present invention involves a pharmaceutical composition including the engineered pro-biotic bacterium and a pharmaceutically acceptable excipi-ent. In another embodiment, the pharmaceutical composi-tion is formulated for oral administration to a subject. In one embodiment, the pharmaceutical composition is formulated for rectal administration to a subject. In another embodi-ment, the pharmaceutical composition is formulated as a pill, a capsule, a lozenge or a suppository.

In one embodiment, the present invention involves a method for preventing a disease or disorder in a subject. The method involves administering the engineered probiotic bacterium of the present invention to the subject, wherein the engineered probiotic bacterium expresses an anti-spike glycoprotein nanobody, thereby preventing the disease or disorder in the subject.

In another embodiment of the method, the engineered probiotic bacterium is administered orally. In one embodi-ment of the method, the engineered probiotic bacterium is administered rectally.

BRIEF DESCRIPTION OF THE DRAWINGS

The foregoing summary, as well as the following detailed description of preferred embodiments of the application, will be better understood when read in conjunction with the appended drawings.

DETAILED DESCRIPTION OF THE INVENTION

Figure 1:
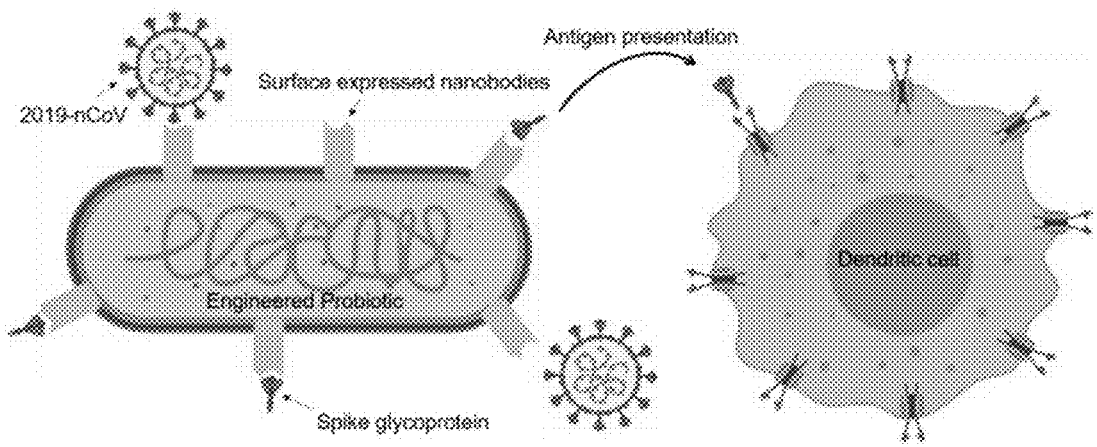
FIG. 1 is a schematic representation of an engineered probiotic (EP) with surface expressing nanobodies binding to virus and spike protein antigen and presenting to intestinal dendritic cells. Not drawn to scale.

The details of one or more embodiments of the disclosed subject matter are set forth in this document. Modifications to embodiments described in this document, and other embodiments, will be evident to those of ordinary skill in the art after a study of the information provided herein.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

The term "engineered", as used herein, refers to a nucleic acid molecule, protein molecule, complex, substance, or entity that has been artificially designed, produced, prepared, synthesized and/or manufactured. Therefore, the engineered product is a non-naturally occurring product.

As used herein, the term "engineered bacterium" or "engineered bacterial cell" refers to a bacterial cell that has been genetically modified from its native state. For instance, an engineered bacterial cell may have nucleotide insertions, nucleotide deletions, nucleotide rearrangements, and nucleotide modifications introduced into their DNA. These genetic modifications may be present in the chromosome of the bacteria or bacterial cell, or on a plasmid in the bacteria or bacterial cell. Engineered bacterial cells of the disclosure may comprise exogenous nucleotide sequences on plasmids. Alternatively, recombinant bacterial cells may comprise exogenous nucleotide sequences stably incorporated into their chromosome.

As used herein, a "heterologous" gene, "heterologous sequence", or "heterologous nucleic acid" refers to a nucleic acid sequence that is not normally found in a given cell in nature. As used herein, a heterologous sequence encompasses a nucleic acid sequence that is exogenously introduced into a given cell. "Heterologous gene" includes a native gene, or fragment thereof, that has been introduced into the host cell in a form that is different from the corresponding native gene. A heterologous gene may include a native gene, or fragment thereof, introduced into a non-native host cell. Thus, a heterologous gene may be foreign or native to the recipient cell; a nucleic acid sequence that is naturally found in a given cell but expresses an unnatural amount of the nucleic acid and/or the polypeptide which it encodes; and/or two or more nucleic acid sequences that are not found in the same relationship to each other in nature.

"Probiotic", as used herein, refers to a live, non-pathogenic microorganism, e.g., a bacterium, which can confer health benefits to a host organism. In some embodiments, the host organism is a mammal. In some embodiments, the host organism is a human. Some species, strains, and/or subtypes of non-pathogenic bacteria are currently recognized as probiotic bacteria. Examples of probiotic bacteria include, but are not limited to, *Salmonella typhimurium, Listeria monocytogenes, Staphylococcus epidermidis, Bifidobacterium, Bacteroides, Bacillus, Burkholderia cepacia, Propionibacterium, Fusobacterium, Campylobacter jejuni, Lactobacillus acidophilus, Klebsiella, Bacillus coagulans, Enterococcus* and *Streptococcus*, including *Streptococcus oralis*. The probiotic may be a variant or a mutant strain of bacterium. Non-pathogenic bacteria may be genetically engineered to enhance or improve desired biological properties, e.g., survivability.

A "pharmaceutical composition," as used herein, refers to a composition comprising an active ingredient (e.g., a bacterial cell, an inducer, a drug, or a detectable compound) with other components such as a physiologically suitable carrier and/or excipient.

As used herein, the term "pharmaceutically acceptable" or "pharmacologically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Moreover, for animal (e.g., human) administration, it will be understood that compositions should meet sterility, pyrogenicity, general safety and purity standards as required by the FDA Office of Biological Standards.

As used herein, the term "pharmaceutically acceptable excipient" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, disintegrating agents, binders, sweetening agents, flavoring agents, perfuming agents, protease inhibitors, plasticizers, emulsifiers, stabilizing agents, viscosity increasing agents, film forming agents, solubilizing agents, surfactants, preservative and antioxidants can also be present in the formulation. The terms such as "excipient", "carrier", "pharmaceutically acceptable excipient" or the like are used interchangeably herein.

As used herein, the term "nanobody" refers to any single variable domain of heavy immunoglobulin chains.

As used herein, the term "plasmid" refers to a construct composed of genetic material (i.e., nucleic acid).

As used herein, the term "surface display signal" refers to a genetic element that is programmed to be displayed on the bacterial cell surface, (e.g. flagella, pili, Intimin or Lpp-OmpA).

As used herein, the term "about," when referring to a value or to an amount of mass, weight, time, volume, pH, size, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

While the following terms are believed to be well understood by one of ordinary skill in the art, definitions are set forth to facilitate explanation of the disclosed subject matter. Unless defined otherwise, all technical and scientific terms used herein have the same meaning as commonly understood by one of ordinary skill in the art to which the disclosed subject matter belongs.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The human microbiota is a massive, mostly underexplored niche for short-term immunotherapy and long-term adaptive immunity against viruses. The present invention utilizes a probiotic, commensal bacteria (such as *Escherichia coli* Nissle 1917 (EcN)) that is already present in cosmic populations inside our gut and genetically-modifies it to give it the power of immunotherapy. Some of the ways by which natural probiotics confer protection to the gastrointestinal environment and immunity from pathogens are through: Direct antagonism, Competitive exclusion, Barrier function and Immune stimulation due their proximity to Dendritic cells (DCs). These intestinal DC, also known as Langerhans cells, are the among the first cells to encounter pathogens/viruses in the gastrointestinal tract and, upon activation, migrate to lymph nodes where they activate and educate T cells to initiate the immune response. Therefore, they are adequately positioned to interact with gut bacteria to absorb, process and present antigens, such as spike glycoproteins from invading virus. DCs are known to be the strongest functional professional antigen presenting cells (APCs), which can absorb, process and present antigens. As the key regulators of innate and adaptive immune responses, DCs are at the center of the immune system and capable of interacting with both B cells and T cells, thereby manipulating the humoral and cellular immune responses. Targeting antigens to DC-specific endocytic receptors has been recently recognized as a promising strategy for designing an effective vaccine that elicits a strong and durable T cell response against different types of pathogens. In fact, it was previously analyzed that DCs have the capacity of to interact with bacteria, and that bacteria can act as "Trojan horses", delivering heterologous proteins to DCs in a processed form that allows extremely efficient loading of both MHC class I and class II molecules. While commensal bacteria and natural probiotics have some capacity to relay antigens to DC, it is apparent that their capacity is limited because they lack the arsenal to capture and present the antigens effectively, and might not be able to limit the antigens and virus to the extracellular space, without losing viability. Moreover, in cases such as SARS-Cov-2, where lethality is severe, it appears natural defenses are overwhelmed leading to a cascade of reactions manifested in severe morbidity and mortality.

There is a need for new strategies that can provide protection against all subtypes of coronavirus, such as SARS, MERS, Covid-19. The EP platform of the present invention is modular in nature, able to integrate any nanobody as a plug-and-play system, allowing integration of unique nanobodies against distinct viruses and pathogens. The EP has a dual role in construct-therapy for infection by preventing virus and its surface proteins from binding to ACE2, and immune activation through DC antigen presentation and activation. They may be able to also neutralize future emergent coronaviruses before they can cause pandemics. Moreover, the ability of bacteria to proliferate at a rapid rate allows for an amplified response as treatment progresses and is entirely autonomous. As a result, the therapeutic response only increases over time without any external input or additional dosage.

Engineered Probiotic Bacteria

The present invention involves engineered probiotics (EP) capable of synthesizing multiple types of genetically-encoded therapeutic molecules, such as nanobodies. Probiotic bacteria of the present invention are engineered to express unique, coronavirus type-specific nanobodies, and display them on their surface (see FIG. 1) providing them the ability to actively and specifically bind to spike proteins and viruses and exhibit an effect similar to human monoclonal antibodies (mAbs). Besides directly preventing the virus and its antigens from interacting with ACE2 through competitive exclusion and direct antagonism, the EP-nanobody construct will also contribute to immune stimulation by effectively presenting the antigens to DCs for processing, loading and antigen presentation. This is all accomplished without potentially losing its own viability in the process.

An engineered probiotic (EP) with surface nanobodies serves a dual role of neutralizing initial toxicity from virus and its antigens, as well as providing long-term immunity by interfacing with intestinal DC by assisting in antigen absorption and presentation. In one embodiment, *E. coli* Nissle (EcN) is modified to express and display nanobodies on the surface. This is accomplished using EP that express antispike glycoprotein nanobodies on the surface of EcN. Non-limiting examples of other bacteria that can be used for the present invention include *Salmonella typhimurium, Listeria monocytogenes, Staphylococcus epidermidis, Bifidobacterium, Bacteroides, Bacillus, Burkholderia cepacia, Propionibacterium, Fusobacterium, Campylobacter jejuni, Lactobacillus acidophilus, Klebsiella, Bacillus coagulans, Enterococcus* and *Streptococcus*, including *Streptococcus oralis*.

Plasmids

Surface-bound antigen expression uses the bacterial chassis as an adjuvant to promote immune cell recognition and uptake. The present invention has developed a series of plasmids that constitutively express the surface displayed nanobodies with the help of surface display signals-Intimin and Lpp-OmpA. A plasmid with constitutive promoter CJ2310 accessed from BioBrick, was used as a backbone for the construction of all the pNKLab00 series of plasmids. Two different surface display signals (Intimin/Lpp-OmpA) were evaluated for displaying the COVID-19 nanobodies on the bacterial cell surface. The truncated version of Intimin (Part: BBa_K2332010) and Lpp-OmpA (Part: BBA_J36850) sequences were accessed from the Registry of Standard Biological Parts (iGEM). Intimin is an outer membrane protein and thus proteins fused to its N-termini are known to be displayed on the cell surface. While Lpp-OmpA protein is an outer membrane protein expression system, which consists of 20 amino acid (aa) of signal sequence, the 9 N-terminal amino acids of the lipoprotein (Lpp) and the residual 46-159 aa of the OmpA protein. The Lipoprotein (Lpp) is the most abundant protein on the outer membrane that possesses the function of targeting to the outer membrane, while OmpA domain constitutes 8-stranded, β-barrel to construct an anchor on the outer membrane that provides stable expression of the protein displayed on the outer membrane. By hijacking the efficient targeting OmpA to the outer membrane, it allows C-terminal fusion of the protein sequence to be displayed out of the outer membrane.

The DNA sequences for several plasmids that are useful in the present invention include SEQ ID NO: 5 (pNKLab001_Intimin-TyNb), SEQ ID NO: 6 (variation of pNKLab001-Intimin-TyNb), SEQ ID NO: 7 (pNKLab002_Intimin-VHH72), SEQ ID NO: 8 (pNKLab003_OmpA-TyNb), SEQ ID NO: 9 (pNKLab004_OmpA-VHH72Nb) and SEQ ID NO: 10 (variation of pNKLab004_OmpA-VHH72). In addition, The DNA sequence for a CJ23 plasmid is shown as SEQ ID NO: 11.

Nanobody

Figure 2:
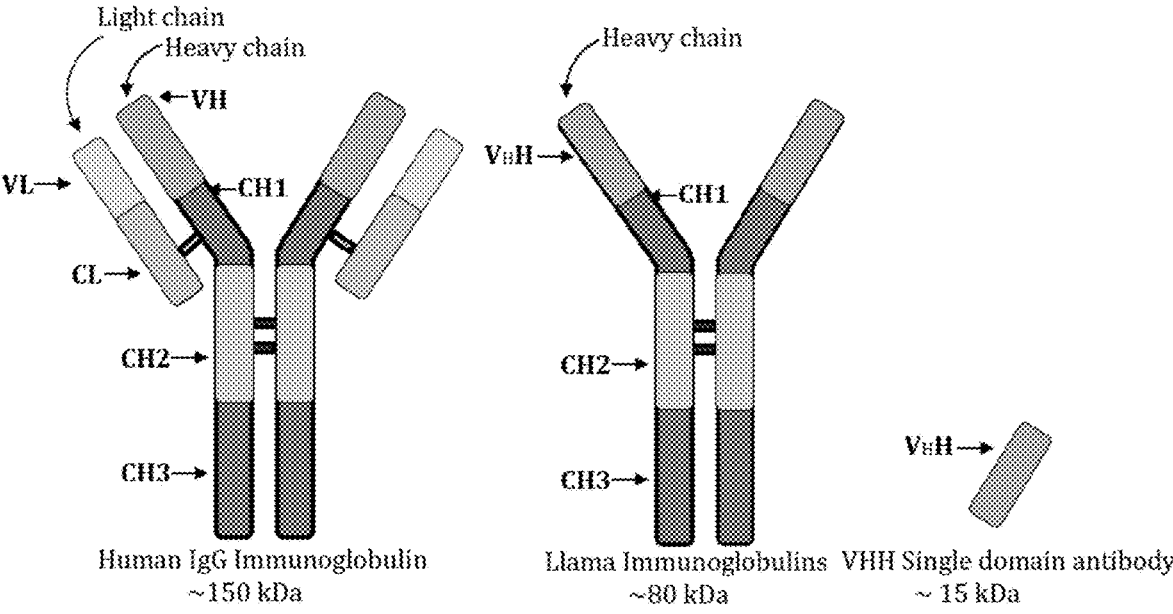
FIG. 2 is a schematic representation of Human IgG Immunoglobulin, Llama Immunoglobulins and a VHH Single domain antibody.

A typical antibody is ~150 kDa in size which has heavy and light chains covalently joined with Sulphur-Sulphur (S—S) bridges, as shown (FIG. 2). A new class of antibodies found in Llama has only heavy chains bonded with S—S bonds and are ~80 kDa in size. However, recently single domain antibodies have been discovered called Nanobodies, which are 10 times smaller than a typical antibody that weighs ~15-18 kDa.

VHH72 and Ty1 nanobody amino acids sequences reported against SARS Cov2 spike protein were accessed. The nanobody sequences were generated de novo utilizing a gene synthesis technology with the flanking BioBrick prefixes/suffixes, codon optimized using Online tools offered by GeneArt Synthesis (Thermo Scientific) and IDT. These gene blocks for Intimin, Lpp-OmpA surface display signals and the COVID19 nanobodies were assembled using Chloramphenicol resistant CJ23 plasmid in order to generate the pNKLab001-pNKLab004 constructs shown in FIGS. 4A, 5A, 6A and 7A.

The DNA sequences for several nanobodies that are useful in the present invention include SEQ ID NO: 1 (VHH72 Nanobody), SEQ ID NO: 2 (variation of a VHH72 Nanobody), SEQ ID NO: 3 (Ty Nanobody) and SEQ ID NO: 4 (variation of a Ty Nanobody).

The engineered probiotic bacteria with surface displayed nanobodies of the present invention serve the dual function of neutralizing initial events in toxicity due to viruses and its antigen, and also provide long-term immunity by means of interacting with intestinal DC by assisting in the antigen absorption and presentation.

As shown in the examples below, the present invention has shown successful expression of the both Ty1 and VHH72 nanobody using both Lpp-Omp and Intimin surface display signals. In addition, pNKLab003 has higher expression of nanobody (Ty1) not only in cell fraction but also in supernatant. Hence, the data shows that the present invention has successfully expressed both the COVID-19 nanobodies on the surface of *E. coli* Nissle.

EXAMPLES

Example 1

Figure 3:
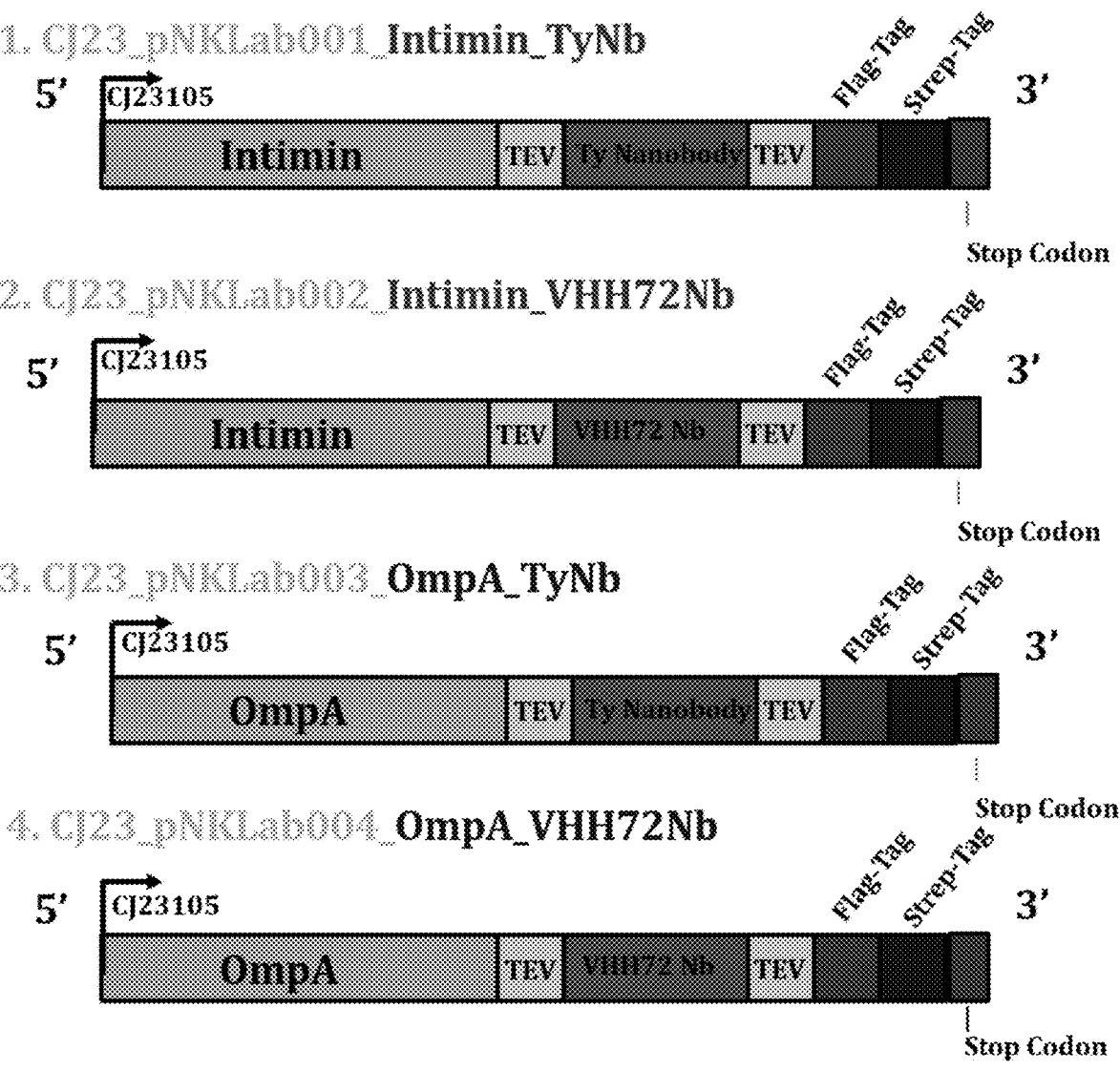
FIG. 3 is a series of linear maps for four constructs of different combinations of the nanobodies Ty1 and VHH72 fused with surface display signals Intimin and Lpp-OmpA.
Figures 4A, 4B:
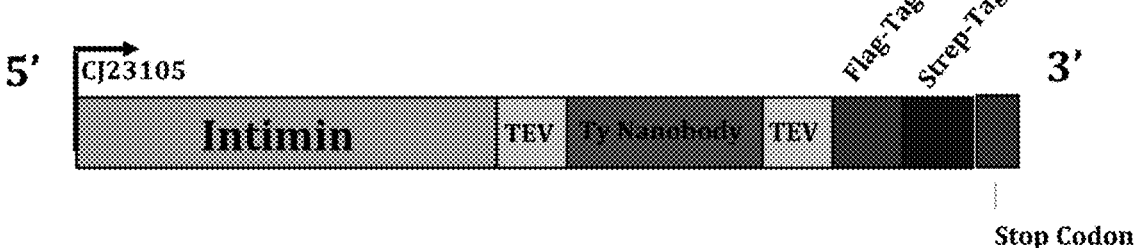
FIG. 4A is a circular map of pNKLab001-Intimin-Ty1Nb-Flag/Strep-Tag.
FIG. 4B is a linear map of pNKLab001-Intimin-Ty1Nb-Flag/Strep-Tag.
Figure 5A:
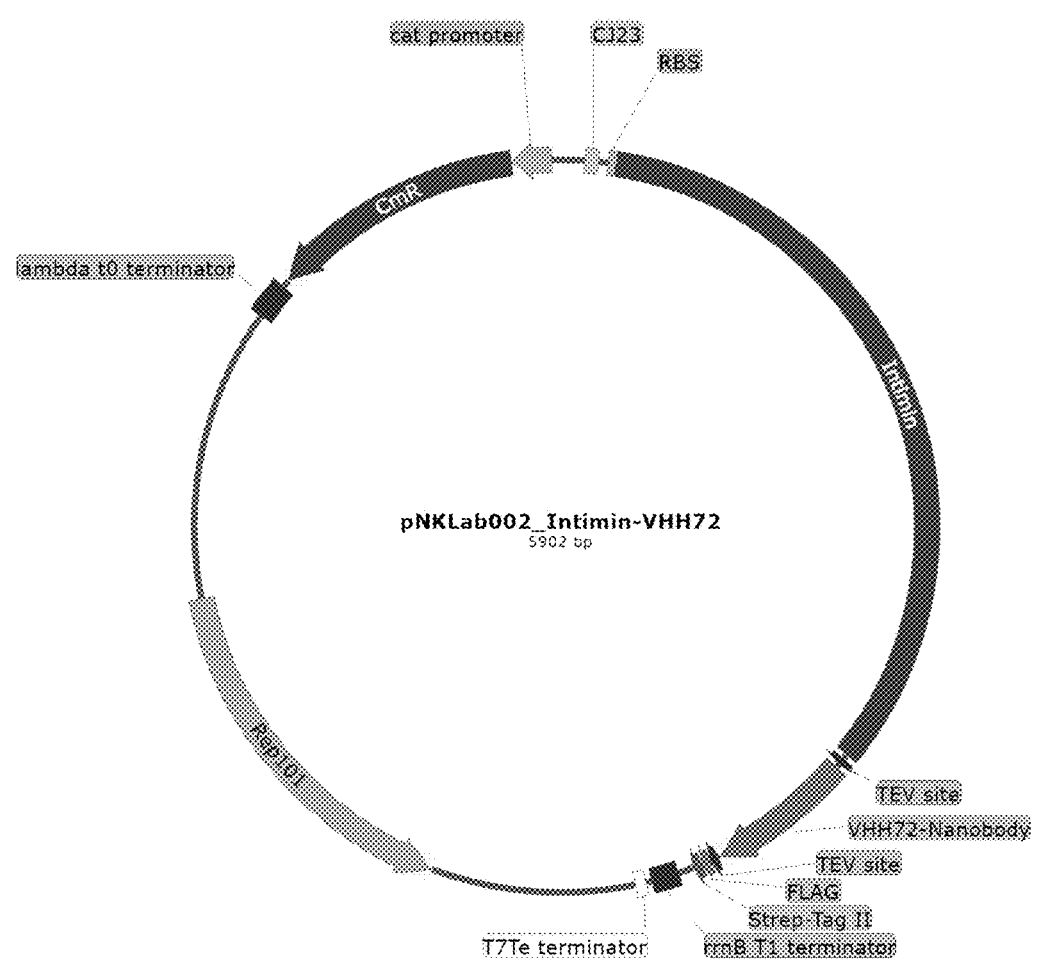
FIG. 5A is a circular map of pNKLab002-Intimin-VHH72Nb-Flag/Strep-Tag.
Figure 5B:
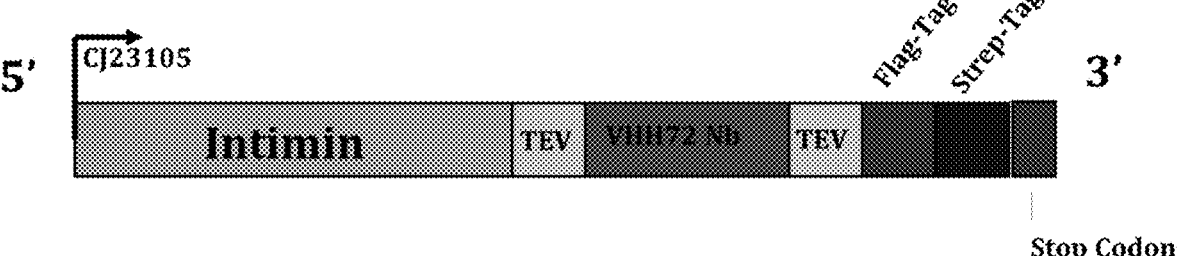
FIG. 5B is a linear map of pNKLab002-Intimin-VHH72Nb-Flag/Strep-Tag.
Figure 6A:
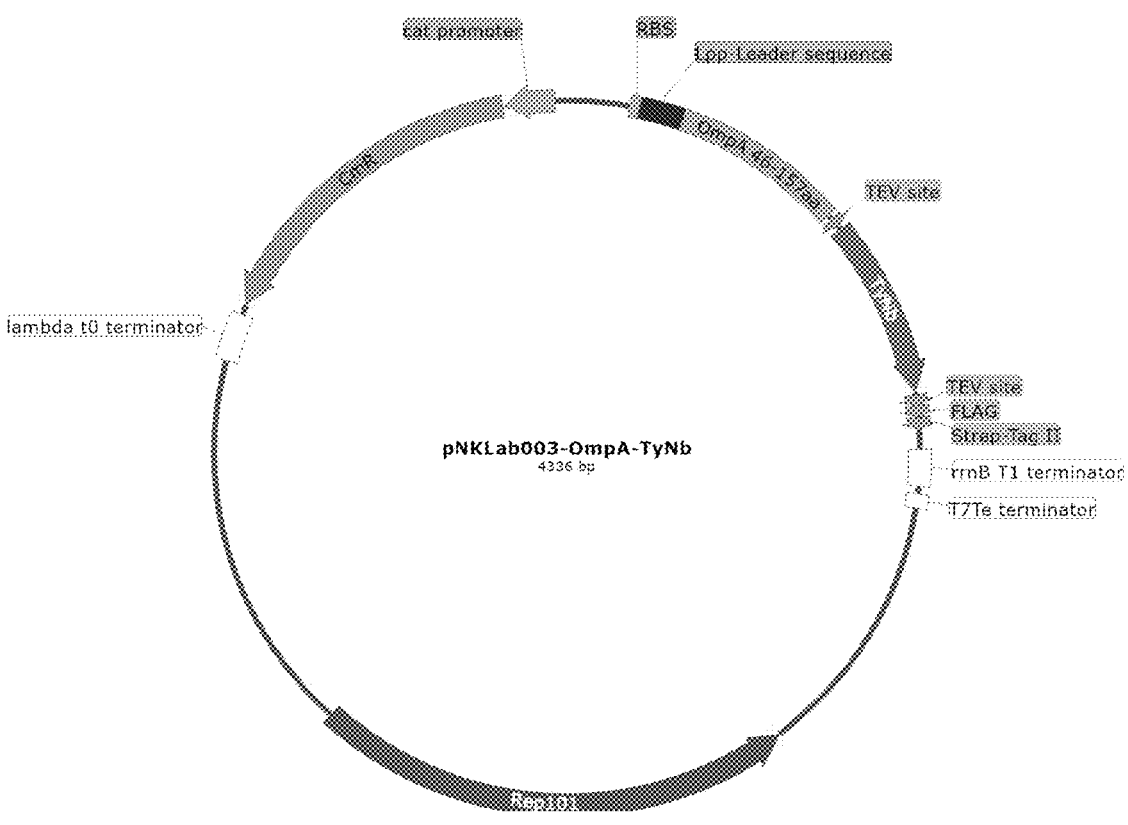
FIG. 6A is a circular map of pNKLab003-Lpp-OmpA-Ty1Nb-Flag/Strep-Tag.
Figure 6B:
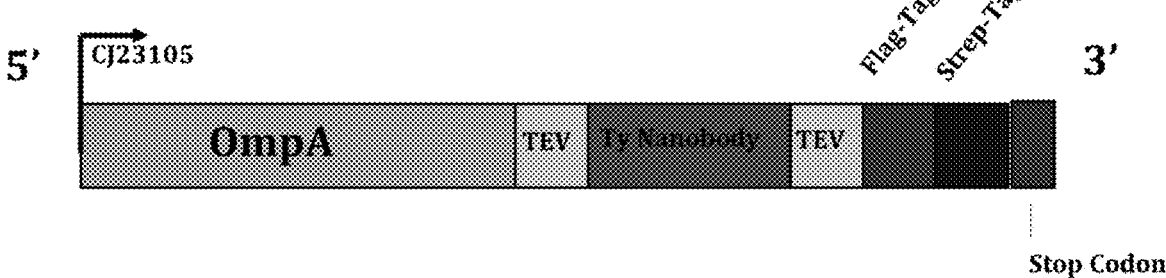
FIG. 6B is a linear map of pNKLab003-Lpp-OmpA-Ty1Nb-Flag/Strep-Tag.
Figure 7A:
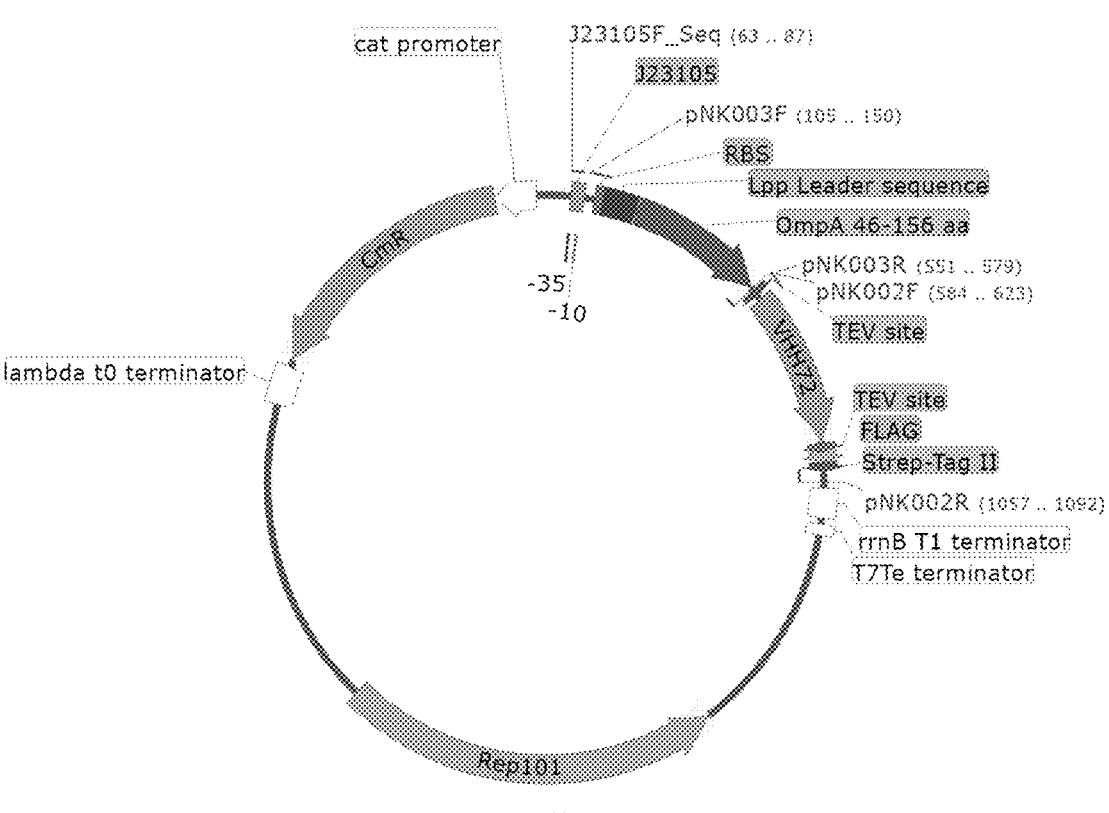
FIG. 7A is a circular map of pNKLab004-Lpp-OmpA-VHH72Nb-Flag/Strep-Tag.
Figure 7B:
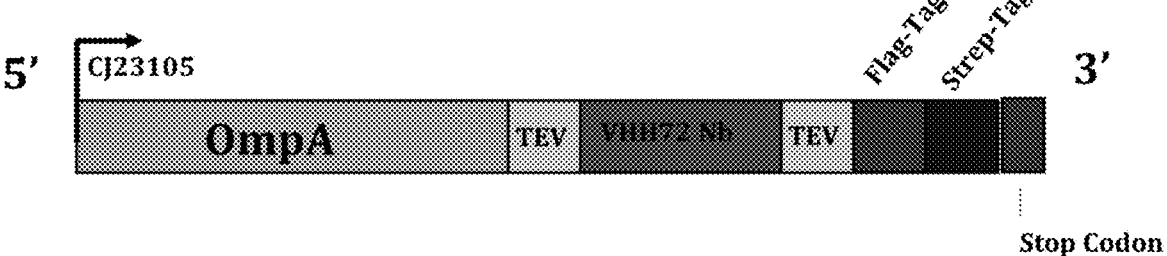
FIG. 7B is a linear map of pNKLab004-Lpp-OmpA-VHH72Nb-Flag/Strep-Tag.
Figure 8:
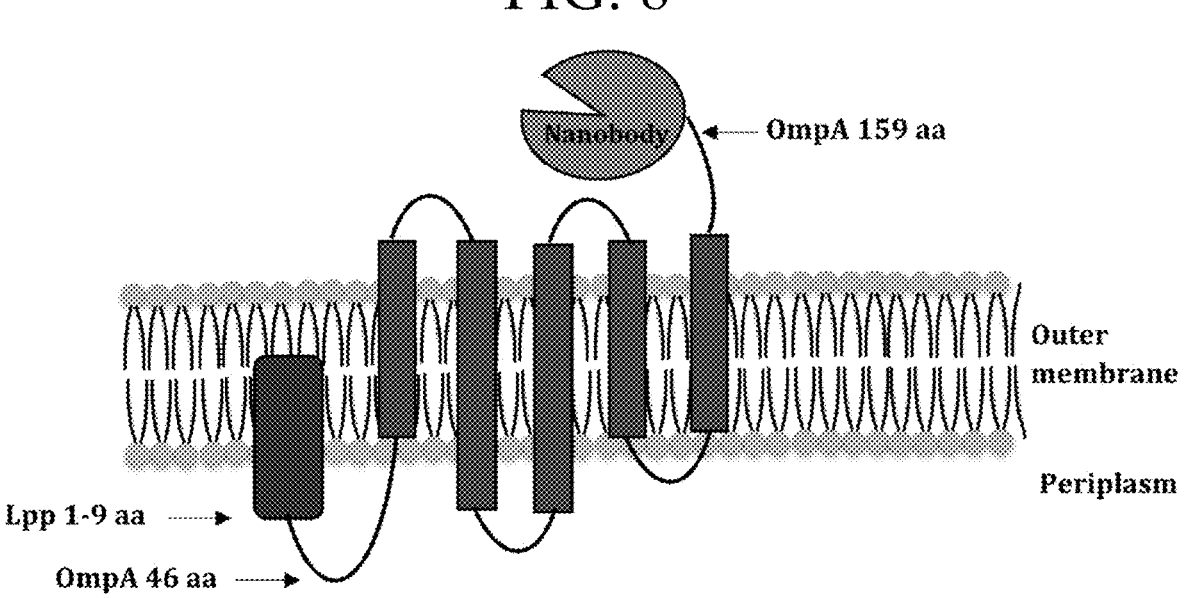
FIG. 8 is an illustration of a nanobody displayed on surface of engineered probiotic.

The design, construction and cloning of pNKLab001-4 plasmids for nanobody expression using surface display signals Intimin and Lpp-OmpA in *E. coli* Nissle is described. For the molecular cloning of COVID Nanobodies VHH72 and Ty1, Chloramphenicol resistant CJ23 plasmid was utilized, as it contains a constitutive promoter CJ23105. Both the Nanobodies, Ty1 and VHH72 were fused with surface display signals Intimin and Lpp-OmpA in order to generate four constructs (See FIG. 3). The Intimin gene sequence is about 2.0 kb corresponding to ~72 kDa peptide. In order to test and avoid the possibility of large peptide burying the smaller nanobody (13-15 kDa), a shorter surface display signal-Lpp-OmpA of 478 bp, corresponding to ~15.394 kDa peptide was used. All the constructs were incorporated with Flag tag and Strep tag for the detection and purification purposes. Finally, Tobacco Etch virus (TEV) cleavage sites were incorporated in-between surface display signal and the nanobody for detaching the display signal peptide from that of the nanobody.

Example 2

For the construction of pNKLab001-Intimin-Ty1Nb Nanobody, a gene block was ordered from a GeneArtSynthesis (Thermo Scientific). It was received lyophilized in 5 μg Kanamycin resistant plasmid pMK-RQ. Upon arrival, it was re-suspended in 50 μL of 1×TAE buffer and chemically transformed into DH5α competent cells (NEB) and spread on LB-kanamycin plates. Following 24 hr incubation at 37° C., positive clones were selected and grown in 3 ml cultures overnight, in order to extract the pKM-RQ plasmid. pKM-RQ and CJ23 plasmids were digested overnight using EcoRI and PspXI and BglII-PspXI restriction enzymes.

The insert released following restrict digest of pKA-RQ was cloned into similarly digested CJ23 plasmid and were ligated overnight at 16° C. 3.5 μL of ligation mixtures was chemically transformed into DH5α competent cells (NEB) and spread on chloramphenicol selection plates. Plates were incubated at 37° C. overnight. About 40-colonies were randomly screened for successful cloning by using colony PCR.

Following Colony PCR, 5 colonies were selected and grew overnight in 3 ml using Chloramphenicol at 37° C. Plasmids were extracted from these 5-colonies using Clone-Jet plasmid extraction kit (Thermo Scientific) and sent for Sanger sequencing. Sequencing results were verified for mutations manually or by using software tools such as SnapGene and/or Multalign.

Example 3

High Fidelity PCR amplification for VHH72 Nanobody is described. For the construction of pNKLab002-Intimin-VHH72 Nanobody, the VHH72-Nanobody fused with Flag/Strep tag was amplified by using pNKLab004 plasmid as a template. pNKLab004 plasmid contains, sequentially Lpp-OmpA-VHH72-Flag/Strep. pNKLab004-Lpp-OmpA-VHH72 was constructed prior to this pNKLab002 construct, for which gene block was ordered, as previously, from GeneArtSynthesis (Thermo Scientific).

Amplified PCR product for VHH72-strep/Flag was digested along with CJ23 plasmid by using HindIII- and PspXI restriction enzymes, for placing the VHH72-Flag/strep gene sequence downstream of Intimin in the CJ23 plasmid. This produced the newly constructed plasmid named-pNKLab002-Intimin-VHH72Nb-Flag/strep. Following restrict digest, digest reactions were run on 1% Agarose gel. These were gel extracted, cleaned and ligated overnight.

Following overnight Ligation, 3.5 μL of ligation mixtures was chemically transformed into DH5α competent cells (NEB) and spread on chloramphenicol selection plates. Plates were incubated at 37° C. overnight. About 40-colonies were randomly screened for successful cloning by performing colony PCR on the selected colonies.

Example 4

Preliminary confirmation with Colony PCR. Following colony PCR, 6 colonies were selected and grew overnight in 3 ml using Chloramphenicol at 37° C. Plasmids were extracted from these 6-colonies using CloneJet plasmid extraction kit (Thermo Scientific) and sent for Sanger sequencing. Sequencing results were verified for mutations manually or by using software tools such as SnapGene and/or Multalign and NCBI.

Example 5

In order to construct a pNKLab003-Lpp-OmpA-TyNb-Flag/Strep-Tag plasmid, previously constructed pNKLab001-Intimin-Ty1Nb-Flag/Strep-Tag plasmid was used as it contains the Ty1 Nanobody attached with Intimin. The Intimin was replaced by Lpp-OmpA signal, resulting in a pNKLab003-Lpp-OmpA-TyNb-Flag/Strep-Tag plasmid. A Lpp-OmpA signal of about ~497 bp was PCR amplified by using pNKLab004-Lpp-OmpA-VHH72Nb-Flag/Strep-Tag as a template for PCR amplifications (since it contains the Lpp-OmpA signal). PCR was run on 1% agarose gel.

Example 6

High Fidelity PCR was used to amplify the Lpp-OmpA signal for cloning to pNKLab001 plasmid. The PCR was cleaned and digested along with pNKLab001-Intimin-Ty1Nb-Flag/Strep-Tag plasmid, by using EcoRI-HindIII restriction enzymes. Following restrict digest with these enzymes, pNKLab001 releases Intimin. Restriction digest of pNKLab001 and Lpp-OmpA signal was done with EcoRI-HindIII. The remaining backbone of pNKLab001 plasmid following the release of Intimin still contains the Ty1 nanobody. The top band of pNKLab001 and digested PCR product for Lpp-OmpA signal were ligated overnight as previously described. Following overnight ligation, 3.5 μL of ligation mixtures was chemically transformed into DH5α competent cells (NEB) and spread on chloramphenicol selection plates. Plates were incubated at 37° C. overnight. About 40-colonies were randomly screened for successful cloning by performing colony PCR on the selected colonies.

Example 7

Preliminary confirmation was done with Colony PCR for pNKLab003_(OmpA-Ty1Nb-Strp/Flag Tag). Following colony PCR confirmation, 5 colonies were selected and grown overnight in 3 ml using Chloramphenicol at 37° C. Plasmids were extracted from these 5-colonies using Clone-Jet plasmid extraction kit (Thermo Scientific) and sent for Sanger sequencing. Sequencing results were verified for mutations manually or by using software tools such as SnapGene and/or Multalign.

Example 8

Confirmation of nanobody expression was conducted with SDS-PAGE and western immunoanalysis. Following the final confirmation of successful molecular cloning of the Nanobodies and surface display signals, these constructs were ready for testing the expression of Nanobodies. Therefore, these constructs were chemically transformed into *E. coli* Nissle (EcN) and were spread on respective antibiotic selection plates. Plates were incubated at 37° C. overnight. After 24 hrs, a single colony each was picked from these plates for ALL the 4-nanobody expression constructs, pNKLab001, 002, 003 and 004 and grown in LB broth supplemented with chloramphenicol and incubated at 37° C. overnight. 1% of these cultures were inoculated into fresh 10 ml LB broth supplemented with chloramphenicol and grown until $OD_{600}$ reaches 0.9-1.0 (approx. 3.00 hr). These cultures were then centrifuged at 4° C. for 15 min at 3500×g and cells were resuspended in 2 ml of the media. These cells were redistributed in 500 μL 1.5 ml Eppendorf tube.

Both the tubes containing resuspended cells were centrifuged at 4° C. for 15 min at 13,000×g. For the 500 μL cells containing eppendorf's, supernatant was discarded and labelled as cell fraction. In the case of the Eppendorf's that contained 1.5 ml re-suspended cells, cell pellet was discarded and 1350 μL supernatant was collected in another Eppendorf and placed on ice. To these Eppendorf's, 150 μL of ice-cold Tri-Chloro Acetic Acid (TCA) was added, incubated on ice for 30 min, following which these were centrifuged at 4° C. for 15 min at 3500×g. The supernatant was discarded, and the pellet was washed with 950 μL of ice-cold Acetone and centrifuged at 4° C. for 15 min at 3500×g. Following centrifuge, the entire contents of the tube was decanted and air dried, prior to adding 2×SDS-loading buffer. The cell fraction and supernatant containing tubes were added with 2× loading buffer according to their $OD_{600}$ by using the following equation: a) Loading Buffer for cell pellet: $OD_{600} \times 200/2$; b) Loading buffer for cell supernatant: $OD_{600} \times 1500 \times 50$. Both of these cell fraction and cell supernatants were then heated at 95° C. for 15 min using a heat block, with intermittent shaking.

Meanwhile, 15% SDS-PAGE gels were prepared and placed in a SDS-running gel tank (BioRad) containing 1×SDS running buffer. The cell Fraction and cell supernatants were loaded on the gel and run at 95° C. for 2.5 3.0 hr. The gels were then transformed to Nitrocellulose paper by using Trans-blot Turbo transfer system (BioRad). Blots were then blocked using 5% milk in 0.1%, 1×TBS Tween buffer overnight at 4° C. These were then washed 3× using 0.1%, 1×TBS Tween and added with 1×TBS buffer. It was added with 1:500 HRP-conjugated Flag-Tag Antibody and incubated for 4.00 hr at room temperature.

These blots were then washed again 3× times with 0.1%, 1×TBW Tween buffer, and transferred into a suitable box and added with equal volumes of Chemiluminescent Dark and Light substrates (Super Signal, West Pico Plus, Thermo Scientific) and incubated for 5 min in dark at RT. These blots were then developed using ChemiDoc Imager (BioRad). The gels were subjected to Silver staining using Pierce™ Silver staining kit (Thermo Scientific), according to manufacturer's protocol.

The Covid-19 nanobodies were expressed on the bacterial cell surface using both Intimin and Lpp-OmpA secretion signals. The Nanobody constructs we generated viz. Intimin-VHH72, Intimin-Ty1, Lpp-OmpA-VHH72 and Lpp-OmpA-Ty1 were expressed in *E. coli* Nissle. SDS-PAGE Western blot analysis was performed for the confirmation of the nanobody expression using HRP conjugated Anti-Flag Tag antibodies (Sigma Aldrich). The nanobody expression was tested intracellularly and in the supernatant by using TCA-Acetone precipitation method. Expression of Ty1 (pNKLab003) and VHH72 (pNKLab004) nanobodies was observed, in cell fraction, which were fused with Lpp-OmpA surface display signal. Expression of Ty1 (pNKLab001) and VHH72 (pNKLab002) nanobodies were also observed in the supernatant.

Example 9—COVID19 Bio-Assay

Figure 9A:
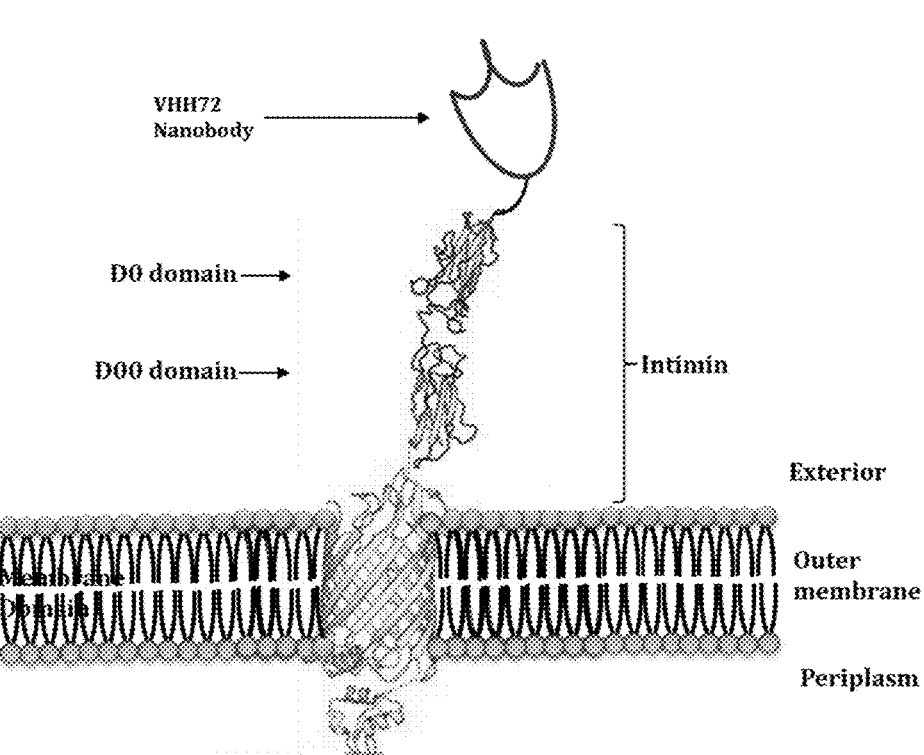
FIG. 9A is an illustration of a VHH72 nanobody fused to Intimin.
Figure 9B:
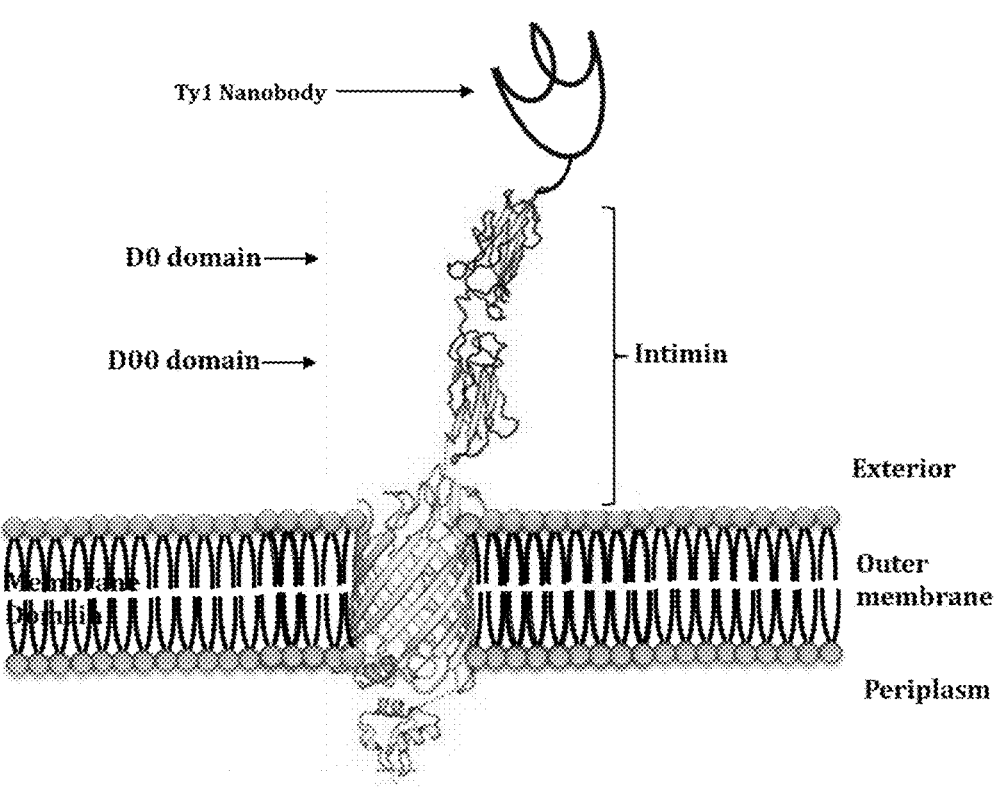
FIG. 9B is an illustration of a Ty1 nanobody fused to Intimin.
Figure 9C:
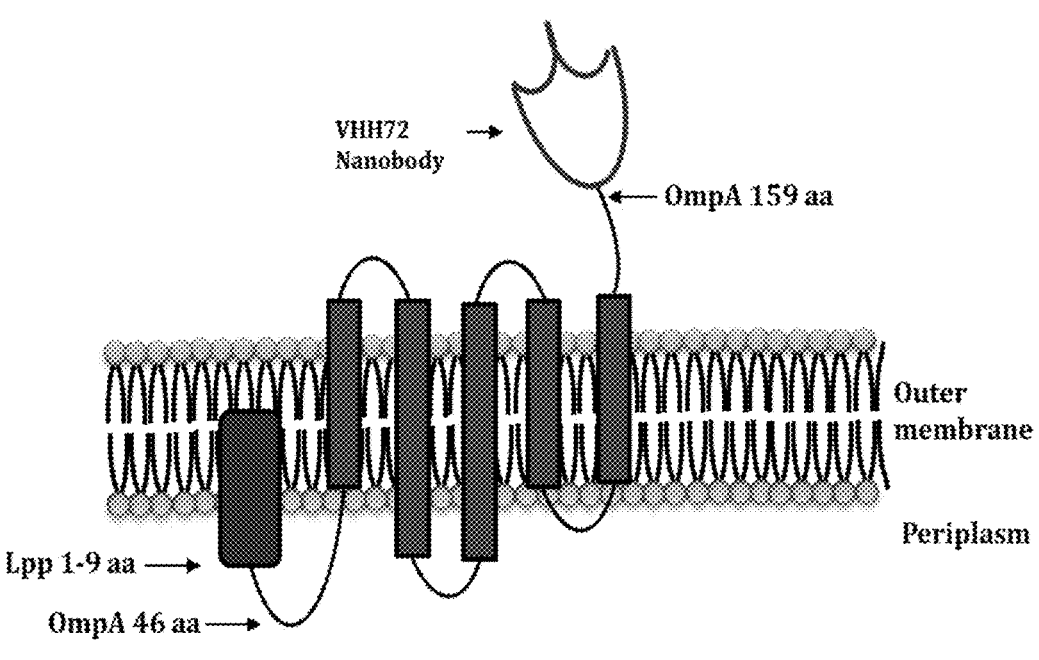
FIG. 9C is an illustration of a VHH72 nanobody fused to Lpp-OmpA.
Figure 9D:
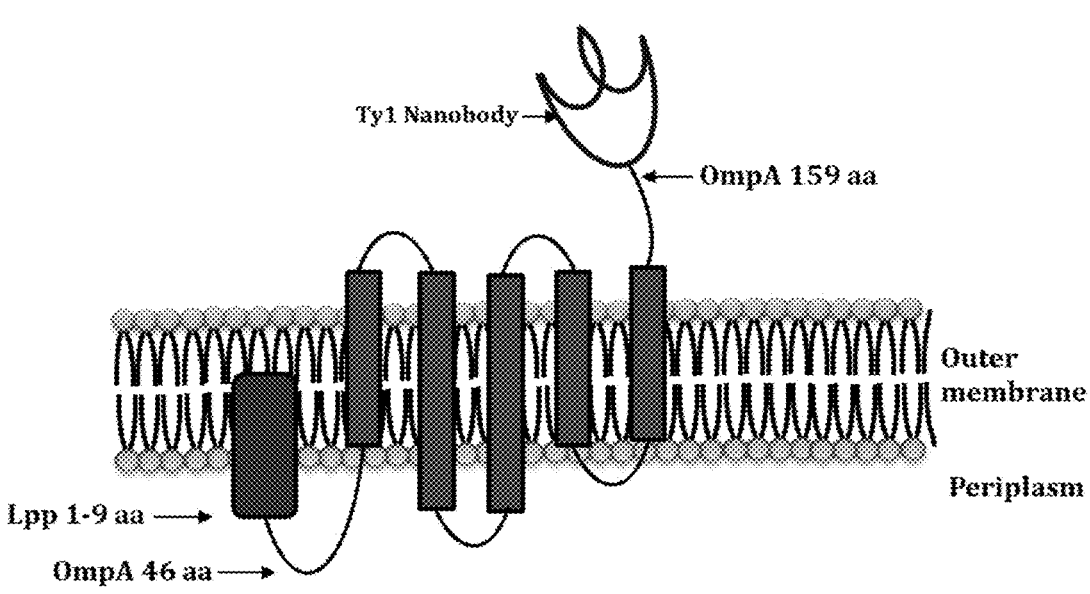
FIG. 9D is an illustration of a Ty1 nanobody fused to Lpp-OmpA.
Figure 9E:
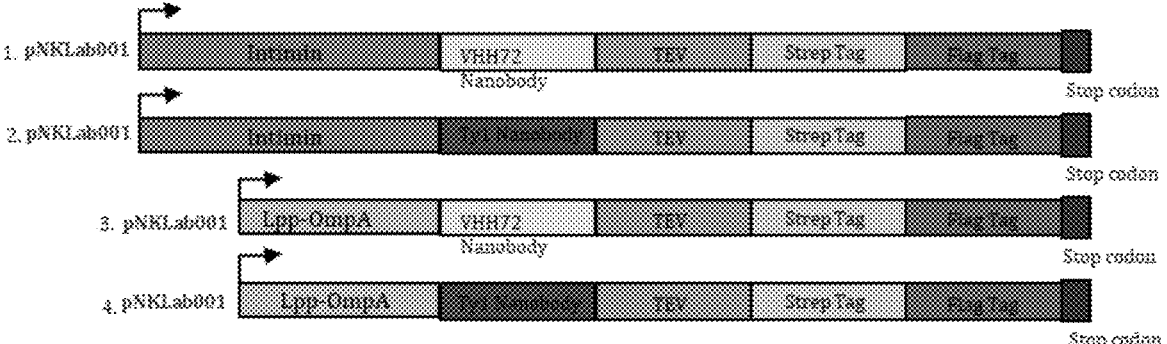
FIG. 9E is a series of linear maps of the gene blocks for pNKLab001, pNKLab002, pNKLab003 and pNKLab004.
Figure 10A:
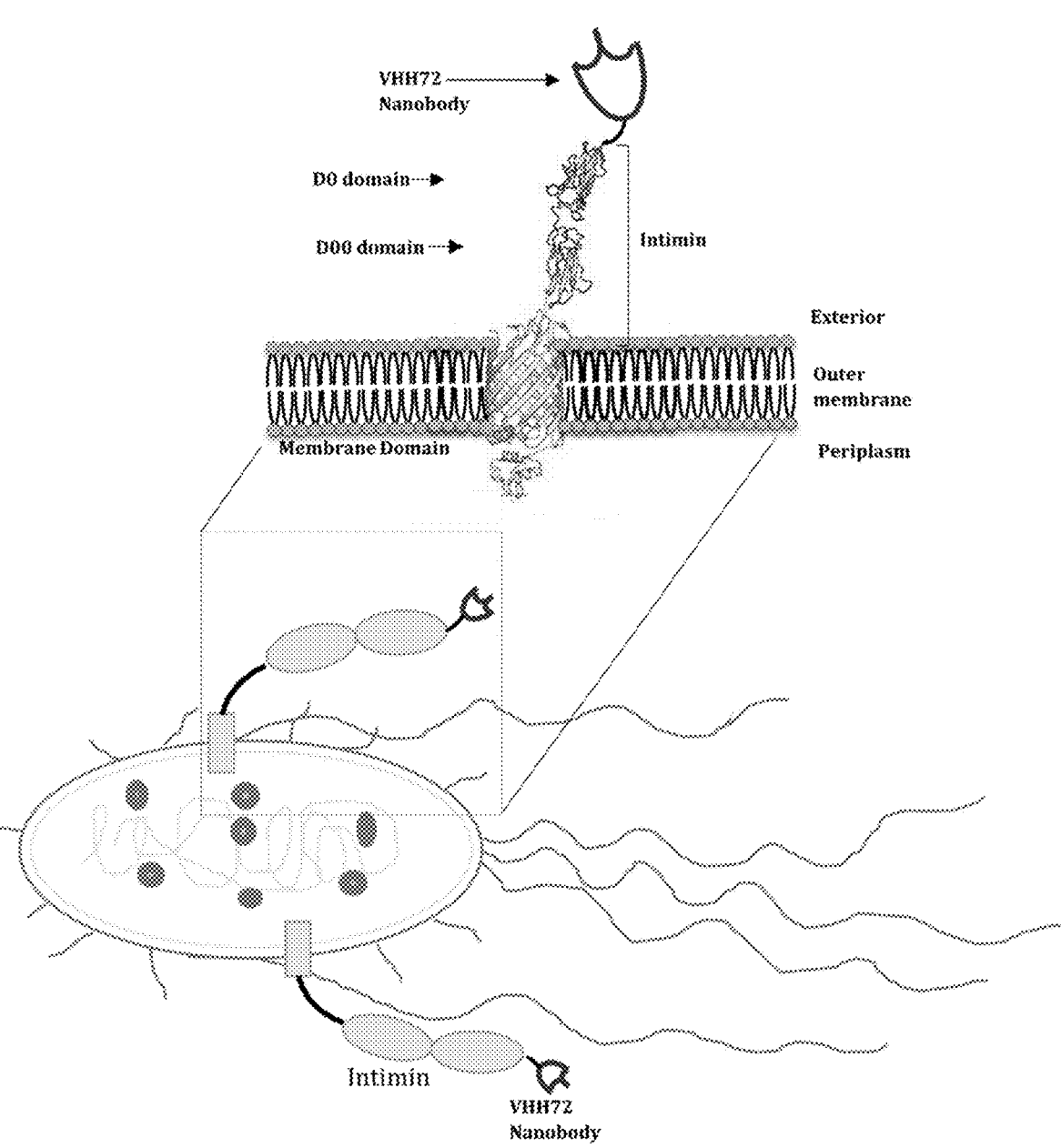
FIG. 10A is an illustration of the structure of FIG. 9A bound to the surface of a bacteria.
Figure 10B:
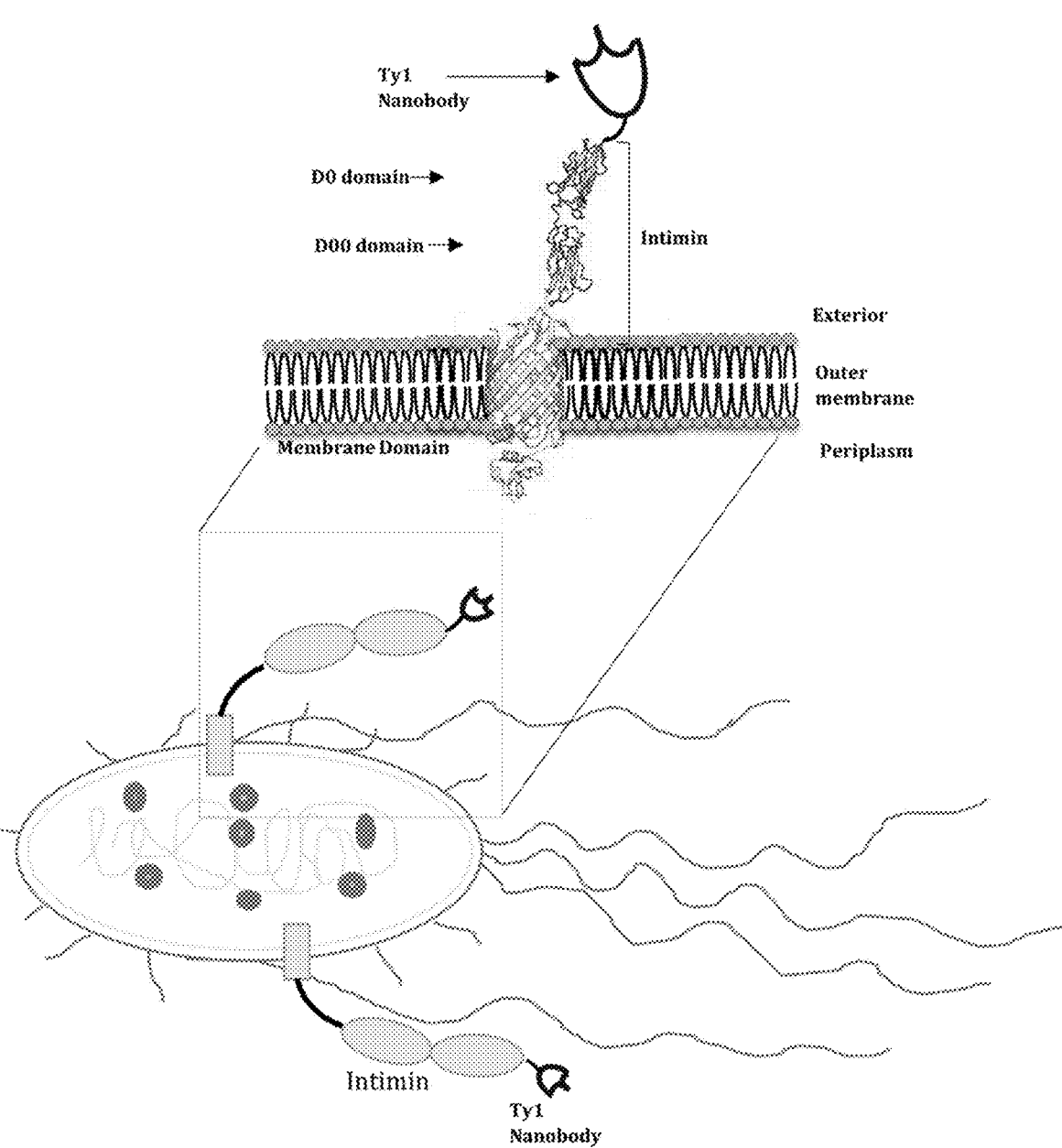
FIG. 10B is an illustration of the structure of FIG. 9B bound to the surface of a bacteria.
Figure 11A:
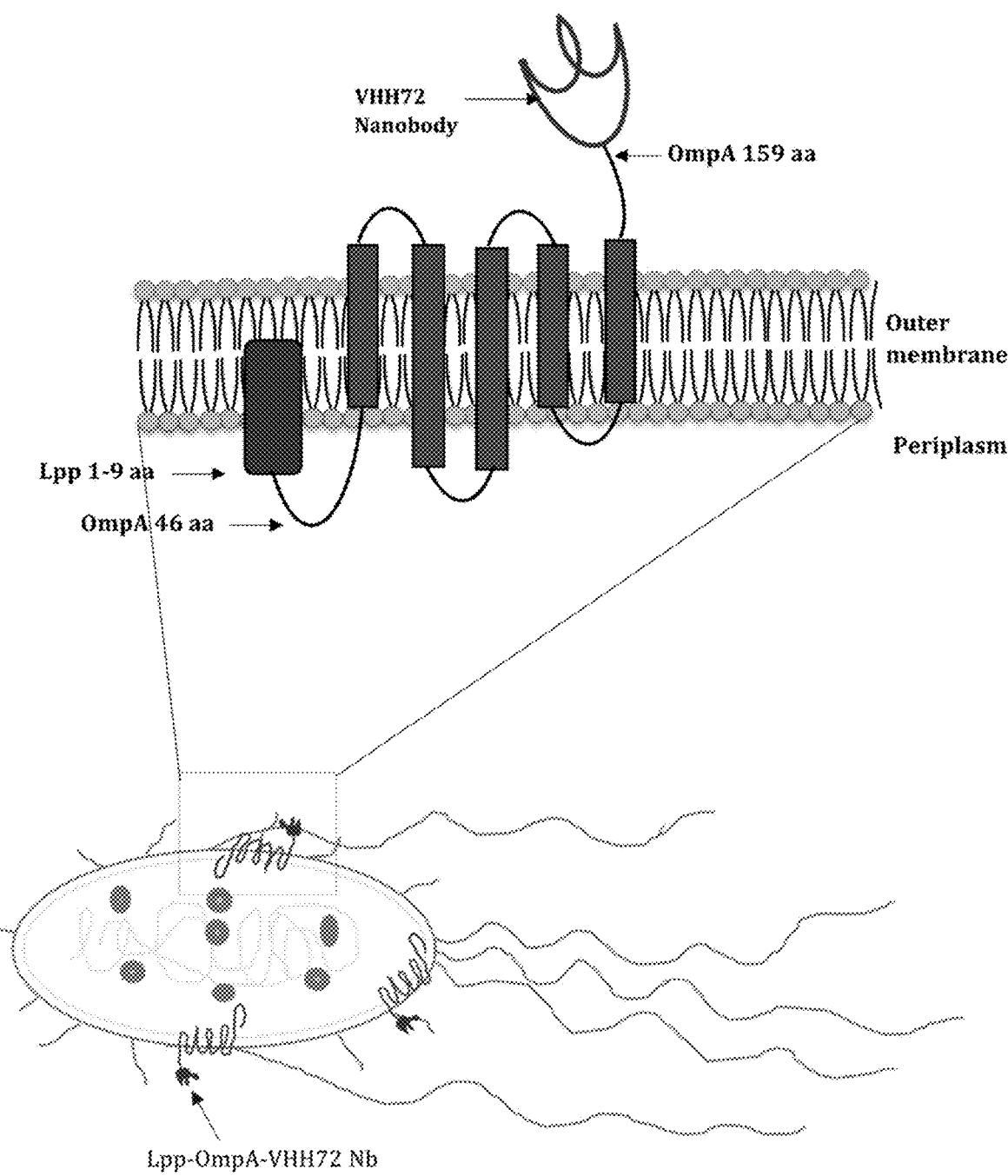
FIG. 11A is an illustration of the structure of FIG. 9C bound to the surface of a bacteria.
Figure 11B:
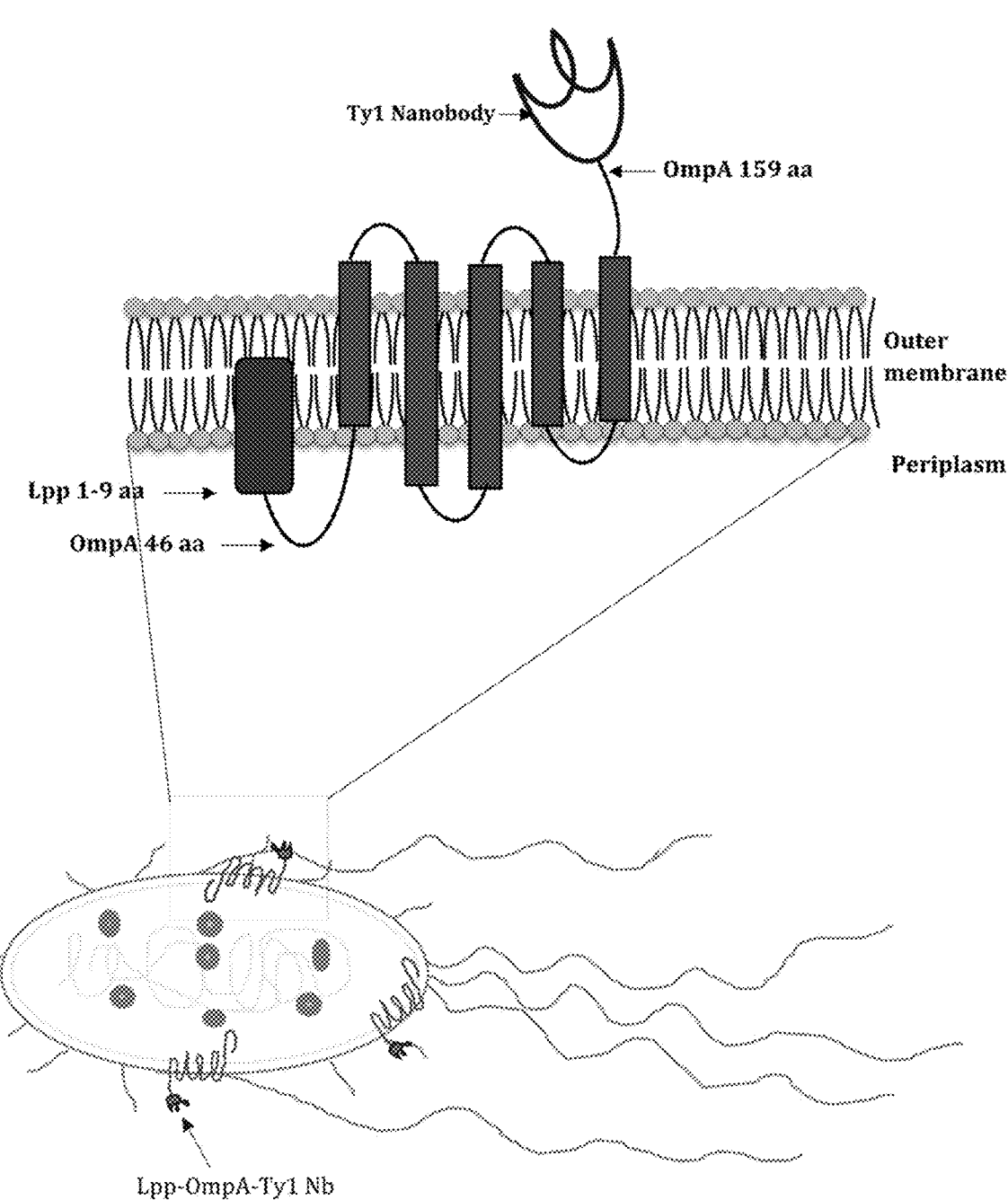
FIG. 11B is an illustration of the structure of FIG. 9D bound to the surface of a bacteria.
Figure 12:
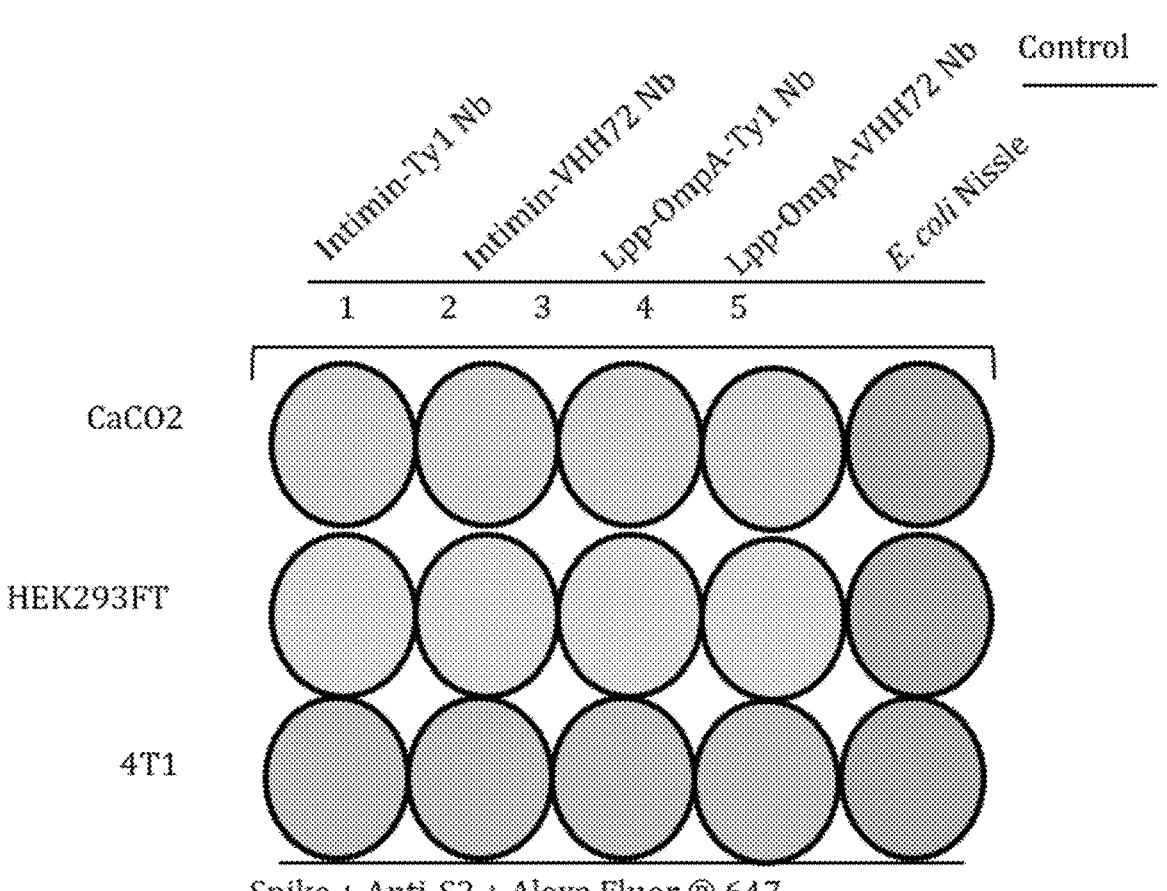
FIG. 12 is a schematic of the experimental approach described in Example 12 where the green well represents anticipated positive control.

VHH72 and Ty1 nanobody amino acids sequences that were reported against SARS Cov2 spike protein were accessed. The nanobody sequences were generated de novo utilizing a gene synthesis technology with the flanking BioBrick prefixes/suffixes, codon optimized using Online tools offered by GeneArt Synthesis (Thermo Scientific) and IDT. These gene blocks for Intimin, Lpp-OmpA surface display signals and the COVID19 nanobodies were assembled using Chloramphenicol resistant CJ23 plasmid in order to generate the pNKLab001-pNKLab004 constructs shown in FIG. 9E.

An in-house assay was developed for the determination of the functionality of the nanobody expression on the bacterial cell surface. As the nanobodies-VHH72 and Ty1 bind to the receptor binding domain (RBD) of the SARS-Cov2 spike protein, recombinant SARS-Cov2 S (S1+S2) protein was acquired, where nanobodies would bind to the S1 domain of the spike protein. In order to confirm this binding, the SARS Cov-2 S protein S2 antibody (BioLegend) that specifically binds to the S2 domain of the recombinant spike protein was used. Finally, this whole sandwich complex was visualized by using an AlexaFluor® conjugated anti-mouse IgG2b antibody (BioLegend), using a plate reader-based assay (schematic depicted in FIGS. 12A-12D).

Example 10

*Escherichia coli* Nissle were freshly transformed with pNKLab001, pNKLab002, pNKLab003 and pNKLab004 plasmids, while wild-type *E. coli* Nissle (EcN) was used as a control. All the cultures were grown identically in 10 ml LB medium supplemented with appropriate antibiotic, for approximately 3.00 hr or until $OD_{600}$ reaches 0.8-1.0. All the centrifugation steps were carried out at 3500×g for 15 min, at room temperature (RT) unless otherwise stated.

Following $OD_{600}$ measurements, 1 ml samples from each culture were centrifuged and pellets were resuspended in 1 ml of Phosphate Buffered Saline (PBS). It was centrifuged and pellets were re-suspended in 200 μl of PBS and it was added with 1 μg of Spike Protein (carrier-free Recombinant SARS-CoV-2 S Protein (S1+S2) (Bioline #793706)) and incubated in the dark for an hour at RT. Following centrifugation, it was then resuspended in 1 ml of PBS and centrifuged again, and pellet were resuspended into 200 μl of PBS. It was then added with 1 μg of Purified anti-SARS-CoV-2 Protein S2 antibody (Bioline #943202), that specifically binds to S2 fragment of spike protein. The whole reaction was incubated in the dark for 30 min. It was centrifuged and resuspended into 1 ml of PBS as previously and centrifuged. Following this, pellet was re-suspended into 200 μl of PBS and added with secondary antibody (Alexa Fluor® 647 anti-mouse IgG2b, Bioline #406715). Following 30 min of incubation in dark, the reactions tubes were centrifuged twice, and pellet were resuspended into 200 μl of PBS. The whole reaction mixture was placed into a transparent 96-well plate and read for fluorescence using a Fluorescent microscope (Leica Microsystems).

Example 11

In order to identify ACE-2 receptor and evaluate the interaction between ACE-2 receptor and Spike protein, an in-house assay was developed. In addition, a competitive exclusion assay was performed between engineered COVID19 nanobodies (Ty1 and VHH72) and the ACE-2 receptor for binding recombinant spike protein (carrier-free Recombinant SARS-CoV-2 S Protein (S1+S2) (Bioline #793706)).

Following cell lines were used for the development of the assay—CaCo2, which is positive for ACE2 receptor, and 4T1 cells, which is negative for ACE2. These cell lines were grown in respective media (ATCC) using an 8-chamber slide (Ibidi), until confluency by incubating at 37° C. with 5% CO2. The cell media were removed, and cell were washed 3 times with Phosphate Buffer Saline (PBS). Cells were then fixed using 4% formaldehyde by incubating for 10 min at room temperature (RT). The formaldehyde was drained, and cells were washed 3× times to remove the residual formaldehyde. It was followed by permeabilization. Cells were permeabilized with permeabilization buffer (0.1% Triton x100 in PBS) and incubated for 10 min at RT, followed by 3 washes with PBS. Cells were then blocked using blocking buffer (3% BSA in PBS with 0.1% Triton X100) for 30 min at RT. Following buffer removal, cells were added with primary antibody and/or spike protein prepared in 0.1% Triton X100, with 30 mg/ml of BSA (Filter sterilized). Primary antibody (Anti-ACE2 (E-11): sc-390851 (Santa Cruz Biotechnology Inc.)) was added for 1-2 hr at RT followed with 3× washes with wash Buffer (0.1% Triton X100 in PBS) (15 min washing with 5 min in between). It was followed with secondary antibody (Alexa Fluor® 647 anti-mouse IgG2b, Bioline #406715) prepared in PBS (0.1% Triton x100 with 30 mg/ml BSA).

When Spike protein was utilized, following the blocking step, and/or Anti-ACE2 washing step, cells were added with 1 μg of Spike Protein (carrier-free Recombinant SARS-CoV-2 S Protein (S1+S2) (Bioline #793706)) and incubated in dark for an hour at RT. Following 3× washes with Washing buffer, 1 μg of Purified anti-SARS-CoV-2 Protein S2 antibody (Bioline #943202) was added, that specifically binds to S2 fragment of Spike Protein. The whole reaction was incubated in dark for 30 min. Following 3× washes with washing buffer, secondary antibody (Alexa Fluor® 647 anti-mouse IgG2b, Bioline #406715) was added. After 30 min of incubation in dark, cells were washed 3× times with washing buffer and were visualized for fluorescence, using a fluorescent microscope.

Example 12

A competitive exclusion assay was used to evaluate sequestration of spike protein. In order to evaluate the competition between engineered COVID19 nanobodies located on bacterial cell surfaces with Intimin or Lpp-OmpA anchor (FIG. 9E) and the ACE-2 receptor located on Cell lines (CACo2, HE293FT and 4T1), for COVID19 Spike protein, an assay was performed (schematic outlined in FIG. 12). The assay was performed as outlined earlier. In brief, the following cell lines were grown until confluency as previously described. In parallel, *E. coli* Nissle harboring respective surface anchor and Nanobody from an overnight culture was added on the top of the cell lines in the 8-well chamber slides. It was then sequentially added with Spike protein, anti-S2 antibody and AlexaFluor® Antibody as previously described, while wild type *E. coli* Nissle was used as a positive control.

Figure 13:
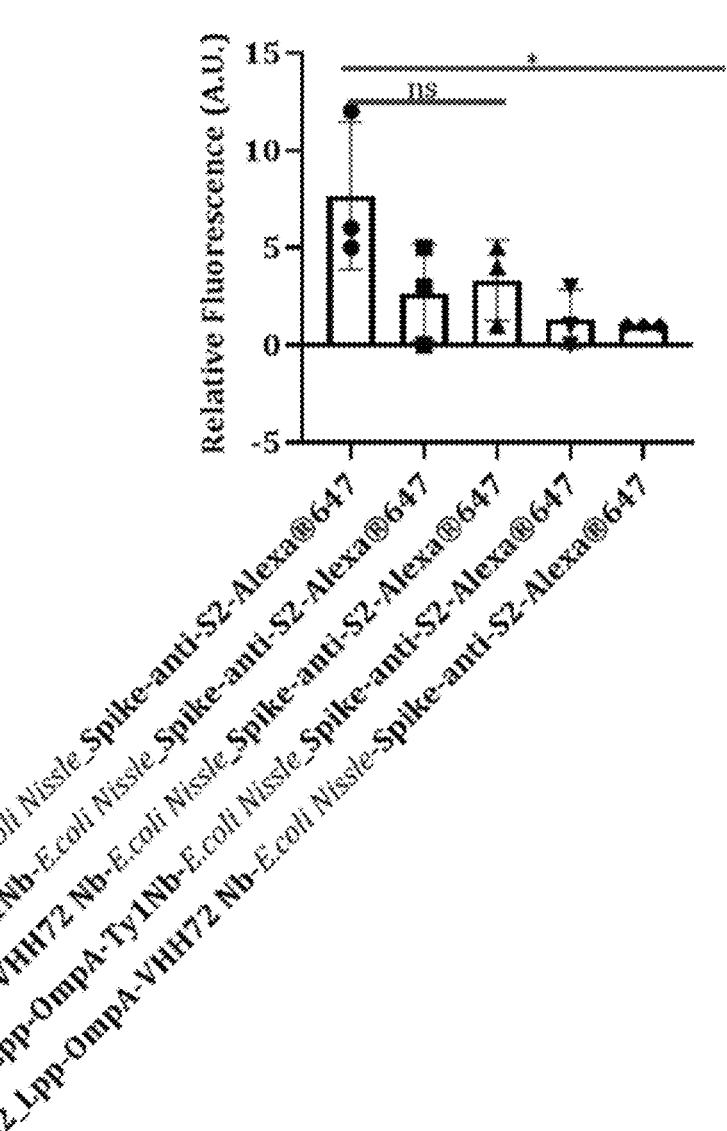
FIG. 13 is a graph of the experimental results showing the sequestration of spike protein using various embodiments of the present invention.

Following fluorescent microscopy, as shown in FIG. 13, spike protein binds to the ACE-2 receptor located on CaCo2 Cell lines enabling the sequential binding of anti-S2 antibody and AlexaFluor Antibody, which is significantly different (p 0.05) than the *E. coli* Nissle harboring COVID19 nanobodies on the cell surface. It also suggests that when nanobodies are attached with Lpp-OmpA surface display signal, it more efficiently sequesters the spike protein away from the ACE2 receptor than when these are anchored with Intimin (see FIG. 13).

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

SEQUENCES

SEQ ID NO:1, SEQ ID NO: 2, SEQ ID NO:3 and SEQ ID NO:4 identify the DNA sequences for embodiments of the nanobodies of the present invention.

SEQ ID NO: 5, SEQ ID NO: 6, SEQ ID NO: 7, SEQ ID NO: 8, SEQ ID NO: 9 and SEQ ID NO: 10 identify the DNA sequences for embodiments of the plasmids of the present invention.

SEQ ID NO: 11 identifies the DNA sequence for a CJ23 plasmid.

The material contained in the ASCII plain text file "REPLACEMENT_08_14_2023," created Aug. 14, 2023, which is 48 kilobytes, is hereby incorporated by reference, in accordance with § 1.77(b)(5).

```
                                                          SEQ ID NO: 1
caggtgcagc tgcaggaaag cggtggtggt ctggtgcagg ccggtggtag cctgcgtctg      60
agctgtgccg ccagcggtcg tacctttagc gaatatgcca tgggttggtt tcgtcaggcc     120
ccgggtaaag aacgtgaatt tgtggccacc attagctgga gcggtggtag cacctattat     180
accgatagcg tgaaaggtcg ttttaccatt agccgtgata atgccaaaaa taccgtgtat     240
ctgcagatga atagcctgaa accggatgat accgccgtgt attattgtgc cgccgccggt     300
ctgggtaccg tggtgagcga atgggattat gattatgatt attggggtca gggtacccag     360
gtgaccgtga gcagcggtag c                                               381

SEQ ID NO: 2
aagcttcatc accatcacca tcacggtggt ggtggtagcc aggtgcagct gcaggaaagc      60
ggtggtggtc tggtgcaggc cggtggtagc ctgcgtctga gctgtgccgc cagcggtcgt     120
acctttagcg aatatgccat gggttggttt cgtcaggccc gggtaaaga acgtgaattt     180 gtggccacca ttagctggag cggtggtagc acctattata ccgatagcgt gaaaggtcgt     240
tttaccatta gccgtgataa tgccaaaaat accgtgtatc tgcagatgaa tagcctgaaa     300
```

-continued

```
ccggatgata ccgccgtgta ttattgtgcc gccgccggtc tgggtaccgt ggtgagcgaa          360
tgggattatg attatgatta ttggggtcag ggtacccagg tgaccgtgag cagcggtagc          420
taaaagctt                                                                  429
```

SEQ ID NO: 3
```
caggtgcagc tggtggaaac cggcggcggc ctggtgcagc cgggcggcag cctgcgcctg           60
agctgcgcgg cgagcggctt tacctttagc agcgtgtata tgaactgggt gcgccaggcg          120
ccgggcaaag gcccggaatg ggtgagccgc attagcccga cagcggcaa cattggctat          180 accgatagcg tgaaaggccg ctttaccatt agccgcgata cgcgaaaaa caccctgtat          240 ctgcagatga caacctgaa accggaagat accgcgctgt attattgcgc gattggcctg          300
aacctgagca gcagcagcgt gcgcggccag ggcacccagg tgaccgtgag cagc               354
```

SEQ ID NO: 4
```
aagcttgaaa acctgtactt ccaaggtgaa ttccaggtgc agctggtgga aaccggcggc           60
ggcctggtgc agccgggcgg cagcctgcgc ctgagctgcg cggcgagcgg ctttaccttt          120
agcagcgtgt atatgaactg gtgcgccag gcgccgggca aaggcccgga atgggtgagc          180
cgcattagcc cgaacagcgg caacattggc tataccgata gcgtgaaagg ccgctttacc          240
attagccgcg ataacgcgaa aaacaccctg tatctgcaga tgaacaacct gaaaccggaa          300
gataccgcgc tgtattattg cgcgattggc ctgaacctga gcagcagcag cgtgcgcggc          360
cagggcaccc aggtgaccgt gagcagcgga tccgaaaacc tgtacttcca aggtgactac          420
aaggacgatg acgataagtg gagccatccg cagtttgaga atctagaaa gctttaacat          480 atgactcgag t                                                              491
```

SEQ ID NO: 5
```
gacgtcttga cagctagctc agtcctaggg attgtgctag caggtttaat cgaattgacg           60
tctttacggc tagctcagtc ctaggtacta tgctagcagg tttaatcgaa ttcaaaagat          120
cttttaagaa ggagatatac atatgattac tcatggttgt tatacccgga cccggcacaa          180
gcataagcta aaaaaaacat tgattatgct tagtgctggt ttaggattgt ttttttatgt          240
taatcagaac tcatttgcaa atggtgaaaa ttattttaaa ttgggttcgg attcaaaact          300
gttaactcat gatagctatc agaatcgcct tttttatacg ttgaaaactg gtgaaactgt          360
tgccgatctt tctaaatcgc aagatattaa tttatcgacg atttggtcgt tgaataagca          420
tttatacagt tctgaaagcg aaatgatgaa ggccgcgcct ggtcagcaga tcattttgcc          480
actcaaaaaa cttccctttg aatacagtgc actaccactt ttaggttcgg cacctcttgt          540
tgctgcgggt ggtgttgctg tcacacgaa taaactgact aaaatgtccc cggacgtgac          600
caaaagcaac atgaccgatg acaaggcatt aaattatgcg gcacaacagg cggcgagtct          660
cggtagccag cttcagtcgc gatctctgaa cggcgattac gcgaaagata ccgctcttgg          720
tatcgctggt aaccaggctt cgtcacagtt gcaggcctgg ttacaacatt atggaacggc          780
agaggttaat ctgcaaagtg gtaataactt tgacggtagt tcactggact tcttattacc          840
gttctatgat tccgaaaaaa tgctggcatt tggtcaggtc ggagcgcgtt acattgactc          900
ccgctttacg gcaaatttag gtgcgggtca gcgttttttc cttcctgcaa acatgttggg          960
ctataacgtc ttcattgatc aggatttttc tggtgataat acccgtttag gtattggtgg         1020
cgaatactgg cgagactatt tcaaaagtag cgttaacggc tatttccgca tgagcggctg         1080
gcatgagtca tacaataaga aagactatga tgagcgccca gcaaatggct tcgatatccg         1140
ttttaatggc tatctaccgt catatccggc attaggcgcc aagctgatat atgagcagta         1200
ttatggtgat aatgttgctt tgtttaattc tgataagctg caatcgaatc ctggtgcggc         1260
```

-continued

```
gaccgttggt gtaaactata ctccgattcc tctggtgacg atggggatcg attaccgtca    1320
tggtacgggt aatgaaaatg atctccttta ctcaatgcag ttccgttatc agtttgataa    1380
atcgtggtct cagcaaattg aaccacagta tgttaacgag ttaagaacat tatcaggcag    1440
ccgttacgat ctggttcagc gtaataacaa tattattctg gagtacaaga agcaggatat    1500
tctttctctg aatattccgc atgatattaa tggtactgaa cacagtacgc agaagattca    1560
gttgatcgtt aagagcaaat acggtctgga tcgtatcgtc tgggatgata gtgcattacg    1620
cagtcagggc ggtcagattc agcatagcgg aagccaaagc gcacaagact accaggctat    1680
tttgcctgct tatgtgcaag gtggcagcaa tatttataaa gtgacggctc gcgcctatga    1740
ccgtaatggc aatagctcta acaatgtaca gcttactatt accgttctgt cgaatggtca    1800
agttgtcgac caggttgggg taacggactt tacggcggat aagacttcgg ctaaagcgga    1860
taacgccgat accattactt ataccgcgac ggtgaaaaag aatggggtag ctcaggctaa    1920
tgtccctgtt tcatttaata ttgtttcagg aactgcaact cttggggcaa atagtgccaa    1980
aacggatgct aacggtaagg caaccgtaac gttgaagtcg agtacgccag acaggtcgt     2040 cgtgtctgct aaaaccgcgg agatgacttc agcacttaat gccagtgcgg ttatatttt     2100 tgatggtgcg cccgggaagc ttgaaaacct gtacttccaa ggtacgcgtc aggtgcagct    2160
ggtggaaacc ggcggcggcc tggtgcagcc gggcggcagc ctgcgcctga gctgcgcggc    2220
gagcggcttt acctttagca gcgtgtatat gaactgggtg cgccaggcgc gggcaaagg     2280 cccggaatgg gtgagccgca ttagcccgaa cagcggcaac attggctata ccgatagcgt    2340
gaaaggccgc tttaccatta gccgcgataa cgcgaaaaac accctgtatc tgcagatgaa    2400
caacctgaaa ccggaagata ccgcgctgta ttattgcgcg attggcctga acctgagcag    2460
cagcagcgtg cgcggccagg gcacccaggt gaccgtgagc agcggatccg aaaacctgta    2520
cttccaaggt gactacaagg acgatgacga taagtggagc catccgcagt ttgagaaatc    2580
tagataaggt accactcgag taaggatctc caggcatcaa ataaaacgaa aggctcagtc    2640
gaaagactgg gcctttcgtt ttatctgttg tttgtcggtg aacgctctct actagagtca    2700
cactggctca ccttcgggtg ggcctttctg cgtttatacc tagggtacgg gttttgctgc    2760
ccgcaaacgg gctgttctgg tgttgctagt ttgttatcag aatcgcagat ccggcttcag    2820
ccggtttgcc ggctgaaagc gctatttctt ccagaattgc catgattttt tccccacggg    2880
aggcgtcact ggctcccgtg ttgtcggcag ctttgattcg ataagcagca tcgcctgttt    2940
caggctgtct atgtgtgact gttgagctgt aacaagttgt ctcaggtgtt caatttcatg    3000
ttctagttgc tttgttttac tggtttcacc tgttctatta ggtgttacat gctgttcatc    3060
tgttacattg tcgatctgtt catggtgaac agctttgaat gcaccaaaaa ctcgtaaaag    3120
ctctgatgta tctatctttt ttacaccgtt ttcatctgtg catatggaca gttttccctt    3180
tgatatgtaa cggtgaacag ttgttctact tttgtttgtt agtcttgatg cttcactgat    3240
agatacaaga gccataagaa cctcagatcc ttccgtattt agccagtatg ttctctagtg    3300
tggttcgttg tttttgcgtg agccatgaga acgaaccatt gagatcatac ttactttgca    3360
tgtcactcaa aaattttgcc tcaaaactgg tgagctgaat ttttgcagtt aaagcatcgt    3420
gtagtgtttt tcttagtccg ttatgtaggt aggaatctga tgtaatggtt gttggtattt    3480
tgtcaccatt cattttttatc tggttgttct caagttcggt tacgagatcc atttgtctat    3540
ctagttcaac ttggaaaatc aacgtatcag tcgggcggcc tcgcttatca accaccaatt    3600
tcatattgct gtaagtgttt aaatctttac ttattggttt caaaacccat tggttaagcc    3660
ttttaaactc atggtagtta ttttcaagca ttaacatgaa cttaaattca tcaaggctaa    3720
```

-continued

```
tctctatatt tgccttgtga gttttctttt gtgttagttc ttttaataac cactcataaa      3780
tcctcataga gtatttgttt tcaaaagact taacatgttc cagattatat tttatgaatt      3840
tttttaactg gaaaagataa ggcaatatct cttcactaaa aactaattct aattttttcgc     3900 ttgagaactt ggcatagttt gtccactgga aaatctcaaa gcctttaacc aaaggattcc      3960
tgatttccac agttctcgtc atcagctctc tggttgcttt agctaataca ccataagcat      4020
tttccctact gatgttcatc atctgagcgt attggttata agtgaacgat accgtccgtt      4080
ctttccttgt agggtttttca atcgtggggt tgagtagtgc cacacagcat aaaattagct     4140
tggtttcatg ctccgttaag tcatagcgac taatcgctag ttcatttgct ttgaaaacaa      4200
ctaattcaga catacatctc aattggtcta ggtgattttta atcactatac caattgagat     4260
gggctagtca atgataatta ctagtccttt tcccgggtga tctgggtatc tgtaaattct      4320
gctagacctt tgctggaaaa cttgtaaatt ctgctagacc ctctgtaaat tccgctagac      4380
ctttgtgtgt ttttttttgtt tatattcaag tggttataat ttatagaata aagaaagaat    4440
aaaaaaagat aaaaagaata gatcccagcc ctgtgtataa ctcactactt tagtcagttc      4500
cgcagtatta caaaaggatg tcgcaaacgc tgtttgctcc tctacaaaac agaccttaaa      4560
accctaaagg cttaagtagc accctcgcaa gctcgggcaa atcgctgaat attccttttg      4620
tctccgacca tcaggcacct gagtcgctgt ctttttcgtg acattcagtt cgctgcgctc      4680
acggctctgg cagtgaatgg gggtaaatgg cactacaggc gccttttatg gattcatgca      4740
aggaaactac ccataataca agaaaagccc gtcacgggct tctcagggcg ttttatggcg      4800
ggtctgctat gtggtgctat ctgacttttt gctgttcagc agttcctgcc ctctgatttt      4860
ccagtctgac cacttcggat tatcccgtga caggtcattc agactggcta atgcacccag      4920
taaggcagcg gtatcatcaa caggcttacc cgtcttactg tccctagtgc ttggattctc      4980
accaataaaa aacgcccggc ggcaaccgag cgttctgaac aaatccagat ggagttctga      5040
ggtcattact ggatctatca acaggagtcc aagcgagctc gatatcaaat tacgccccgc      5100
cctgccactc atcgcagtac tgttgtaatt cattaagcat tctgccgaca tggaagccat      5160
cacaaacggc atgatgaacc tgaatcgcca gcggcatcag caccttgtcg ccttgcgtat      5220
aatatttgcc catggtgaaa acgggggcga agaagttgtc catattggcc acgtttaaat      5280
caaaactggt gaaactcacc cagggattgg ctgagacgaa aaacatattc tcaataaacc      5340
ctttagggaa ataggccagg ttttcaccgt aacacgccac atcttgcgaa tatatgtgta      5400
gaaactgccg gaaatcgtcg tggtattcac tccagagcga tgaaaacgtt tcagtttgct      5460
catggaaaac ggtgtaacaa gggtgaacac tatcccatat caccagctca ccgtctttca      5520
ttgccatacg aaattccgga tgagcattca tcaggcgggc aagaatgtga ataaaggccg      5580
gataaaactt gtgcttattt ttctttacgg tctttaaaaa ggccgtaata tccagctgaa      5640
cggtctggtt ataggtacat tgagcaactg actgaaatgc ctcaaaatgt tctttacgat      5700
gccattggga tatatcaacg gtggtatatc cagtgatttt tttctccatt ttagcttcct      5760
tagctcctga aaatctcgat aactcaaaaa atacgcccgg tagtgatctt atttcattat      5820
ggtgaaagtt ggaacctctt acgtgccgat caacgtctca ttttcgccag atatc          5875
```

```
                                                  SEQ ID NO: 6
gacgtcttga cagctagctc agtcctaggg attgtgctag caggtttaat cgaattgacg       60
tctttacggc tagctcagtc ctaggtacta tgctagcagg tttaatcgaa ttcaaaagat      120
cttttaagaa ggagatatac atatgattac tcatggttgt tatacccgga cccggcacaa      180
gcataagcta aaaaaaacat tgattatgct tagtgctggt ttaggattgt tttttttatgt     240
```

-continued

```
taatcagaac tcatttgcaa atggtgaaaa ttattttaaa ttgggttcgg attcaaaact      300
gttaactcat gatagctatc agaatcgcct tttttatacg ttgaaaactg gtgaaactgt      360
tgccgatctt tctaaatcgc aagatattaa tttatcgacg atttggtcgt tgaataagca      420
tttatacagt tctgaaagcg aaatgatgaa ggccgcgcct ggtcagcaga tcattttgcc      480
actcaaaaaa cttcccttttg aatacagtgc actaccactt ttaggttcgg cacctcttgt      540
tgctgcgggt ggtgttgctg gtcacacgaa taaactgact aaaatgtccc cggacgtgac      600
caaaagcaac atgaccgatg acaaggcatt aaattatgcg gcacaacagg cggcgagtct      660
cggtagccag cttcagtcgc gatctctgaa cggcgattac gcgaaagata ccgctcttgg      720
tatcgctggt aaccaggctt cgtcacagtt gcaggcctgg ttacaacatt atggaacggc      780
agaggttaat ctgcaaagtg gtaataactt tgacggtagt tcactggact tcttattacc      840
gttctatgat tccgaaaaaa tgctggcatt tggtcaggtc ggagcgcgtt acattgactc      900
ccgctttacg gcaaatttag gtgcgggtca gcgtttttttc cttcctgcaa acatgttggg      960
ctataacgtc ttcattgatc aggattttttc tggtgataat acccgtttag gtattggtgg     1020
cgaatactgg cgagactatt tcaaaagtag cgttaacggc tatttccgca tgagcggctg     1080
gcatgagtca tacaataaga aagactatga tgagcgccca gcaaatggct tcgatatccg     1140
ttttaatggc tatctaccgt catatccggc attaggcgcc aagctgatat atgagcagta     1200
ttatggtgat aatgttgctt tgtttaattc tgataagctg caatcgaatc ctggtgcggc     1260
gaccgttggt gtaaactata ctccgattcc tctggtgacg atggggatcg attaccgtca     1320
tggtacgggt aatgaaaatg atctcctttta ctcaatgcag ttccgttatc agtttgataa     1380
atcgtggtct cagcaaattg aaccacagta tgttaacgag ttaagaacat tatcaggcag     1440
ccgttacgat ctggttcagc gtaataacaa tattattctg gagtacaaga agcaggatat     1500
tctttctctg aatattccgc atgatattaa tggtactgaa cacagtacgc agaagattca     1560
gttgatcgtt aagagcaaat acggtctgga tcgtatcgtc tgggatgata gtgcattacg     1620
cagtcagggc ggtcagattc agcatagcgg aagccaaagc gcacaagact accaggctat     1680
tttgcctgct tatgtgcaag gtggcagcaa tatttataaa gtgacggctc gcgcctatga     1740
ccgtaatggc aatagctcta acaatgtaca gcttactatt accgttctgt cgaatggtca     1800
agttgtcgac caggttgggg taacggactt tacggcggat aagacttcgg ctaaagcgga     1860
taacgccgat accattactt ataccgcgac ggtgaaaaag aatggggtag ctcaggctaa     1920
tgtccctgtt tcatttaata ttgtttcagg aactgcaact cttggggcaa atagtgccaa     1980
aacggatgct aacggtaagg caaccgtaac gttgaagtcg agtacgccag gacaggtcgt     2040
cgtgtctgct aaaaccgcgg agatgacttc agcacttaat gccagtgcgg ttatatttttt     2100 tgatggtgcg cccgggaagc ttgaaaacct gtattttcag ggcacccgtc aggttcagct     2160
ggttgaaacc ggtggtggtc tggttcagcc tggtggtagc ctgcgtctga ctgtgcagc     2220 aagcggtttt acctttagca gcgtttatat gaattgggtt cgtcaggcac ctggtaaagg     2280
tccggaatgg gttagccgta ttagcccgaa tagcggtaat attggttata ccgatagcgt     2340
gaaaggtcgc tttaccatta gccgtgataa tgcaaaaaat accctgtacc tgcagatgaa     2400
taatctgaaa ccggaagata ccgcactgta ttattgtgca attggtctga atctgagcag     2460
cagcagcgtt cgtggtcagg tacacaggt taccgtgagc agcggtagcg agaatctgta     2520
tttccaaggt gattataaag acgacgatga caagtggtcc catccgcagt ttgaaaaaag     2580
ccgttaaggt accactcgag taaggatctc caggcatcaa ataaaacgaa aggctcagtc     2640
```

-continued

```
gaaagactgg gcctttcgtt ttatctgttg tttgtcggtg aacgctctct actagagtca   2700
cactggctca ccttcgggtg ggcctttctg cgtttatacc tagggtacgg gttttgctgc   2760
ccgcaaacgg gctgttctgg tgttgctagt ttgttatcag aatcgcagat ccggcttcag   2820
ccggtttgcc ggctgaaagc gctatttctt ccagaattgc catgattttt tccccacggg   2880
aggcgtcact ggctcccgtg ttgtcggcag ctttgattcg ataagcagca tcgcctgttt   2940
caggctgtct atgtgtgact gttgagctgt aacaagttgt ctcaggtgtt caatttcatg   3000
ttctagttgc tttgttttac tggtttcacc tgttctatta ggtgttacat gctgttcatc   3060
tgttacattg tcgatctgtt catggtgaac agctttgaat gcaccaaaaa ctcgtaaaag   3120
ctctgatgta tctatctttt ttacaccgtt ttcatctgtg catatggaca gttttccctt   3180
tgatatgtaa cggtgaacag ttgttctact tttgtttgtt agtcttgatg cttcactgat   3240
agatacaaga gccataagaa cctcagatcc ttccgtattt agccagtatg ttctctagtg   3300
tggttcgttg ttttttgcgtg agccatgaga acgaaccatt gagatcatac ttactttgca   3360
tgtcactcaa aaattttgcc tcaaaactgg tgagctgaat ttttgcagtt aaagcatcgt   3420
gtagtgtttt tcttagtccg ttatgtaggt aggaatctga tgtaatggtt gttggtattt   3480
tgtcaccatt cattttttatc tggttgttct caagttcggt tacgagatcc atttgtctat   3540
ctagttcaac ttggaaaatc aacgtatcag tcgggcggcc tcgcttatca accaccaatt   3600
tcatattgct gtaagtgttt aaatctttac ttattggttt caaaacccat tggttaagcc   3660
ttttaaactc atggtagtta tttttcaagca ttaacatgaa cttaaattca tcaaggctaa   3720
tctctatatt tgccttgtga gttttctttt gtgttagttc ttttaataac cactcataaa   3780
tcctcataga gtatttgttt tcaaaagact taacatgttc cagattatat tttatgaatt   3840
tttttaactg gaaaagataa ggcaatatct cttcactaaa aactaattct aattttttcgc   3900 ttgagaactt ggcatagttt gtccactgga aaatctcaaa gcctttaacc aaaggattcc   3960
tgatttccac agttctcgtc atcagctctc tggttgcttt agctaataca ccataagcat   4020
tttccctact gatgttcatc atctgagcgt attggttata agtgaacgat accgtccgtt   4080
ctttccttgt agggtttttca atcgtggggt tgagtagtgc cacacagcat aaaattagct   4140
tggtttcatg ctccgttaag tcatagcgac taatcgctag ttcatttgct ttgaaaacaa   4200
ctaattcaga catacatctc aattggtcta ggtgatttta atcactatac caattgagat   4260
gggctagtca atgataatta ctagtccttt tcccgggtga tctgggtatc tgtaaattct   4320
gctagacctt tgctggaaaa cttgtaaatt ctgctagacc ctctgtaaat tccgctagac   4380
ctttgtgtgt ttttttttgtt tatattcaag tggttataat ttatagaata aagaaagaat   4440
aaaaaaagat aaaagaata gatcccagcc ctgtgtataa ctcactactt tagtcagttc   4500
cgcagtatta caaaaggatg tcgcaaacgc tgtttgctcc tctacaaaac agaccttaaa   4560
accctaaagg cttaagtagc accctcgcaa gctcgggcaa atcgctgaat attccttttg   4620
tctccgacca tcaggcacct gagtcgctgt cttttttcgtg acattcagtt cgctgcgctc   4680
acggctctgg cagtgaatgg gggtaaatgg cactacaggc gccttttatg gattcatgca   4740
aggaaactac ccataataca agaaaagccc gtcacgggct tctcagggcg ttttatggcg   4800
ggtctgctat gtggtgctat ctgacttttt gctgttcagc agttcctgcc ctctgatttt   4860
ccagtctgac cacttcggat tatcccgtga caggtcattc agactggcta atgcacccag   4920
taaggcagcg gtatcatcaa caggcttacc cgtcttactg tccctagtgc ttggattctc   4980
accaataaaa aacgcccggc ggcaaccgag cgttctgaac aaatccagat ggagttctga   5040
ggtcattact ggatctatca acaggagtcc aagcgagctc gatatcaaat tacgccccgc   5100
```

-continued

```
cctgccactc atcgcagtac tgttgtaatt cattaagcat tctgccgaca tggaagccat       5160
cacaaacggc atgatgaacc tgaatcgcca gcggcatcag caccttgtcg ccttgcgtat       5220
aatatttgcc catggtgaaa acgggggcga agaagttgtc catattggcc acgtttaaat       5280
caaaactggt gaaactcacc cagggattgg ctgagacgaa aaacatattc tcaataaacc       5340
ctttagggaa ataggccagg ttttcaccgt aacacgccac atcttgcgaa tatatgtgta       5400
gaaactgccg gaaatcgtcg tggtattcac tccagagcgt tgaaaacgtt tcagtttgct       5460
catggaaaac ggtgtaacaa gggtgaacac tatcccatat caccagctca ccgtctttca       5520
ttgccatacg aaattccgga tgagcattca tcaggcgggc aagaatgtga ataaaggccg       5580
gataaaactt gtgcttattt ttctttacgg tctttaaaaa ggccgtaata tccagctgaa       5640
cggtctggtt ataggtacat tgagcaactg actgaaatgc ctcaaaatgt tctttacgat       5700
gccattggga tatatcaacg gtggtatatc cagtgatttt tttctccatt ttagcttcct       5760
tagctcctga aaatctcgat aactcaaaaa atacgcccgg tagtgatctt atttcattat       5820
ggtgaaagtt ggaacctctt acgtgccgat caacgtctca ttttcgccag atatc          5875
```

```
                                                        SEQ ID NO: 7
gacgtcttga cagctagctc agtcctaggg attgtgctag caggtttaat cgaattgacg        60
tctttacggc tagctcagtc ctaggtacta tgctagcagg tttaatcgaa ttcaaaagat       120
cttttaagaa ggagatatac atatgattac tcatggttgt tatacccgga cccggcacaa       180
gcataagcta aaaaaaacat tgattatgct tagtgctggt ttaggattgt tttttttatgt      240 taatcagaac tcatttgcaa atggtgaaaa ttattttaaa ttgggttcgg attcaaaact       300
gttaactcat gatagctatc agaatcgcct tttttatacg ttgaaaactg gtgaaactgt       360
tgccgatctt tctaaatcgc aagatattaa tttatcgacg atttggtcgt tgaataagca       420
tttatacagt tctgaaagcg aaatgatgaa ggccgcgcct ggtcagcaga tcattttgcc       480
actcaaaaaa cttcccttg aatacagtgc actaccactt ttaggttcgg cacctcttgt        540
tgctgcgggt ggtgttgctg gtcacacgaa taaactgact aaaatgtccc cggacgtgac       600
caaaagcaac atgaccgatg acaaggcatt aaattatgcg gcacaacagg cggcgagtct       660
cggtagccag cttcagtcgc gatctctgaa cggcgattac gcgaaagata ccgctcttgg       720
tatcgctggt aaccaggctt cgtcacagtt gcaggcctgg ttacaacatt atggaacggc       780
agaggttaat ctgcaaagtg gtaataactt tgacggtagt tcactggact tcttattacc       840
gttctatgat tccgaaaaaa tgctggcatt tggtcaggtc ggagcgcgtt acattgactc       900
ccgctttacg gcaaatttag gtgcgggtca gcgttttttc cttcctgcaa acatgttggg       960
ctataacgtc ttcattgatc aggattttttc tggtgataat acccgtttag gtattggtgg     1020
cgaatactgg cgagactatt tcaaaagtag cgttaacggc tatttccgca tgagcggctg      1080
gcatgagtca tacaataaga aagactatga tgagcgccca gcaaatggct cgatatccg       1140 tttttaatggc tatctaccgt catatccggc attaggcgcc aagctgatat atgagcagta     1200
ttatggtgat aatgttgctt gtttaattc tgataagctg caatcgaatc ctggtgcggc       1260
gaccgttggt gtaaactata ctccgattcc tctggtgacg atggggatcg attaccgtca     1320
tggtacgggt aatgaaaatg atctcctta ctcaatgcag ttccgttatc agtttgataa       1380
atcgtggtct cagcaaattg aaccacagta tgttaacgag ttaagaacat tatcaggcag      1440
ccgttacgat ctggttcagc gtaataacaa tattattctg gagtacaaga agcaggatat      1500
tctttctctg aatattccgc atgatattaa tggtactgaa cacagtacgc agaagattca      1560
gttgatcgtt aagagcaaat acggtctgga tcgtatcgtc tgggatgata gtgcattacg      1620
```

-continued

```
cagtcagggc ggtcagattc agcatagcgg aagccaaagc gcacaagact accaggctat     1680
tttgcctgct tatgtgcaag gtggcagcaa tatttataaa gtgacggctc gcgcctatga     1740
ccgtaatggc aatagctcta acaatgtaca gcttactatt accgttctgt cgaatggtca     1800
agttgtcgac caggttgggg taacggactt tacggcggat aagacttcgg ctaaagcgga     1860
taacgccgat accattactt ataccgcgac ggtgaaaaag aatggggtag ctcaggctaa     1920
tgtccctgtt tcatttaata ttgtttcagg aactgcaact cttggggcaa atagtgccaa     1980
aacggatgct aacggtaagg caaccgtaac gttgaagtcg agtacgccag gacaggtcgt     2040
cgtgtctgct aaaaccgcgg agatgacttc agcacttaat gccagtgcgg ttatattttt     2100
tgatggtgcg cccgggaagc ttgaaaacct gtacttccaa ggtacgcgtc aggtgcagct     2160
gcaggaaagc ggtggtggtc tggtgcaggc cggtggtagc ctgcgtctga gctgtgccgc     2220
cagcggtcgt acctttagcg aatatgccat gggttggttt cgtcaggccc gggtaaaga     2280 acgtgaattt gtggccacca ttagctggag cggtggtagc acctattata ccgatagcgt     2340
gaaaggtcgt tttaccatta gccgtgataa tgccaaaaat accgtgtatc tgcagatgaa     2400
tagcctgaaa ccggatgata ccgccgtgta ttattgtgcc gccgccggtc tgggtaccgt     2460
ggtgagcgaa tgggattatg attatgatta ttggggtcag ggtacccagg tgaccgtgag     2520
cagcggtagc ggatccgaaa acctgtactt ccaaggtgac tacaaggacg atgacgataa     2580
gtggagccat ccgcagtttg agaaatctag ataaggtacc actcgagtaa ggatctccag     2640
gcatcaaata aaacgaaagg ctcagtcgaa agactgggcc tttcgtttta tctgttgttt     2700
gtcggtgaac gctctctact agagtcacac tggctcacct tcgggtgggc ctttctgcgt     2760
ttatacctag ggtacgggt tttgctgccccg caaacgggct gttctggtgt tgctagtttg     2820
ttatcagaat cgcagatccg gcttcagccg gtttgccggc tgaaagcgct atttcttcca     2880
gaattgccat gatttttttcc ccacgggagg cgtcactggc tcccgtgttg tcggcagctt     2940
tgattcgata agcagcatcg cctgtttcag gctgtctatg tgtgactgtt gagctgtaac     3000
aagttgtctc aggtgttcaa tttcatgttc tagttgcttt gttttactgg tttcacctgt     3060
tctattaggt gttacatgct gttcatctgt tacattgtcg atctgttcat ggtgaacagc     3120
tttgaatgca ccaaaaactc gtaaaagctc tgatgtatct atcttttttta caccgttttc     3180 atctgtgcat atggacagtt ttcccttttga tatgtaacgg tgaacagttg ttctactttt     3240
gtttgttagt cttgatgctt cactgataga tacaagagcc ataagaacct cagatccttc     3300
cgtatttagc cagtatgttc tctagtgtgg ttcgttgttt ttgcgtgagc catgagaacg     3360
aaccattgag atcatactta ctttgcatgt cactcaaaaa ttttgcctca aaactggtga     3420
gctgaatttt tgcagttaaa gcatcgtgta gtgtttttct tagtccgtta tgtaggtagg     3480
aatctgatgt aatggttgtt ggtattttgt caccattcat ttttatctgg ttgttctcaa     3540
gttcggttac gagatccatt tgtctatcta gttcaacttg gaaaatcaac gtatcagtcg     3600
ggcggcctcg cttatcaacc accaatttca tattgctgta agtgtttaaa tctttactta     3660
ttggtttcaa aacccattgg ttaagccttt taaactcatg gtagttattt tcaagcatta     3720
acatgaactt aaattcatca aggctaatct ctatatttgc cttgtgagtt ttctttttgtg     3780 ttagttcttt taataaccac tcataaatcc tcatagagta tttgtttttca aaagacttaa     3840 catgttccag attatatttt atgaattttt ttaactggaa aagataaggc aatatctctt     3900
cactaaaaac taattctaat ttttcgcttg agaacttggc atagtttgtc cactggaaaa     3960
tctcaaagcc tttaaccaaa ggattcctga tttccacagt tctcgtcatc agctctctgg     4020
```

-continued

```
ttgctttagc taatacacca taagcatttt ccctactgat gttcatcatc tgagcgtatt      4080
ggttataagt gaacgatacc gtccgttctt tccttgtagg gttttcaatc gtggggttga      4140
gtagtgccac acagcataaa attagcttgg tttcatgctc cgttaagtca tagcgactaa      4200
tcgctagttc atttgctttg aaaacaacta attcagacat acatctcaat tggtctaggt      4260
gattttaatc actataccaa ttgagatggg ctagtcaatg ataattacta gtcctttttcc     4320 cgggtgatct gggtatctgt aaattctgct agacctttgc tggaaaactt gtaaattctg      4380
ctagaccctc tgtaaattcc gctagacctt tgtgtgtttt ttttgtttat attcaagtgg      4440
ttataattta tagaataaag aaagaataaa aaaagataaa aagaatagat cccagccctg      4500
tgtataactc actactttag tcagttccgc agtattacaa aaggatgtcg caaacgctgt      4560
ttgctcctct acaaaacaga ccttaaaacc ctaaaggctt aagtagcacc ctcgcaagct      4620
cgggcaaatc gctgaatatt cctttgtct ccgaccatca ggcacctgag tcgctgtctt       4680
tttcgtgaca ttcagttcgc tgcgctcacg gctctggcag tgaatggggg taaatggcac      4740
tacaggcgcc ttttatggat tcatgcaagg aaactaccca taatacaaga aaagcccgtc      4800
acgggcttct cagggcgttt tatggcgggt ctgctatgtg gtgctatctg actttttgct      4860
gttcagcagt tcctgccctc tgattttcca gtctgaccac ttcggattat cccgtgacag      4920
gtcattcaga ctggctaatg cacccagtaa ggcagcggta tcatcaacag gcttacccgt      4980
cttactgtcc ctagtgcttg gattctcacc aataaaaaac gcccggcggc aaccgagcgt      5040
tctgaacaaa tccagatgga gttctgaggt cattactgga tctatcaaca ggagtccaag      5100
cgagctcgat atcaaattac gccccgccct gccactcatc gcagtactgt tgtaattcat      5160
taagcattct gccgacatgg aagccatcac aaacggcatg atgaacctga atcgccagcg      5220
gcatcagcac cttgtcgcct tgcgtataat atttgcccat ggtgaaaacg ggggcgaaga      5280
agttgtccat attggccacg tttaaatcaa aactggtgaa actcacccag ggattggctg      5340
agacgaaaaa catattctca ataaacccctt tagggaaata ggccaggttt tcaccgtaac      5400
acgccacatc ttgcgaatat atgtgtagaa actgccggaa atcgtcgtgg tattcactcc      5460
agagcgatga aaacgtttca gtttgctcat ggaaaacggt gtaacaaggg tgaacactat      5520
cccatatcac cagctcaccg tctttcattg ccatacgaaa ttccggatga gcattcatca      5580
ggcgggcaag aatgtgaata aaggccggat aaaacttgtg cttatttttc tttacggtct      5640
ttaaaaaggc cgtaatatcc agctgaacgg tctggttata ggtacattga gcaactgact      5700
gaaatgcctc aaaatgttct ttacgatgcc attgggatat atcaacggtg gtatatccag      5760 tgatttttttt ctccatttta gcttccttag ctcctgaaaa tctcgataac tcaaaaaata     5820
cgcccggtag tgatcttatt tcattatggt gaaagttgga acctcttacg tgccgatcaa      5880
cgtctcattt tcgccagata tc                                              5902
```

SEQ ID NO: 8

```
gacgtcttga cagctagctc agtcctaggg attgtgctag caggtttaat cgaattgacg        60
tctttacggc tagctcagtc ctaggtacta tgctagcagg tttaatcgaa ttcaaaagat       120
cttttaagaa ggagatatac atatgaaagc aaccaagctg gttctgggtg ccgtgattct       180
gggcagtacc ctgttagcag gttgttctag caatgccaaa atcgaccaag gcatcaacaa       240
caatggcccg acccacgaaa accagctggg tgccggtgcc tttggtggtt atcaggtgaa       300
cccgtacgtg ggctttgaaa tgggctatga ttggctgggc cgcatgccgt acaaaggcag       360
tgtggagaac ggcgcctata aagcacaggg cgtgcagctg acagcaaaac tgggctaccc       420
tattaccgac gacctggaca tctacacacg cttaggcggc atggtgtggc gcgccgatac       480
```

31

32

-continued

```
caagagcaac gtgtacggca agaaccacga taccggcgtg agtccggtgt ttgccggcgg      540
tgtggagtat gcaatcaccc cggaaattgc cacacgtaag cttgaaaacc tgtacttcca      600
aggtacgcgt caggtgcagc tggtggaaac cggcggcggc ctggtgcagc cgggcggcag      660
cctgcgcctg agctgcgcgg cgagcggctt tacctttagc agcgtgtata tgaactgggt      720
gcgccaggcg ccgggcaaag gcccggaatg ggtgagccgc attagcccga acagcggcaa      780
cattggctat accgatagcg tgaaaggccg ctttaccatt agccgcgata cgcgaaaaa      840 caccctgtat ctgcagatga caacctgaa accggaagat accgcgctgt attattgcgc      900
gattggcctg aacctgagca gcagcagcgt gcgcggccag ggcacccagg tgaccgtgag      960
cagcggatcc gaaaacctgt acttccaagg tgactacaag gacgatgacg ataagtggag     1020
ccatccgcag tttgagaaat ctagataagg taccactcga gtaaggatct ccaggcatca     1080
aataaaacga aaggctcagt cgaaagactg ggcctttcgt tttatctgtt gtttgtcggt     1140
gaacgctctc tactagagtc acactggctc accttcgggt gggcctttct gcgtttatac     1200
ctagggtacg ggttttgctg cccgcaaacg ggctgttctg gtgttgctag tttgttatca     1260
gaatcgcaga tccggcttca gccggtttgc cggctgaaag cgctatttct tccagaattg     1320
ccatgatttt ttccccacgg gaggcgtcac tggctcccgt gttgtcggca gctttgattc     1380
gataagcagc atcgcctgtt tcaggctgtc tatgtgtgac tgttgagctg taacaagttg     1440
tctcaggtgt tcaatttcat gttctagttg ctttgtttta ctggtttcac ctgttctatt     1500
aggtgttaca tgctgttcat ctgttacatt gtcgatctgt tcatggtgaa cagctttgaa     1560
tgcaccaaaa actcgtaaaa gctctgatgt atctatcttt tttacaccgt tttcatctgt     1620
gcatatggac agtttttccct ttgatatgta acggtgaaca gttgttctac ttttgtttgt     1680
tagtcttgat gcttcactga tagatacaag agccataaga acctcagatc cttccgtatt     1740
tagccagtat gttctctagt gtggttcgtt gtttttgcgt gagccatgag aacgaaccat     1800
tgagatcata cttactttgc atgtcactca aaaattttgc ctcaaaactg gtgagctgaa     1860
tttttgcagt taaagcatcg tgtagtgttt ttcttagtcc gttatgtagg taggaatctg     1920
atgtaatggt tgttggtatt ttgtcaccat tcatttttat ctggttgttc tcaagttcgg     1980
ttacgagatc catttgtcta tctagttcaa cttggaaaat caacgtatca gtcgggcggc     2040
ctcgcttatc aaccaccaat ttcatattgc tgtaagtgtt taaatcttta cttattggtt     2100
tcaaaaccca ttggttaagc ctttttaaact catggtagtt attttcaagc attaacatga     2160
acttaaattc atcaaggcta atctctatat ttgccttgtg agttttcttt tgtgttagtt     2220
cttttaataa ccactcataa atcctcatag agtatttgtt ttcaaaagac ttaacatgtt     2280
ccagattata ttttatgaat ttttttaact ggaaaagata aggcaatatc tcttcactaa     2340
aaactaattc taatttttcg cttgagaact tggcatagtt tgtccactgg aaaatctcaa     2400
agcctttaac caaaggattc ctgatttcca cagttctcgt catcagctct ctggttgctt     2460
tagctaatac accataagca ttttccctac tgatgttcat catctgagcg tattggttat     2520
aagtgaacga taccgtccgt tctttccttg tagggttttc aatcgtgggg ttgagtagtg     2580
ccacacagca taaaattagc ttggtttcat gctccgttaa gtcatagcga ctaatcgcta     2640
gttcatttgc tttgaaaaca actaattcag acatacatct caattggtct aggtgatttt     2700
aatcactata ccaattgaga tgggctagtc aatgataatt actagtcctt ttcccgggtg     2760
atctgggtat ctgtaaattc tgctagacct ttgctggaaa acttgtaaat tctgctagac     2820
cctctgtaaa ttccgctaga cctttgtgtg ttttttttgt ttatattcaa gtggttataa     2880
tttatagaat aaagaaagaa taaaaaaaga taaaaagaat agatcccagc cctgtgtata     2940
```

-continued

```
actcactact ttagtcagtt ccgcagtatt acaaaaggat gtcgcaaacg ctgtttgctc      3000
ctctacaaaa cagaccttaa aaccctaaag gcttaagtag caccctcgca agctcgggca      3060
aatcgctgaa tattcctttt gtctccgacc atcaggcacc tgagtcgctg tcttttttcgt     3120 gacattcagt tcgctgcgct cacggctctg gcagtgaatg ggggtaaatg gcactacagg      3180
cgccttttat ggattcatgc aaggaaacta cccataatac aagaaaagcc cgtcacgggc      3240
ttctcagggc gttttatggc gggtctgcta tgtggtgcta tctgactttt tgctgttcag      3300
cagttcctgc cctctgattt tccagtctga ccacttcgga ttatcccgtg acaggtcatt      3360
cagactggct aatgcaccca gtaaggcagc ggtatcatca acaggcttac ccgtcttact      3420
gtccctagtg cttggattct caccaataaa aaacgcccgg cggcaaccga gcgttctgaa      3480
caaatccaga tggagttctg aggtcattac tggatctatc aacaggagtc caagcgagct      3540
cgatatcaaa ttacgccccg ccctgccact catcgcagta ctgttgtaat tcattaagca      3600
ttctgccgac atggaagcca tcacaaacg catgatgaac ctgaatcgcc agcggcatca      3660
gcaccttgtc gccttgcgta taatatttgc ccatggtgaa aacgggggcg aagaagttgt      3720
ccatattggc cacgtttaaa tcaaaactgg tgaaactcac ccagggattg gctgagacga      3780
aaaacatatt ctcaataaac cctttaggga aataggccag gttttcaccg taacacgcca      3840
catcttgcga atatatgtgt agaaactgcc ggaaatcgtc gtggtattca ctccagagcg      3900
atgaaaacgt ttcagtttgc tcatggaaaa cggtgtaaca agggtgaaca ctatcccata      3960
tcaccagctc accgtctttc attgccatac gaaattccgg atgagcattc atcaggcggg      4020
caagaatgtg aataaaggcc ggataaaact tgtgcttatt tttctttacg gtctttaaaa      4080
aggccgtaat atccagctga acggtctggt tataggtaca ttgagcaact gactgaaatg      4140
cctcaaaatg ttctttacga tgccattggg atatatcaac ggtggtatat ccagtgattt      4200
ttttctccat tttagcttcc ttagctcctg aaaatctcga taactcaaaa aatacgcccg      4260
gtagtgatct tatttcatta tggtgaaagt tggaacctct tacgtgccga tcaacgtctc      4320
attttcgcca gatatc                                                      4336
```

SEQ ID NO: 9
```
gacgtcttga cagctagctc agtcctaggg attgtgctag caggtttaat cgaattgacg       60
tctttacggc tagctcagtc ctaggtacta tgctagcagg tttaatcgaa ttcaaaagat      120
cttttaagaa ggagatatac atatgaaagc aaccaagctg gttctgggtg ccgtgattct      180
gggcagtacc ctgttagcag gttgttctag caatgccaaa atcgaccaag gcatcaacaa      240
caatggcccg acccacgaaa accagctggg tgccggtgcc tttggtggtt atcaggtgaa      300
cccgtacgtg ggctttgaaa tgggctatga ttggctgggc cgcatgccgt acaaaggcag      360
tgtggagaac ggcgcctata aagcacaggg cgtgcagctg acagcaaaac tgggctaccc      420
tattaccgac gacctggaca tctacacacg cttaggcggc atggtgtggc gcgccgatac      480
caagagcaac gtgtacggca agaaccacga taccggcgtg agtccggtgt ttgccggcgg      540
tgtggagtat gcaatcaccc cggaaattgc cacacgtaag cttgaaaacc tgtacttcca      600
aggtacgcgt caggtgcagc tgcaggaaag cggtggtggt ctggtgcagg ccggtggtag      660
cctgcgtctg agctgtgccg ccagcggtcg tacctttagc gaatatgcca tgggttggtt      720
tcgtcaggcc ccgggtaaag aacgtgaatt tgtggccacc attagctgga gcggtggtag      780
cacctattat accgatagcg tgaaaggtcg ttttaccatt agccgtgata atgccaaaaa      840
taccgtgtat ctgcagatga atagcctgaa accggatgat accgccgtgt attattgtgc      900
cgccgccggt ctgggtaccg tggtgagcga atgggattat gattatgatt attggggtca      960
```

-continued

```
gggtacccag gtgaccgtga gcagcggtag cggatccgaa aacctgtact tccaaggtga       1020
ctacaaggac gatgacgata agtggagcca tccgcagttt gagaaatcta gataaggtac       1080
cactcgagta aggatctcca ggcatcaaat aaaacgaaag gctcagtcga aagactgggc       1140
ctttcgtttt atctgttgtt tgtcggtgaa cgctctctac tagagtcaca ctggctcacc       1200
ttcgggtggg cctttctgcg tttataccta gggtacgggt tttgctgccc gcaaacgggc       1260
tgttctggtg ttgctagttt gttatcagaa tcgcagatcc ggcttcagcc ggtttgccgg       1320
ctgaaagcgc tatttcttcc agaattgcca tgattttttc cccacgggag gcgtcactgg       1380
ctcccgtgtt gtcggcagct ttgattcgat aagcagcatc gcctgtttca ggctgtctat       1440
gtgtgactgt tgagctgtaa caagttgtct caggtgttca atttcatgtt ctagttgctt       1500
tgttttactg gtttcacctg ttctattagg tgttacatgc tgttcatctg ttacattgtc       1560
gatctgttca tggtgaacag ctttgaatgc accaaaaact cgtaaaagct ctgatgtatc       1620
tatctttttt acaccgtttt catctgtgca tatggacagt tttccctttg atatgtaacg       1680
gtgaacagtt gttctacttt tgtttgttag tcttgatgct tcactgatag atacaagagc       1740
cataagaacc tcagatcctt ccgtatttag ccagtatgtt ctctagtgtg gttcgttgtt       1800
tttgcgtgag ccatgagaac gaaccattga gatcatactt actttgcatg tcactcaaaa       1860
attttgcctc aaaactggtg agctgaattt ttgcagttaa agcatcgtgt agtgtttttc       1920
ttagtccgtt atgtaggtag gaatctgatg taatggttgt tggtattttg tcaccattca       1980
tttttatctg gttgttctca agttcggtta cgagatccat ttgtctatct agttcaactt       2040
ggaaaatcaa cgtatcagtc gggcggcctc gcttatcaac caccaatttc atattgctgt       2100
aagtgtttaa atctttactt attggtttca aaacccattg gttaagcctt ttaaactcat       2160
ggtagttatt ttcaagcatt aacatgaact taaattcatc aaggctaatc tctatatttg       2220
ccttgtgagt tttctttgt gttagttctt ttaataacca ctcataaatc ctcatagagt       2280
atttgttttc aaaagactta acatgttcca gattatattt tatgaatttt tttaactgga       2340
aaagataagg caatatctct tcactaaaaa ctaattctaa ttttttcgctt gagaacttgg       2400 catagtttgt ccactggaaa atctcaaagc ctttaaccaa aggattcctg atttccacag       2460
ttctcgtcat cagctctctg gttgctttag ctaatacacc ataagcattt tccctactga       2520
tgttcatcat ctgagcgtat tggttataag tgaacgatac cgtccgttct ttccttgtag       2580
ggttttcaat cgtgggggttg agtagtgcca cacagcataa aattagcttg gtttcatgct       2640
ccgttaagtc atagcgacta atcgctagtt catttgcttt gaaaacaact aattcagaca       2700
tacatctcaa ttggtctagg tgattttaat cactatacca attgagatgg gctagtcaat       2760
gataattact agtccttttc ccgggtgatc tgggtatctg taaattctgc tagacctttg       2820
ctggaaaact tgtaaattct gctagaccct ctgtaaattc cgctagacct ttgtgtgttt       2880
tttttgttta tattcaagtg gttataattt atagaataaa gaaagaataa aaaaagataa       2940
aaagaataga tcccagccct gtgtataact cactacttta gtcagttccg cagtattaca       3000
aaaggatgtc gcaaacgctg tttgctcctc tacaaaacag accttaaaac cctaaaggct       3060
taagtagcac cctcgcaagc tcgggcaaat cgctgaatat tccttttgtc tccgaccatc       3120
aggcacctga gtcgctgtct ttttcgtgac attcagttcg ctgcgctcac ggctctggca       3180
gtgaatgggg gtaaatggca ctacaggcgc ctttttatgga ttcatgcaag gaaactaccc       3240
ataatacaag aaaagcccgt cacgggcttc tcagggcgtt ttatggcggg tctgctatgt       3300
ggtgctatct gacttttttgc tgttcagcag ttcctgccct ctgattttcc agtctgacca       3360
```

-continued

```
cttcggatta tcccgtgaca ggtcattcag actggctaat gcaccagta aggcagcggt    3420 atcatcaaca ggcttacccg tcttactgtc cctagtgctt ggattctcac caataaaaaa    3480
cgcccggcgg caaccgagcg ttctgaacaa atccagatgg agttctgagg tcattactgg    3540
atctatcaac aggagtccaa gcgagctcga tatcaaatta cgccccgccc tgccactcat    3600
cgcagtactg ttgtaattca ttaagcattc tgccgacatg gaagccatca caaacggcat    3660
gatgaacctg aatcgccagc ggcatcagca ccttgtcgcc ttgcgtataa tatttgccca    3720
tggtgaaaac gggggcgaag aagttgtcca tattggccac gtttaaatca aaactggtga    3780
aactcaccca gggattggct gagacgaaaa acatattctc aataaaccct ttagggaaat    3840
aggccaggtt ttcaccgtaa cacgccacat cttgcgaata tatgtgtaga aactgccgga    3900
aatcgtcgtg gtattcactc cagagcgatg aaaacgtttc agtttgctca tggaaaacgg    3960
tgtaacaagg gtgaacacta tcccatatca ccagctcacc gtctttcatt gccatacgaa    4020
attccggatg agcattcatc aggcgggcaa gaatgtgaat aaaggccgga taaaacttgt    4080
gcttattttt ctttacggtc tttaaaaagg ccgtaatatc cagctgaacg gtctggttat    4140
aggtacattg agcaactgac tgaaatgcct caaaatgttc tttacgatgc cattgggata    4200
tatcaacggt ggtatatcca gtgatttttt tctccatttt agcttcctta gctcctgaaa    4260
atctcgataa ctcaaaaaat acgcccggta gtgatcttat ttcattatgg tgaaagttgg    4320
aacctcttac gtgccgatca acgtctcatt ttcgccagat atc                      4363

SEQ ID NO: 10
gacgtcttga cagctagctc agtcctaggg attgtgctag caggtttaat cgaattgacg    60
tctttacggc tagctcagtc ctaggtacta tgctagcagg tttaatcgaa ttcaaaagat    120
cttttaagaa ggagatatac atatgaaagc caccaaactg gttctgggtg cagttattct    180
gggtagcacc ctgctggcag gttgtagcag caatgcaaaa attgatcagg gcattaataa    240
caacggtccg acacatgaaa tcagttagg tgccggtgca tttggtggtt atcaggttaa    300
tccgtatgtg ggttttgaaa tgggttatga ttggctgggt cgtatgccgt ataaaggtag    360
cgttgaaaat ggtgcatata aagcacaggg tgttcagctg accgcaaaac tgggttatcc    420
gattaccgat gatctggata tctatacccg tttaggtggt atggtttggc gtgcagatac    480
caaaagcaat gtgtatggca aaaatcatga taccggtgtt agtccggttt ttgccggtgg    540
tgttgaatat gcaattacac cggaaattgc aacccgcaaa ctggaaaatc tgtattttca    600
gggcacccgt caggttcagc tgcaagaaag cggtggtggt ctggttcagg caggcggtag    660
cctgcgtctg agctgtgcag caagcggtcg tacctttagc gaatatgcca tgggttggtt    720
tcgtcaggca ccgggtaaag aacgtgaatt tgttgcaacc attagctggt ctggtggtag    780
cacctattat accgatagcg ttaaaggtcg ttttaccatt agccgtgata atgccaaaaa    840
taccgtttac ctgcagatga atagcctgaa accggatgat accgcagtgt attattgtgc    900
agcagcaggt ctgggtacag ttgttagcga gtgggattat gattatgact attgggggtca    960 gggtacacag gttaccgtta gcagcggtag cggtagtgag aacctgtatt ccaaggtga    1020 ttataaagat gacgatgata gtggtcccca tccgcagttt gaaaaaagcc gttaaggtac    1080
cactcgagta aggatctcca ggcatcaaat aaaacgaaag gctcagtcga agactgggc    1140 ctttcgtttt atctgttgtt tgtcggtgaa cgctctctac tagagtcaca ctggctcacc    1200
ttcgggtggg cctttctgcg tttataccta gggtacgggt tttgctgccc gcaaacgggc    1260
tgttctggtg ttgctagttt gttatcagaa tcgcagatcc ggcttcagcc ggtttgccgg    1320
ctgaaagcgc tatttcttcc agaattgcca tgatttttt cccacgggag gcgtcactgg    1380
```

```
ctcccgtgtt gtcggcagct ttgattcgat aagcagcatc gcctgtttca ggctgtctat    1440
gtgtgactgt tgagctgtaa caagttgtct caggtgttca atttcatgtt ctagttgctt    1500
tgttttactg gtttcacctg ttctattagg tgttacatgc tgttcatctg ttacattgtc    1560
gatctgttca tggtgaacag ctttgaatgc accaaaaact cgtaaaagct ctgatgtatc    1620
tatctttttt acaccgtttt catctgtgca tatggacagt tttccctttg atatgtaacg    1680
gtgaacagtt gttctacttt tgtttgttag tcttgatgct tcactgatag atacaagagc    1740
cataagaacc tcagatcctt ccgtatttag ccagtatgtt ctctagtgtg gttcgttgtt    1800
tttgcgtgag ccatgagaac gaaccattga gatcatactt actttgcatg tcactcaaaa    1860
attttgcctc aaaactggtg agctgaattt ttgcagttaa agcatcgtgt agtgtttttc    1920
ttagtccgtt atgtaggtag gaatctgatg taatggttgt tggtattttg tcaccattca    1980
tttttatctg gttgttctca agttcggtta cgagatccat ttgtctatct agttcaactt    2040
ggaaaatcaa cgtatcagtc gggcggcctc gcttatcaac caccaatttc atattgctgt    2100
aagtgtttaa atctttactt attggtttca aaacccattg gttaagcctt ttaaactcat    2160
ggtagttatt ttcaagcatt aacatgaact aaattcatc aaggctaatc tctatatttg    2220
ccttgtgagt tttcttttgt gttagttctt ttaataacca ctcataaatc ctcatagagt    2280
atttgttttc aaaagactta acatgttcca gattatattt tatgaatttt tttaactgga    2340
aaagataagg caatatctct tcactaaaaa ctaattctaa tttttcgctt gagaacttgg    2400
catagtttgt ccactggaaa atctcaaagc ctttaaccaa aggattcctg atttccacag    2460
ttctcgtcat cagctctctg gttgctttag ctaatacacc ataagcattt tccctactga    2520
tgttcatcat ctgagcgtat tggttataag tgaacgatac cgtccgttct ttccttgtag    2580
ggttttcaat cgtggggttg agtagtgcca cacagcataa aattagcttg gtttcatgct    2640
ccgttaagtc atagcgacta atcgctagtt catttgcttt gaaaacaact aattcagaca    2700
tacatctcaa ttggtctagg tgattttaat cactatacca attgagatgg gctagtcaat    2760
gataattact agtccttttc ccgggtgatc tgggtatctg taaattctgc tagacctttg    2820
ctggaaaact tgtaaattct gctagaccct ctgtaaattc cgctagacct ttgtgtgttt    2880
tttttgttta tattcaagtg gttataattt atagaataaa gaaagaataa aaaaagataa    2940
aaagaataga tcccagccct gtgtataact cactacttta gtcagttccg cagtattaca    3000
aaaggatgtc gcaaacgctg tttgctcctc tacaaaacag accttaaaac cctaaaggct    3060
taagtagcac cctcgcaagc tcgggcaaat cgctgaatat tccttttgtc tccgaccatc    3120
aggcacctga gtcgctgtct ttttcgtgac attcagttcg ctgcgctcac ggctctggca    3180
gtgaatgggg gtaaatggca ctacaggcgc cttttatgga ttcatgcaag gaaactaccc    3240
ataatacaag aaaagcccgt cacgggcttc tcagggcgtt ttatggcggg tctgctatgt    3300
ggtgctatct gacttttttgc tgttcagcag ttcctgccct ctgattttcc agtctgacca    3360
cttcggatta tcccgtgaca ggtcattcag actggctaat gcacccagta aggcagcggt    3420
atcatcaaca ggcttacccg tcttactgtc cctagtgctt ggattctcac caataaaaaa    3480
cgcccggcgg caaccgagcg ttctgaacaa atccagatgg agttctgagg tcattactgg    3540
atctatcaac aggagtccaa gcgagctcga tatcaaatta cgccccgccc tgccactcat    3600
cgcagtactg ttgtaattca ttaagcattc tgccgacatg gaagccatca caaacggcat    3660
gatgaacctg aatcgccagc ggcatcagca ccttgtcgcc ttgcgtataa tatttgccca    3720
tggtgaaaac gggggcgaag aagttgtcca tattggccac gtttaaatca aaactggtga    3780
aactcaccca gggattggct gagacgaaaa acatattctc aataaaccct ttagggaaat    3840
```

-continued

```
aggccaggtt ttcaccgtaa cacgccacat cttgcgaata tatgtgtaga aactgccgga     3900
aatcgtcgtg gtattcactc cagagcgatg aaaacgtttc agtttgctca tggaaaacgg     3960
tgtaacaagg gtgaacacta tcccatatca ccagctcacc gtctttcatt gccatacgaa     4020
attccggatg agcattcatc aggcgggcaa gaatgtgaat aaaggccgga taaaacttgt     4080 gcttatttt  ctttacggtc tttaaaaagg ccgtaatatc cagctgaacg gtctggttat     4140
aggtacattg agcaactgac tgaaatgcct caaaatgttc tttacgatgc cattgggata     4200
tatcaacggt ggtatatcca gtgattttt  tctccatttt agcttcctta gctcctgaaa     4260
atctcgataa ctcaaaaaat acgcccggta gtgatcttat ttcattatgg tgaaagttgg     4320
aacctcttac gtgccgatca acgtctcatt ttcgccagat atc                      4363

SEQ ID NO: 11
gacgtcttga cagctagctc agtcctaggg attgtgctag caggtttaat cgaattgacg        60
tctttacggc tagctcagtc ctaggtacta tgctagcagg tttaatcgaa ttcaaaagat       120
cttttaagaa ggagatatac atatgattac tcatggttgt tatacccgga cccggcacaa       180
gcataagcta aaaaaaacat tgattatgct tagtgctggt ttaggattgt ttttttatgt       240
taatcagaac tcatttgcaa atggtgaaaa ttattttaaa ttgggttcgg attcaaaact       300
gttaactcat gatagctatc agaatcgcct tttttatacg ttgaaaactg gtgaaactgt       360
tgccgatctt tctaaatcgc aagatattaa tttatcgacg atttggtcgt tgaataagca       420
tttatacagt tctgaaagcg aaatgatgaa ggccgcgcct ggtcagcaga tcattttgcc       480
actcaaaaaa cttccctttg aatacagtgc actaccactt ttaggttcgg cacctcttgt       540
tgctgcgggt ggtgttgctg gtcacacgaa taaactgact aaaaatgtccc cggacgtgac       600 caaaagcaac atgaccgatg acaaggcatt aaattatgcg gcacaacagg cggcgagtct       660
cggtagccag cttcagtcgc gatctctgaa cggcgattac gcgaaagata ccgctcttgg       720
tatcgctggt aaccaggctt cgtcacagtt gcaggcctgg ttacaacatt atggaacggc       780
agaggttaat ctgcaaagtg gtaataactt tgacggtagt tcactggact tcttattacc       840
gttctatgat tccgaaaaaa tgctggcatt tggtcaggtc ggagcgcgtt acattgactc       900
ccgctttacg gcaaatttag gtgcgggtca gcgttttttc cttcctgcaa acatgttggg       960
ctataacgtc ttcattgatc aggatttttc tggtgataat acccgtttag gtattggtgg      1020
cgaatactgg cgagactatt tcaaaagtag cgttaacggc tatttccgca tgagcggctg      1080
gcatgagtca tacaataaga aagactatga tgagcgccca gcaaatggct tcgatatccg      1140
ttttaatggc tatctaccgt catatccggc attaggcgcc aagctgatat atgagcagta      1200
ttatggtgat aatgttgctt tgtttaattc tgataagctg caatcgaatc ctggtgcggc      1260
gaccgttggt gtaaactata ctccgattcc tctggtgacg atggggatcg attaccgtca      1320
tggtacgggt aatgaaaatg atctccttta ctcaatgcag ttccgttatc agtttgataa      1380
atcgtggtct cagcaaattg aaccacagta tgttaacgag ttaagaacat tatcaggcag      1440
ccgttacgat ctggttcagc gtaataacaa tattattctg gagtacaaga agcaggatat      1500
tctttctctg aatattccgc atgatattaa tggtactgaa cacagtacgc agaagattca      1560
gttgatcgtt aagagcaaat acggtctgga tcgtatcgtc tgggatgata gtgcattacg      1620
cagtcagggc ggtcagattc agcatagcgg aagccaaagc gcacaagact accaggctat      1680
tttgcctgct tatgtgcaag gtggcagcaa tatttataaa gtgacggctc gcgcctatga      1740
ccgtaatggc aatagctcta acaatgtaca gcttactatt accgttctgt cgaatggtca      1800
agttgtcgac caggttgggg taacggactt tacggcggat aagacttcgg ctaaagcgga      1860
```

-continued

```
taacgccgat accattactt ataccgcgac ggtgaaaaag aatgggggtag ctcaggctaa      1920 tgtccctgtt tcatttaata ttgtttcagg aactgcaact cttgggggcaa atagtgccaa      1980 aacggatgct aacggtaagg caaccgtaac gttgaagtcg agtacgccag gacaggtcgt      2040
cgtgtctgct aaaaccgcgg agatgacttc agcacttaat gccagtgcgg ttatattttt      2100
tgatggtgcg cccgggaagc ttgtcgacgg agctcgataa tccggcaaaa aagggcaagg      2160
tgtcaccacc ctgccctttt tctttaaaac cgaaaagatt acttcgcgtt atgcaggctt      2220
cctcgctcac tgactcgctg cgctcggtcg ttcggctgcg gcgagcggta tcagctcact      2280
caaaggcggt aatctcgagt cgatccaaac tcgagtaagg atctccaggc atcaaataaa      2340
acgaaaggct cagtcgaaag actgggcctt tcgtttatc tgttgtttgt cggtgaacgc      2400
tctctactag agtcacactg gctcaccttc gggtgggcct ttctgcgttt atacctaggg      2460
tacgggtttt gctgcccgca aacgggctgt tctggtgttg ctagtttgtt atcagaatcg      2520
cagatccggc ttcagccggt ttgccggctg aaagcgctat ttcttccaga attgccatga      2580
ttttttcccc acgggaggcg tcactggctc ccgtgttgtc ggcagctttg attcgataag      2640
cagcatcgcc tgtttcaggc tgtctatgtg tgactgttga gctgtaacaa gttgtctcag      2700
gtgttcaatt tcatgttcta gttgctttgt tttactggtt tcacctgttc tattaggtgt      2760
tacatgctgt tcatctgtta cattgtcgat ctgttcatgg tgaacagctt tgaatgcacc      2820
aaaaactcgt aaaagctctg atgtatctat cttttttaca ccgttttcat ctgtgcatat      2880
ggacagtttt ccctttgata tgtaacggtg aacagttgtt ctactttgt ttgttagtct      2940 tgatgcttca ctgatagata caagagccat aagaacctca gatccttccg tatttagcca      3000
gtatgttctc tagtgtggtt cgttgttttt gcgtgagcca tgagaacgaa ccattgagat      3060
catacttact ttgcatgtca ctcaaaaatt ttgcctcaaa actggtgagc tgaattttg      3120 cagttaaagc atcgtgtagt gttttttctta gtccgttatg taggtaggaa tctgatgtaa      3180
tggttgttgg tattttgtca ccattcattt ttatctggtt gttctcaagt tcggttacga      3240
gatccatttg tctatctagt tcaacttgga aaatcaacgt atcagtcggg cggcctcgct      3300
tatcaaccac caatttcata ttgctgtaag tgtttaaatc tttacttatt ggtttcaaaa      3360
cccattggtt aagcctttta aactcatggt agttattttc aagcattaac atgaacttaa      3420
attcatcaag gctaatctct atatttgcct tgtgagtttt cttttgtgtt agttctttta      3480
ataaccactc ataaatcctc atagagtatt tgttttcaaa agacttaaca tgttccagat      3540 tatatttttat gaattttttt aactggaaaa gataaggcaa tatctcttca ctaaaaacta      3600
attctaattt ttcgcttgag aacttggcat agtttgtcca ctggaaaatc tcaaagcctt      3660
taaccaaagg attcctgatt tccacagttc tcgtcatcag ctctctggtt gctttagcta      3720
atacaccata agcattttcc ctactgatgt tcatcatctg agcgtattgg ttataagtga      3780
acgataccgt ccgttctttc cttgtagggt tttcaatcgt gggggttgagt agtgccacac      3840 agcataaaat tagcttggtt tcatgctccg ttaagtcata gcgactaatc gctagttcat      3900
ttgctttgaa aacaactaat tcagacatac atctcaattg gtctaggtga tttttaatcac      3960 tataccaatt gagatgggct agtcaatgat aattactagt cctttttcccg ggtgatctgg      4020 gtatctgtaa attctgctag acctttgctg gaaaacttgt aaattctgct agaccctctg      4080
taaattccgc tagacctttg tgtgtttttt ttgtttatat tcaagtggtt ataatttata      4140
gaataaagaa agaataaaaa aagataaaaa gaatagatcc cagccctgtg tataactcac      4200
tactttagtc agttccgcag tattacaaaa ggatgtcgca aacgctgttt gctcctctac      4260
```

-continued

```
aaaacagacc ttaaaaccct aaaggcttaa gtagcaccct cgcaagctcg ggcaaatcgc      4320
tgaatattcc ttttgtctcc gaccatcagg cacctgagtc gctgtctttt tcgtgacatt      4380
cagttcgctg cgctcacggc tctggcagtg aatgggggta aatggcacta caggcgcctt      4440
ttatggattc atgcaaggaa actacccata atacaagaaa agcccgtcac gggcttctca      4500
gggcgtttta tggcgggtct gctatgtggt gctatctgac tttttgctgt tcagcagttc      4560
ctgccctctg attttccagt ctgaccactt cggattatcc cgtgacaggt cattcagact      4620
ggctaatgca cccagtaagg cagcggtatc atcaacaggc ttacccgtct tactgtccct      4680
agtgcttgga ttctcaccaa taaaaaacgc ccggcggcaa ccgagcgttc tgaacaaatc      4740
cagatggagt tctgaggtca ttactggatc tatcaacagg agtccaagcg agctcgatat      4800
caaattacgc cccgccctgc cactcatcgc agtactgttg taattcatta agcattctgc      4860
cgacatggaa gccatcacaa acggcatgat gaacctgaat cgccagcggc atcagcacct      4920
tgtcgccttg cgtataatat ttgcccatgg tgaaaacggg ggcgaagaag ttgtccatat      4980
tggccacgtt taaatcaaaa ctggtgaaac tcacccaggg attggctgag acgaaaaaca      5040
tattctcaat aaacccttta gggaaatagg ccaggttttc accgtaacac gccacatctt      5100
gcgaatatat gtgtagaaac tgccggaaat cgtcgtggta ttcactccag agcgatgaaa      5160
acgtttcagt ttgctcatgg aaaacggtgt aacaagggtg aacactatcc catatcacca      5220
gctcaccgtc tttcattgcc atacgaaatt ccggatgagc attcatcagg cgggcaagaa      5280
tgtgaataaa ggccggataa aacttgtgct tattttttctt tacggtcttt aaaaaggccg      5340
taatatccag ctgaacggtc tggttatagg tacattgagc aactgactga aatgcctcaa      5400
aatgttcttt acgatgccat tgggatatat caacggtggt atatccagtg attttttttct      5460 ccattttagc ttccttagct cctgaaaatc tcgataactc aaaaaatacg cccggtagtg      5520
atcttatttc attatggtga aagttggaac ctcttacgtg ccgatcaacg tctcattttc      5580
gccagatatc                                                            5590
```

What is claimed is:

1. An engineered probiotic bacterium comprising a heterologous nucleic acid,
    wherein the heterologous nucleic acid comprises a nucleic acid sequence encoding an anti-spike glycoprotein nanobody of a coronavirus,
    wherein the heterologous nucleic acid is located in a plasmid selected from pNKLab001 having the nucleic acid sequence of SEQ ID NO: 5 or SEQ ID NO: 6, pNKLab002 having the nucleic acid sequence of SEQ ID NO: 7, pNKLab003 having the nucleic acid sequence of SEQ ID NO: 8, and pNKLab004 having the nucleic acid sequence of SEQ ID NO: 9 or SEQ ID NO: 10.

2. The engineered probiotic bacterium of claim 1, wherein the engineered probiotic bacterium is *Escherichia coli* Nissle 1917.

3. The engineered probiotic bacterium of claim 1, wherein the nucleic acid sequence encoding the anti-spike glycoprotein nanobody of the coronavirus is selected from SEQ ID NO: 1, SEQ ID NO: 2, SEQ ID NO: 3 and SEQ ID NO: 4.

4. The engineered probiotic bacterium of claim 1, wherein the anti-spike glycoprotein nanobody appears on a surface of the engineered probiotic bacterium.

5. The engineered probiotic bacterium of claim 1, wherein the plasmid further comprises a surface display signal.

6. The engineered probiotic bacterium of claim 5, wherein the surface display signal is selected from Intimin and Lpp-OmpA.

7. A pharmaceutical composition comprising the engineered probiotic bacterium of claim 1 and a pharmaceutically acceptable excipient.

8. A method for treating a disease caused by a coronavirus in a subject, the method comprising administering the engineered probiotic bacterium of claim 1 to the subject, wherein the engineered probiotic bacterium expresses the anti-spike glycoprotein nanobody of the coronavirus.

9. The method of claim 8, wherein the disease is selected from severe acute respiratory syndrome (SARS), Middle East Respiratory Syndrome (MERS), and Covid-19.

\* \* \* \* \*

SEQUENCE LISTING

<160> NUMBER OF SEQ ID NOS: 11

<210> SEQ ID NO 1
<211> LENGTH: 381
<212> TYPE: DNA
<213> ORGANISM: Artificial Sequence
<220> FEATURE:
<223> OTHER INFORMATION: Anti-spike glycoprotein nanobody of a
    coronavirus <400> SEQUENCE: 1
```
caggtgcagc tgcaggaaag cggtggtggt ctggtgcagg ccggtggtag cctgcgtctg       60
agctgtgccg ccagcggtcg tacctttagc gaatatgcca tgggttggtt tcgtcaggcc      120
ccgggtaaag aacgtgaatt tgtggccacc attagctgga gcggtggtag cacctattat      180
accgatagcg tgaaaggtcg tttttaccatt agccgtgata tgccaaaaa taccgtgtat      240 ctgcagatga atagcctgaa accggatgat accgccgtgt attattgtgc cgccgccggt      300
ctgggtaccg tggtgagcga atgggattat gattatgatt attggggtca gggtacccag      360
gtgaccgtga gcagcggtag c                                                381
```

<210> SEQ ID NO 2
<211> LENGTH: 429

```
<212> TYPE: DNA
<213> ORGANISM: Artificial Sequence
<220> FEATURE:
<223> OTHER INFORMATION: Anti-spike glycoprotein nanobody of a
      coronavirus

<400> SEQUENCE: 2
aagcttcatc accatcacca tcacggtggt ggtggtagcc aggtgcagct gcaggaaagc      60
ggtggtggtc tggtgcaggc cggtggtagc ctgcgtctga gctgtgccgc cagcggtcgt     120
acctttagcg aatatgccat gggttggttt cgtcaggccc cgggtaaaga acgtgaattt     180
gtggccacca ttagctggag cggtggtagc acctattata ccgatagcgt gaaaggtcgt     240
tttaccatta gccgtgataa tgccaaaaat accgtgtatc tgcagatgaa tagcctgaaa     300
ccggatgata ccgccgtgta ttattgtgcc gccgccggtc tgggtaccgt ggtgagcgaa     360
tgggattatg attatgatta ttggggtcag ggtacccagg tgaccgtgag cagcggtagc     420
taaaagctt                                                           429

<210> SEQ ID NO 3
<211> LENGTH: 354
<212> TYPE: DNA
<213> ORGANISM: Artificial Sequence
<220> FEATURE:
<223> OTHER INFORMATION: Anti-spike glycoprotein nanobody of a
      coronavirus

<400> SEQUENCE: 3
caggtgcagc tggtggaaac cggcggcggc ctggtgcagc cgggcggcag cctgcgcctg      60
agctgcgcgg cgagcggctt tacctttagc agcgtgtata tgaactgggt gcgccaggcg     120
ccgggcaaag cccggaatg ggtgagccgc attagcccga cagcggcaa cattggctat       180 accgatagcg tgaaaggccg ctttaccatt agccgcgata cgcgaaaaa caccctgtat       240 ctgcagatga caacctgaa accggaagat accgcgctgt attattgcgc gattggcctg       300
aacctgagca gcagcagcgt gcgcggccag ggcacccagg tgaccgtgag cagc           354

<210> SEQ ID NO 4
<211> LENGTH: 491
<212> TYPE: DNA
<213> ORGANISM: Artificial Sequence
<220> FEATURE:
<223> OTHER INFORMATION: Anti-spike glycoprotein nanobody of a
      coronavirus

<400> SEQUENCE: 4
aagcttgaaa acctgtactt ccaaggtgaa ttccaggtgc agctggtgga aaccggcggc      60
ggcctggtgc agccgggcgg cagcctgcgc ctgagctgcg cggcgagcgg ctttaccttt     120
agcagcgtgt atatgaactg ggtgcgccag gcgccgggca aaggcccgga tgggtgagc      180 cgcattagcc cgaacagcgg caacattggc tataccgata gcgtgaaagg ccgctttacc     240
attagccgcg ataacgcgaa aaacaccctg tatctgcaga tgaacaacct gaaaccggaa     300
gataccgcgc tgtattattg cgcgattggc ctgaacctga gcagcagcag cgtgcgcggc     360
caggccaccc aggtgaccgt gagcagcgga tccgaaaacc tgtacttcca aggtgactac     420
aaggacgatg acgataagtg gagccatccg cagtttgaga atctagaaa gctttaacat      480 atgactcgag t                                                         491

<210> SEQ ID NO 5
<211> LENGTH: 5875
```

<212> TYPE: DNA
<213> ORGANISM: Artificial Sequence
<220> FEATURE:
<223> OTHER INFORMATION: Synthetic plasmid

<400> SEQUENCE: 5

```
gacgtcttga cagctagctc agtcctaggg attgtgctag caggtttaat cgaattgacg      60
tctttacggc tagctcagtc ctaggtacta tgctagcagg tttaatcgaa ttcaaaagat     120
cttttaagaa ggagatatac atatgattac tcatggttgt tatacccgga cccggcacaa     180
gcataagcta aaaaaaacat tgattatgct tagtgctggt ttaggattgt tttttttatgt    240 taatcagaac tcatttgcaa atggtgaaaa ttattttaaa ttgggttcgg attcaaaact     300
gttaactcat gatagctatc agaatcgcct tttttatacg ttgaaaactg gtgaaactgt     360
tgccgatctt tctaaatcgc aagatattaa tttatcgacg atttggtcgt tgaataagca     420
tttatacagt tctgaaagcg aaatgatgaa ggccgcgcct ggtcagcaga tcattttgcc     480
actcaaaaaa cttccctttg aatacagtgc actaccactt ttaggttcgg cacctcttgt     540
tgctgcgggt ggtgttgctg gtcacacgaa taaactgact aaaatgtccc cggacgtgac     600
caaaagcaac atgaccgatg acaaggcatt aaattatgcg gcacaacagg cggcgagtct     660
cggtagccag cttcagtcgc gatctctgaa cggcgattac gcgaaagata ccgctcttgg     720
tatcgctggt aaccaggctt cgtcacagtt gcaggcctgg ttacaacatt atggaacggc     780
agaggttaat ctgcaaagtg gtaataactt tgacggtagt tcactggact tcttattacc     840
gttctatgat tccgaaaaaa tgctggcatt tggtcaggtc ggagcgcgtt acattgactc     900
ccgctttacg gcaaatttag gtgcgggtca gcgtttttttc cttcctgcaa acatgttggg     960
ctataacgtc ttcattgatc aggatttttc tggtgataat acccgtttag gtattggtgg    1020
cgaatactgg cgagactatt tcaaaagtag cgttaacggc tatttccgca tgagcggctg    1080
gcatgagtca tacaataaga aagactatga tgagcgccca gcaaatggct tcgtatccg     1140 ttttaatggc tatctaccgt catatccggc attaggcgcc aagctgatat atgagcagta    1200
ttatggtgat aatgttgctt tgtttaattc tgataagctg caatcgaatc ctggtgcggc    1260
gaccgttggt gtaaactata ctccgattcc tctggtgacg atgggatcg attaccgtca     1320 tggtacgggt aatgaaaatg atctcctta ctcaatgcag ttccgttatc agtttgataa     1380
atcgtggtct cagcaaattg aaccacagta tgttaacgag ttaagaacat tatcaggcag    1440
ccgttacgat ctggttcagc gtaataacaa tattattctg gagtacaaga agcaggatat    1500
tctttctctg aatattccgc atgatattaa tggtactgaa cacagtacgc agaagattca    1560
gttgatcgtt aagagcaaat acggtctgga tcgtatcgtc tgggatgata gtgcattacg    1620
cagtcagggc ggtcagattc agcatagcgg aagccaaagc gcacaagact accaggctat    1680
tttgcctgct tatgtgcaag gtggcagcaa tatttataaa gtgacggctc gcgcctatga    1740
ccgtaatggc aatagctcta caatgtaca gcttactatt accgttctgt cgaatggtca     1800
agttgtcgac caggttgggg taacggactt tacggcggat aagacttcgg ctaaagcgga    1860
taacgccgat accattactt ataccgcgac ggtgaaaaag aatggggtag ctcaggctaa    1920
tgtccctgtt tcatttaata ttgtttcagg aactgcaact cttggggcaa atagtgccaa    1980
aacggatgct aacggtaagg caaccgtaac gttgaagtcg agtacgccag acaggtcgt     2040 cgtgtctgct aaaaccgcgg agatgacttc agcacttaat gccagtgcgg ttatattttt    2100
tgatggtgcg cccgggaagc ttgaaaacct gtacttccaa ggtacgcgtc aggtgcagct    2160
```

-continued

```
ggtggaaacc ggcggcggcc tggtgcagcc gggcggcagc ctgcgcctga gctgcgcggc      2220
gagcggcttt acctttagca gcgtgtatat gaactgggtg cgccaggcgc cgggcaaagg      2280
cccggaatgg gtgagccgca ttagcccgaa cagcggcaac attggctata ccgatagcgt      2340
gaaaggccgc tttaccatta gccgcgataa cgcgaaaaac accctgtatc tgcagatgaa      2400
caacctgaaa ccggaagata ccgcgctgta ttattgcgcg attggcctga acctgagcag      2460
cagcagcgtg cgcggccagg gcacccaggt gaccgtgagc agcggatccg aaaacctgta      2520
cttccaaggt gactacaagg acgatgacga taagtggagc catccgcagt ttgagaaatc      2580
tagataaggt accactcgag taaggatctc caggcatcaa ataaaacgaa aggctcagtc      2640
gaaagactgg gcctttcgtt ttatctgttg tttgtcggtg aacgctctct actagagtca      2700
cactggctca ccttcgggtg ggcctttctg cgtttatacc tagggtacgg tttttgctgc      2760
ccgcaaacgg gctgttctgg tgttgctagt ttgttatcag aatcgcagat ccggcttcag      2820
ccggtttgcc ggctgaaagc gctatttctt ccagaattgc catgattttt tccccacggg      2880
aggcgtcact ggctcccgtg ttgtcggcag ctttgattcg ataagcagca tcgcctgttt      2940
caggctgtct atgtgtgact gttgagctgt aacaagttgt ctcaggtgtt caatttcatg      3000
ttctagttgc tttgttttac tggtttcacc tgttctatta ggtgttacat gctgttcatc      3060
tgttacattg tcgatctgtt catggtgaac agctttgaat gcaccaaaaa ctcgtaaaag      3120
ctctgatgta tctatctttt ttacaccgtt ttcatctgtg catatggaca gttttccctt      3180
tgatatgtaa cggtgaacag ttgttctact tttgtttgtt agtcttgatg cttcactgat      3240
agatacaaga gccataagaa cctcagatcc ttccgtattt agccagtatg ttctctagtg      3300
tggttcgttg tttttgcgtg agccatgaga cgaaccatt gagatcatac ttactttgca      3360
tgtcactcaa aaattttgcc tcaaaactgg tgagctgaat ttttgcagtt aaagcatcgt      3420
gtagtgtttt tcttagtccg ttatgtaggt aggaatctga tgtaatggtt gttggtattt      3480
tgtcaccatt cattttatc tggttgttct caagttcggt tacgagatcc atttgtctat      3540
ctagttcaac ttggaaaatc aacgtatcag tcgggcggcc tcgcttatca accaccaatt      3600
tcatattgct gtaagtgttt aaatctttac ttattggttt caaaacccat ggttaagcc      3660 tttaaactc atggtagtta ttttcaagca ttaacatgaa cttaaattca tcaaggctaa      3720
tctctatatt tgccttgtga gttttctttt gtgttagttc ttttaataac cactcataaa      3780
tcctcataga gtatttgttt tcaaaagact taacatgttc cagattatat tttatgaatt      3840
tttttaactg gaaaagataa ggcaatatct cttcactaaa aactaattct aattttttcgc      3900 ttgagaactt ggcatagttt gtccactgga aaatctcaaa gcctttaacc aaaggattcc      3960
tgatttccac agttctcgtc atcagctctc tggttgcttt agctaataca ccataagcat      4020
tttccctact gatgttcatc atctgagcgt attggttata agtgaacgat accgtccgtt      4080
ctttccttgt agggttttca atcgtggggt tgagtagtgc cacacagcat aaaattagct      4140
tggtttcatg ctccgttaag tcatagcgac taatcgctag ttcatttgct ttgaaaacaa      4200
ctaattcaga catacatctc aattggtcta ggtgatttta atcactatac caattgagat      4260
gggctagtca atgataatta ctagtccttt tcccgggtga tctgggtatc tgtaaattct      4320
gctagacctt tgctggaaaa cttgtaaatt ctgctagacc ctctgtaaat tccgctagac      4380
ctttgtgtgt tttttttgtt tatattcaag tggttataat ttatagaata aagaaagaat      4440
aaaaaaagat aaaaagaata gatcccagcc ctgtgtataa ctcactactt tagtcagttc      4500
cgcagtatta caaaaggatg tcgcaaacgc tgtttgctcc tctacaaaac agaccttaaa      4560
```

-continued

```
accctaaagg cttaagtagc accctcgcaa gctcgggcaa atcgctgaat attccttttg    4620
tctccgacca tcaggcacct gagtcgctgt ctttttcgtg acattcagtt cgctgcgctc    4680
acggctctgg cagtgaatgg gggtaaatgg cactacaggc gccttttatg gattcatgca    4740
aggaaactac ccataataca agaaaagccc gtcacgggct tctcagggcg ttttatggcg    4800
ggtctgctat gtggtgctat ctgacttttt gctgttcagc agttcctgcc ctctgatttt    4860
ccagtctgac cacttcggat tatcccgtga caggtcattc agactggcta atgcacccag    4920
taaggcagcg gtatcatcaa caggcttacc cgtcttactg tccctagtgc ttggattctc    4980
accaataaaa aacgcccggc ggcaaccgag cgttctgaac aaatccagat ggagttctga    5040
ggtcattact ggatctatca acaggagtcc aagcgagctc gatatcaaat tacgccccgc    5100
cctgccactc atcgcagtac tgttgtaatt cattaagcat tctgccgaca tggaagccat    5160
cacaaacggc atgatgaacc tgaatcgcca gcggcatcag caccttgtcg ccttgcgtat    5220
aatatttgcc catggtgaaa acgggggcga agaagttgtc catattggcc acgtttaaat    5280
caaaactggt gaaactcacc cagggattgg ctgagacgaa aaacatattc tcaataaacc    5340
ctttagggaa ataggccagg ttttcaccgt aacacgccac atcttgcgaa tatatgtgta    5400
gaaactgccg gaaatcgtcg tggtattcac tccagagcga tgaaaacgtt tcagtttgct    5460
catggaaaac ggtgtaacaa gggtgaacac tatcccatat caccagctca ccgtctttca    5520
ttgccatacg aaattccgga tgagcattca tcaggcgggc aagaatgtga ataaaggccg    5580
gataaaactt gtgcttattt ttctttacgg tctttaaaaa ggccgtaata tccagctgaa    5640
cggtctggtt ataggtacat tgagcaactg actgaaatgc ctcaaaatgt tctttacgat    5700
gccattggga tatatcaacg gtggtatatc cagtgatttt tttctccatt ttagcttcct    5760
tagctcctga aaatctcgat aactcaaaaa atacgcccgg tagtgatctt atttcattat    5820
ggtgaaagtt ggaacctctt acgtgccgat caacgtctca ttttcgccag atatc        5875
```

```
<210> SEQ ID NO 6
<211> LENGTH: 5875
<212> TYPE: DNA
<213> ORGANISM: Artificial Sequence
<220> FEATURE:
<223> OTHER INFORMATION: Synthetic plasmid

<400> SEQUENCE: 6
gacgtcttga cagctagctc agtcctaggg attgtgctag caggtttaat cgaattgacg      60
tctttacggc tagctcagtc ctaggtacta tgctagcagg tttaatcgaa ttcaaaagat     120 ctttttaagaa ggagatatac atatgattac tcatggttgt tatacccgga cccggcacaa    180
gcataagcta aaaaaaacat tgattatgct tagtgctggt ttaggattgt tttttttatgt    240 taatcagaac tcatttgcaa atggtgaaaa ttattttaaa ttgggttcgg attcaaaact     300
gttaactcat gatagctatc agaatcgcct tttttatacg ttgaaaactg gtgaaactgt     360
tgccgatctt tctaaatcgc aagatattaa tttatcgacg atttggtcgt tgaataagca     420
tttatacagt tctgaaagcg aaatgatgaa ggccgcgcct ggtcagcaga tcattttgcc     480
actcaaaaaa cttccctttg aatacagtgc actaccactt ttaggttcgg cacctcttgt     540
tgctgcgggt ggtgttgctg gtcacacgaa taaactgact aaaaatgtccc cggacgtgac    600 caaaagcaac atgaccgatg acaaggcatt aaattatgcg gcacaacagg cggcgagtct     660
cggtagccag cttcagtcgc gatctctgaa cggcgattac gcgaaagata ccgctcttgg     720
```

-continued

```
tatcgctggt aaccaggctt cgtcacagtt gcaggcctgg ttacaacatt atggaacggc    780
agaggttaat ctgcaaagtg gtaataactt tgacggtagt tcactggact tcttattacc    840
gttctatgat tccgaaaaaa tgctggcatt tggtcaggtc ggagcgcgtt acattgactc    900
ccgctttacg gcaaatttag gtgcgggtca gcgttttttc cttcctgcaa acatgttggg    960
ctataacgtc ttcattgatc aggatttttc tggtgataat acccgtttag gtattggtgg    1020
cgaatactgg cgagactatt tcaaaagtag cgttaacggc tatttccgca tgagcggctg    1080
gcatgagtca tacaataaga aagactatga tgagcgccca gcaaatggct tcgatatccg    1140
ttttaatggc tatctaccgt catatccggc attaggcgcc aagctgatat atgagcagta    1200
ttatggtgat aatgttgctt tgtttaattc tgataagctg caatcgaatc ctggtgcggc    1260
gaccgttggt gtaaactata ctccgattcc tctggtgacg atggggatcg attaccgtca    1320
tggtacgggt aatgaaaatg atctccttta ctcaatgcag ttccgttatc agtttgataa    1380
atcgtggtct cagcaaattg aaccacagta tgttaacgag ttaagaacat tatcaggcag    1440
ccgttacgat ctggttcagc gtaataacaa tattattctg gagtacaaga agcaggatat    1500
tctttctctg aatattccgc atgatattaa tggtactgaa cacagtacgc agaagattca    1560
gttgatcgtt aagagcaaat acggtctgga tcgtatcgtc tgggatgata gtgcattacg    1620
cagtcagggc ggtcagattc agcatagcgg aagccaaagc gcacaagact accaggctat    1680
tttgcctgct tatgtgcaag gtggcagcaa tatttataaa gtgacggctc gcgcctatga    1740
ccgtaatggc aatagctcta acaatgtaca gcttactatt accgttctgt cgaatggtca    1800
agttgtcgac caggttgggg taacggactt tacggcggat aagacttcgg ctaaagcgga    1860
taacgccgat accattactt ataccgcgac ggtgaaaaag aatggggtag ctcaggctaa    1920
tgtccctgtt tcatttaata ttgtttcagg aactgcaact cttggggcaa atagtgccaa    1980
aacggatgct aacggtaagg caaccgtaac gttgaagtcg agtacgccag gacaggtcgt    2040
cgtgtctgct aaaaccgcgg agatgacttc agcacttaat gccagtgcgg ttatattttt    2100
tgatggtgcg cccgggaagc ttgaaaacct gtattttcag ggcacccgtc aggttcagct    2160
ggttgaaacc ggtggtggtc tggttcagcc tggtggtagc ctgcgtctga gctgtgcagc    2220
aagcggtttt acctttagca gcgtttatat gaattgggtt cgtcaggcac ctggtaaagg    2280
tccggaatgg gttagccgta ttagcccgaa tagcggtaat attggttata ccgatagcgt    2340
gaaaggtcgc tttaccatta gccgtgataa tgcaaaaaat accctgtacc tgcagatgaa    2400
taatctgaaa ccggaagata ccgcactgta ttattgtgca attggtctga atctgagcag    2460
cagcagcgtt cgtggtcagg tacacaggt taccgtgagc agcggtagcg agaatctgta    2520
tttccaaggt gattataaag acgacgatga caagtggtcc catccgcagt ttgaaaaaag    2580
ccgttaaggt accactcgag taaggatctc caggcatcaa ataaaacgaa aggctcagtc    2640
gaaagactgg gcctttcgtt ttatctgttg tttgtcggtg aacgctctct actagagtca    2700
cactggctca ccttcgggtg ggcctttctg cgtttatacc tagggtacgg tttttgctgc    2760
ccgcaaacgg gctgttctgg tgttgctagt ttgttatcag aatcgcagat ccggcttcag    2820
ccggtttgcc ggctgaaagc gctatttctt ccagaattgc catgattttt tccccacggg    2880
aggcgtcact ggctcccgtg ttgtcggcag ctttgattcg ataagcagca tcgcctgttt    2940
caggctgtct atgtgtgact gttgagctgt aacaagttgt ctcaggtgtt caatttcatg    3000
ttctagttgc tttgttttac tggtttcacc tgttctatta ggtgttacat gctgttcatc    3060
tgttacattg tcgatctgtt catggtgaac agctttgaat gcaccaaaaa ctcgtaaaag    3120
```

```
ctctgatgta tctatctttt ttacaccgtt ttcatctgtg catatggaca gtttttccctt    3180 tgatatgtaa cggtgaacag ttgttctact tttgtttgtt agtcttgatg cttcactgat    3240
agatacaaga gccataagaa cctcagatcc ttccgtattt agccagtatg ttctctagtg    3300
tggttcgttg tttttgcgtg agccatgaga acgaaccatt gagatcatac ttactttgca    3360
tgtcactcaa aaattttgcc tcaaaactgg tgagctgaat ttttgcagtt aaagcatcgt    3420
gtagtgtttt tcttagtccg ttatgtaggt aggaatctga tgtaatggtt gttggtattt    3480
tgtcaccatt cattttttatc tggttgttct caagttcggt tacgagatcc atttgtctat    3540
ctagttcaac ttggaaaatc aacgtatcag tcgggcggcc tcgcttatca accaccaatt    3600
tcatattgct gtaagtgttt aaatctttac ttattggttt caaaacccat tggttaagcc    3660
ttttaaactc atggtagtta ttttcaagca ttaacatgaa cttaaattca tcaaggctaa    3720
tctctatatt tgccttgtga gttttctttt gtgttagttc ttttaataac cactcataaa    3780
tcctcataga gtatttgttt tcaaaagact taacatgttc cagattatat tttatgaatt    3840
tttttaactg gaaaagataa ggcaatatct cttcactaaa aactaattct aattttttcgc    3900 ttgagaactt ggcatagttt gtccactgga aaatctcaaa gcctttaacc aaaggattcc    3960
tgatttccac agttctcgtc atcagctctc tggttgcttt agctaataca ccataagcat    4020 tttcccctact gatgttcatc atctgagcgt attggttata agtgaacgat accgtccgtt    4080
ctttccttgt agggttttca atcgtggggt tgagtagtgc cacacagcat aaaattagct    4140
tggtttcatg ctccgttaag tcatagcgac taatcgctag ttcatttgct ttgaaaacaa    4200
ctaattcaga catacatctc aattggtcta ggtgattta atcactatac caattgagat    4260
gggctagtca atgataatta ctagtccttt tcccgggtga tctgggtatc tgtaaattct    4320
gctagacctt tgctggaaaa cttgtaaatt ctgctagacc ctctgtaaat tccgctagac    4380
ctttgtgtgt tttttttgtt tatattcaag tggttataat ttatagaata aagaaagaat    4440
aaaaaaagat aaaaagaata gatcccagcc ctgtgtataa ctcactactt tagtcagttc    4500
cgcagtatta caaaaggatg tcgcaaacgc tgtttgctcc tctacaaaac agaccttaaa    4560
accctaaagg cttaagtagc accctcgcaa gctcgggcaa atcgctgaat attccttttg    4620
tctccgacca tcaggcacct gagtcgctgt ctttttcgtg acattcagtt cgctgcgctc    4680
acggctctgg cagtgaatgg gggtaaatgg cactacaggc gccttttatg gattcatgca    4740
aggaaactac ccataataca agaaaagccc gtcacgggct tctcagggcg ttttatggcg    4800
ggtctgctat gtggtgctat ctgacttttt gctgttcagc agttcctgcc ctctgatttt    4860
ccagtctgac cacttcggat tatcccgtga caggtcattc agactggcta atgcacccag    4920
taaggcagcg gtatcatcaa caggcttacc cgtcttactg tccctagtgc ttggattctc    4980
accaataaaa aacgcccggc ggcaaccgag cgttctgaac aaatccagat ggagttctga    5040
ggtcattact ggatctatca acaggagtcc aagcgagctc gatatcaaat tacgccccgc    5100
cctgccactc atcgcagtac tgttgtaatt cattaagcat tctgccgaca tggaagccat    5160
cacaaacggc atgatgaacc tgaatcgcca gcggcatcag caccttgtcg ccttgcgtat    5220
aatatttgcc catggtgaaa acggggggcga agaagttgtc catattggcc acgtttaaat    5280
caaaactggt gaaactcacc cagggattgg ctgagacgaa aaacatattc tcaataaacc    5340
ctttagggaa ataggccagg ttttcaccgt aacacgccac atcttgcgaa tatatgtgta    5400
gaaactgccg gaaatcgtcg tggtattcac tccagagcga tgaaaacgtt tcagtttgct    5460
```

-continued

```
catggaaaac ggtgtaacaa gggtgaacac tatcccatat caccagctca ccgtctttca      5520
ttgccatacg aaattccgga tgagcattca tcaggcgggc aagaatgtga ataaaggccg      5580
gataaaactt gtgcttattt ttctttacgg tctttaaaaa ggccgtaata tccagctgaa      5640
cggtctggtt ataggtacat tgagcaactg actgaaatgc ctcaaaatgt tctttacgat      5700
gccattggga tatatcaacg gtggtatatc cagtgatttt tttctccatt ttagcttcct      5760
tagctcctga aaatctcgat aactcaaaaa atacgcccgg tagtgatctt atttcattat      5820
ggtgaaagtt ggaacctctt acgtgccgat caacgtctca ttttcgccag atatc          5875
```

```
<210> SEQ ID NO 7
<211> LENGTH: 5902
<212> TYPE: DNA
<213> ORGANISM: Artificial Sequence
<220> FEATURE:
<223> OTHER INFORMATION: Synthetic plasmid

<400> SEQUENCE: 7
gacgtcttga cagctagctc agtcctaggg attgtgctag caggtttaat cgaattgacg        60
tctttacggc tagctcagtc ctaggtacta tgctagcagg tttaatcgaa ttcaaaagat       120
cttttaagaa ggagatatac atatgattac tcatggttgt tatacccgga cccggcacaa       180
gcataagcta aaaaaaacat tgattatgct tagtgctggt ttaggattgt ttttttatgt       240
taatcagaac tcatttgcaa atggtgaaaa ttattttaaa ttgggttcgg attcaaaact       300
gttaactcat gatagctatc agaatcgcct ttttttatacg ttgaaaactg gtgaaactgt       360
tgccgatctt tctaaatcgc aagatattaa tttatcgacg atttggtcgt tgaataagca       420
tttatacagt tctgaaagcg aaatgatgaa ggccgcgcct ggtcagcaga tcattttgcc       480
actcaaaaaa cttcccttttg aatacagtgc actaccactt ttaggttcgg cacctcttgt       540
tgctgcgggt ggtgttgctg gtcacacgaa taaactgact aaaaatgtccc cggacgtgac       600 caaaagcaac atgaccgatg acaaggcatt aaattatgcg gcacaacagg cggcgagtct       660
cggtagccag cttcagtcgc gatctctgaa cggcgattac gcgaaagata ccgctcttgg       720
tatcgctggt aaccaggctt cgtcacagtt gcaggcctgg ttacaacatt atggaacggc       780
agaggttaat ctgcaaagtg gtaataactt tgacggtagt tcactggact tcttattacc       840
gttctatgat tccgaaaaaa tgctggcatt tggtcaggtc ggagcgcgtt acattgactc       900
ccgctttacg gcaaatttag gtgcgggtca gcgttttttc cttcctgcaa acatgttggg       960
ctataacgtc ttcattgatc aggattttttc tggtgataat acccgtttag gtattggtgg      1020
cgaatactgg cgagactatt tcaaaagtag cgttaacggc tatttccgca tgagcggctg      1080
gcatgagtca tacaataaga aagactatga tgagcgccca gcaaatggct tcgatatccg      1140
ttttaatggc tatctaccgt catatccggc attaggcgcc aagctgatat atgagcagta      1200
ttatggtgat aatgttgctt tgtttaattc tgataagctg caatcgaatc ctggtgcggc      1260
gaccgttggt gtaaactata ctccgattcc tctggtgacg atggggatcg attaccgtca      1320
tggtacgggt aatgaaaatg atctccttta ctcaatgcag ttccgttatc agtttgataa      1380
atcgtggtct cagcaaattg aaccacagta tgttaacgag ttaagaacat tatcaggcag      1440
ccgttacgat ctggttcagc gtaataacaa tattattctg gagtacaaga agcaggatat      1500
tctttctctg aatattccgc atgatattaa tggtactgaa cacagtacgc agaagattca      1560
gttgatcgtt aagagcaaat acggtctgga tcgtatcgtc tgggatgata gtgcattacg      1620
cagtcagggc ggtcagattc agcatagcgg aagccaaagc gcacaagact accaggctat      1680
```

```
tttgcctgct tatgtgcaag gtggcagcaa tatttataaa gtgacggctc gcgcctatga    1740
ccgtaatggc aatagctcta acaatgtaca gcttactatt accgttctgt cgaatggtca    1800
agttgtcgac caggttgggg taacggactt tacggcggat aagacttcgg ctaaagcgga    1860
taacgccgat accattactt ataccgcgac ggtgaaaaag aatggggtag ctcaggctaa    1920
tgtccctgtt tcatttaata ttgtttcagg aactgcaact cttggggcaa atagtgccaa    1980
aacggatgct aacggtaagg caaccgtaac gttgaagtcg agtacgccag gacaggtcgt    2040
cgtgtctgct aaaaccgcgg agatgacttc agcacttaat gccagtgcgg ttatattttt    2100
tgatggtgcg cccgggaagc ttgaaaacct gtacttccaa ggtacgcgtc aggtgcagct    2160
gcaggaaagc ggtggtggtc tggtgcaggc cggtggtagc ctgcgtctga gctgtgccgc    2220
cagcggtcgt acctttagcg aatatgccat gggttggttt cgtcaggccc cgggtaaaga    2280
acgtgaattt gtggccacca ttagctggag cggtggtagc acctattata ccgatagcgt    2340
gaaaggtcgt tttaccatta gccgtgataa tgccaaaaat accgtgtatc tgcagatgaa    2400
tagcctgaaa ccggatgata ccgccgtgta ttattgtgcc gccgccggtc tgggtaccgt    2460
ggtgagcgaa tgggattatg attatgatta ttggggtcag ggtacccagg tgaccgtgag    2520
cagcggtagc ggatccgaaa acctgtactt ccaaggtgac tacaaggacg atgacgataa    2580
gtggagccat ccgcagtttg agaaatctag ataaggtacc actcgagtaa ggatctccag    2640
gcatcaaata aaacgaaagg ctcagtcgaa agactgggcc tttcgtttta tctgttgttt    2700
gtcggtgaac gctctctact agagtcacac tggctcacct tcgggtgggc ctttctgcgt    2760
ttatacctag ggtacgggtt ttgctgcccg caaacgggct gttctggtgt tgctagtttg    2820
ttatcagaat cgcagatccg gcttcagccg gtttgccggc tgaaagcgct atttcttcca    2880
gaattgccat gatttttttcc ccacgggagg cgtcactggc tcccgtgttg tcggcagctt    2940
tgattcgata agcagcatcg cctgtttcag gctgtctatg tgtgactgtt gagctgtaac    3000
aagttgtctc aggtgttcaa tttcatgttc tagttgcttt gttttactgg tttcacctgt    3060
tctattaggt gttacatgct gttcatctgt tacattgtcg atctgttcat ggtgaacagc    3120
tttgaatgca ccaaaaactc gtaaaagctc tgatgtatct atctttttta caccgttttc    3180
atctgtgcat atggacagtt ttccctttga tatgtaacgg tgaacagttg ttctactttt    3240
gtttgttagt cttgatgctt cactgataga tacaagagcc ataagaacct cagatccttc    3300
cgtatttagc cagtatgttc tctagtgtgg ttcgttgttt ttgcgtgagc catgagaacg    3360
aaccattgag atcatactta ctttgcatgt cactcaaaaa ttttgcctca aaactggtga    3420
gctgaatttt tgcagttaaa gcatcgtgta gtgttttttct tagtccgtta tgtaggtagg    3480
aatctgatgt aatggttgtt ggtattttgt caccattcat ttttatctgg ttgttctcaa    3540
gttcggttac gagatccatt tgtctatcta gttcaacttg gaaaatcaac gtatcagtcg    3600
ggcggcctcg cttatcaacc accaatttca tattgctgta agtgtttaaa tctttactta    3660
ttggtttcaa aacccattgg ttaagccttt taaactcatg gtagttattt tcaagcatta    3720
acatgaactt aaattcatca aggctaatct ctatatttgc cttgtgagtt ttcttttgtg    3780
ttagttcttt taataaccac tcataaatcc tcatagagta tttgtttttca aaagacttaa    3840 catgttccag attatatttt atgaattttt ttaactggaa aagataaggc aatatctctt    3900
cactaaaaac taattctaat ttttcgcttg agaacttggc atagtttgtc cactggaaaa    3960
tctcaaagcc tttaaccaaa ggattcctga tttccacagt tctcgtcatc agctctctgg    4020
```

```
ttgctttagc taatacacca taagcatttt ccctactgat gttcatcatc tgagcgtatt    4080
ggttataagt gaacgatacc gtccgttctt tccttgtagg gttttcaatc gtggggttga    4140
gtagtgccac acagcataaa attagcttgg tttcatgctc cgttaagtca tagcgactaa    4200
tcgctagttc atttgctttg aaaacaacta attcagacat acatctcaat tggtctaggt    4260
gattttaatc actataccaa ttgagatggg ctagtcaatg ataattacta gtcctttttcc   4320 cgggtgatct gggtatctgt aaattctgct agacctttgc tggaaaactt gtaaattctg    4380
ctagaccctc tgtaaattcc gctagacctt tgtgtgtttt ttttgtttat attcaagtgg    4440
ttataattta tagaataaag aaagaataaa aaaagataaa aagaatagat cccagccctg    4500
tgtataactc actactttag tcagttccgc agtattacaa aaggatgtcg caaacgctgt    4560
ttgctcctct acaaaacaga ccttaaaacc ctaaaggctt aagtagcacc ctcgcaagct    4620
cgggcaaatc gctgaatatt cctttgtct ccgaccatca ggcacctgag tcgctgtctt     4680
tttcgtgaca ttcagttcgc tgcgctcacg gctctggcag tgaatggggg taaatggcac    4740
tacaggcgcc ttttatggat tcatgcaagg aaactaccca taatacaaga aaagcccgtc    4800
acgggcttct cagggcgttt tatggcgggt ctgctatgtg gtgctatctg acttttttgct   4860 gttcagcagt tcctgccctc tgattttcca gtctgaccac ttcggattat cccgtgacag    4920
gtcattcaga ctggctaatg cacccagtaa ggcagcggta tcatcaacag gcttacccgt    4980
cttactgtcc ctagtgcttg gattctcacc aataaaaaac gcccggcggc aaccgagcgt    5040
tctgaacaaa tccagatgga gttctgaggt cattactgga tctatcaaca ggagtccaag    5100
cgagctcgat atcaaattac gccccgccct gccactcatc gcagtactgt tgtaattcat    5160
taagcattct gccgacatgg aagccatcac aaacggcatg atgaacctga atcgccagcg    5220
gcatcagcac cttgtcgcct tgcgtataat atttgcccat ggtgaaaacg ggggcgaaga    5280
agttgtccat attggccacg tttaaatcaa aactggtgaa actcacccag ggattggctg    5340
agacgaaaaa catattctca ataaaccctt tagggaaata ggccaggttt tcaccgtaac    5400
acgccacatc ttgcgaatat atgtgtagaa actgccggaa atcgtcgtgg tattcactcc    5460
agagcgatga aaacgtttca gtttgctcat ggaaaacggt gtaacaaggg tgaacactat    5520
cccatatcac cagctcaccg tctttcattg ccatacgaaa ttccggatga gcattcatca    5580
ggcgggcaag aatgtgaata aaggccggat aaaacttgtg cttatttttc tttacggtct    5640
ttaaaaaggc cgtaatatcc agctgaacgg tctggttata ggtacattga gcaactgact    5700
gaaatgcctc aaaatgttct ttacgatgcc attgggatat atcaacggtg gtatatccag    5760
tgattttttt ctccatttta gcttccttag ctcctgaaaa tctcgataac tcaaaaaata    5820
cgcccggtag tgatcttatt tcattatggt gaaagttgga acctcttacg tgccgatcaa    5880
cgtctcattt tcgccagata tc                                            5902
```

```
<210> SEQ ID NO 8
<211> LENGTH: 4336
<212> TYPE: DNA
<213> ORGANISM: Artificial Sequence
<220> FEATURE:
<223> OTHER INFORMATION: Synthetic plasmid

<400> SEQUENCE: 8
gacgtcttga cagctagctc agtcctaggg attgtgctag caggtttaat cgaattgacg     60
tctttacggc tagctcagtc ctaggtacta tgctagcagg tttaatcgaa ttcaaaagat    120
cttttaagaa ggagatatac atatgaaagc aaccaagctg gttctgggtg ccgtgattct    180
```

```
gggcagtacc ctgttagcag gttgttctag caatgccaaa atcgaccaag gcatcaacaa      240
caatggcccg acccacgaaa accagctggg tgccggtgcc tttggtggtt atcaggtgaa      300
cccgtacgtg ggctttgaaa tgggctatga ttggctgggc cgcatgccgt acaaaggcag      360
tgtggagaac ggcgcctata aagcacaggg cgtgcagctg acagcaaaac tgggctaccc      420
tattaccgac gacctggaca tctacacacg cttaggcggc atggtgtggc gcgccgatac      480
caagagcaac gtgtacggca agaaccacga taccggcgtg agtccggtgt ttgccggcgg      540
tgtggagtat gcaatcaccc cggaaattgc cacacgtaag cttgaaaacc tgtacttcca      600
aggtacgcgt caggtgcagc tggtggaaac cggcggcggc ctggtgcagc cgggcggcag      660
cctgcgcctg agctgcgcgg cgagcggctt tacctttagc agcgtgtata tgaactgggt      720
gcgccaggcg ccgggcaaag gcccggaatg ggtgagccgc attagcccga acagcggcaa      780
cattggctat accgatagcg tgaaaggccg cttttaccatt agccgcgata cgcgaaaaa      840 caccctgtat ctgcagatga acaacctgaa accggaagat accgcgctgt attattgcgc      900
gattggcctg aacctgagca gcagcagcgt gcgcggccag ggcacccagg tgaccgtgag      960
cagcggatcc gaaaacctgt acttccaagg tgactacaag gacgatgacg ataagtggag     1020
ccatccgcag tttgagaaat ctagataagg taccactcga gtaaggatct ccaggcatca     1080
aataaaacga aaggctcagt cgaaagactg ggcctttcgt tttatctgtt gtttgtcggt     1140
gaacgctctc tactagagtc acactggctc accttcgggt gggcctttct gcgtttatac     1200
ctagggtacg ggttttgctg cccgcaaacg ggctgttctg gtgttgctag tttgttatca     1260
gaatcgcaga tccggcttca gccggtttgc cggctgaaag cgctatttct tccagaattg     1320
ccatgatttt ttccccacgg gaggcgtcac tggctcccgt gttgtcggca gctttgattc     1380
gataagcagc atcgcctgtt tcaggctgtc tatgtgtgac tgttgagctg taacaagttg     1440
tctcaggtgt tcaatttcat gttctagttg ctttgtttta ctggtttcac ctgttctatt     1500
aggtgttaca tgctgttcat ctgttacatt gtcgatctgt tcatggtgaa cagctttgaa     1560
tgcaccaaaa actcgtaaaa gctctgatgt atctatcttt tttacaccgt tttcatctgt     1620
gcatatggac agttttccct ttgatatgta acggtgaaca gttgttctac ttttgtttgt     1680
tagtcttgat gcttcactga tagatacaag agccataaga acctcagatc cttccgtatt     1740
tagccagtat gttctctagt gtggttcgtt gtttttgcgt gagccatgag aacgaaccat     1800
tgagatcata cttactttgc atgtcactca aaaattttgc ctcaaaactg gtgagctgaa     1860
tttttgcagt taaagcatcg tgtagtgttt ttcttagtcc gttatgtagg taggaatctg     1920
atgtaatggt tgttggtatt ttgtcaccat tcattttat ctggttgttc tcaagttcgg     1980
ttacgagatc catttgtcta tctagttcaa cttggaaaat caacgtatca gtcgggcggc     2040
ctcgcttatc aaccaccaat ttcatattgc tgtaagtgtt taaatcttta cttattggtt     2100
tcaaaaccca ttggttaagc cttttaaact catggtagtt attttcaagc attaacatga     2160
acttaaattc atcaaggcta atctctatat ttgccttgtg agttttcttt tgtgttagtt     2220
cttttaataa ccactcataa atcctcatag agtatttgtt ttcaaaagac ttaacatgtt     2280
ccagattata ttttatgaat ttttttaact ggaaaagata aggcaatatc tcttcactaa     2340
aaactaattc taattttttcg cttgagaact tggcatagtt tgtccactgg aaaatctcaa     2400
agcctttaac caaaggattc ctgatttcca cagttctcgt catcagctct ctggttgctt     2460
tagctaatac accataagca tttttccctac tgatgttcat catctgagcg tattggttat     2520
```

```
aagtgaacga taccgtccgt tctttccttg tagggttttc aatcgtgggg ttgagtagtg      2580
ccacacagca taaaattagc ttggtttcat gctccgttaa gtcatagcga ctaatcgcta      2640
gttcatttgc tttgaaaaca actaattcag acatacatct caattggtct aggtgatttt      2700
aatcactata ccaattgaga tgggctagtc aatgataatt actagtcctt ttcccgggtg      2760
atctgggtat ctgtaaattc tgctagacct ttgctggaaa acttgtaaat tctgctagac      2820
cctctgtaaa ttccgctaga cctttgtgtg tttttttttgt ttatattcaa gtggttataa      2880
tttatagaat aaagaaagaa taaaaaaaga taaaaagaat agatcccagc cctgtgtata      2940
actcactact ttagtcagtt ccgcagtatt acaaaaggat gtcgcaaacg ctgtttgctc      3000
ctctacaaaa cagaccttaa aaccctaaag gcttaagtag caccctcgca agctcgggca      3060
aatcgctgaa tattcctttt gtctccgacc atcaggcacc tgagtcgctg tcttttttcgt      3120 gacattcagt tcgctgcgct cacggctctg gcagtgaatg ggggtaaatg gcactacagg      3180 cgcctttttat ggattcatgc aaggaaacta cccataatac aagaaaagcc cgtcacgggc      3240
ttctcagggc gttttatggc gggtctgcta tgtggtgcta tctgactttt tgctgttcag      3300
cagttcctgc cctctgattt tccagtctga ccacttcgga ttatcccgtg acaggtcatt      3360
cagactggct aatgcaccca gtaaggcagc ggtatcatca acaggcttac ccgtcttact      3420
gtccctagtg cttggattct caccaataaa aaacgcccgg cggcaaccga gcgttctgaa      3480
caaatccaga tggagttctg aggtcattac tggatctatc aacaggagtc caagcgagct      3540
cgatatcaaa ttacgccccg ccctgccact catcgcagta ctgttgtaat tcattaagca      3600
ttctgccgac atggaagcca tcacaaacgg catgatgaac ctgaatcgcc agcggcatca      3660
gcaccttgtc gccttgcgta taatatttgc ccatggtgaa aacgggggcg aagaagttgt      3720
ccatattggc cacgtttaaa tcaaaactgg tgaaactcac ccagggattg gctgagacga      3780
aaaacatatt ctcaataaac cctttaggga ataggccag gttttcaccg taacacgcca      3840
catcttgcga atatatgtgt agaaactgcc ggaaatcgtc gtggtattca ctccagagcg      3900
atgaaaacgt ttcagtttgc tcatggaaaa cggtgtaaca agggtgaaca ctatcccata      3960
tcaccagctc accgtctttc attgccatac gaaattccgg atgagcattc atcaggcggg      4020
caagaatgtg aataaaggcc ggataaaact tgtgcttatt tttctttacg gtctttaaaa      4080
aggccgtaat atccagctga acggtctggt tataggtaca ttgagcaact gactgaaatg      4140
cctcaaaatg ttctttacga tgccattggg atatatcaac ggtggtatat ccagtgattt      4200
ttttctccat tttagcttcc ttagctcctg aaaatctcga taactcaaaa aatacgcccg      4260
gtagtgatct tatttcatta tggtgaaagt tggaacctct tacgtgccga tcaacgtctc      4320
attttcgcca gatatc                                                     4336
```

<210> SEQ ID NO 9
<211> LENGTH: 4363
<212> TYPE: DNA
<213> ORGANISM: Artificial Sequence
<220> FEATURE:
<223> OTHER INFORMATION: Synthetic plasmid

<400> SEQUENCE: 9

```
gacgtcttga cagctagctc agtcctaggg attgtgctag caggtttaat cgaattgacg       60
tctttacggc tagctcagtc ctaggtacta tgctagcagg tttaatcgaa ttcaaaagat      120
cttttaagaa ggagatatac atatgaaagc aaccaagctg gttctgggtg ccgtgattct      180
gggcagtacc ctgttagcag gttgttctag caatgccaaa atcgaccaag gcatcaacaa      240
```

```
caatggcccg acccacgaaa accagctggg tgccggtgcc tttggtggtt atcaggtgaa      300
cccgtacgtg ggctttgaaa tgggctatga ttggctgggc cgcatgccgt acaaaggcag      360
tgtggagaac ggcgcctata aagcacaggg cgtgcagctg acagcaaaac tgggctaccc      420
tattaccgac gacctggaca tctacacacg cttaggcggc atggtgtggc gcgccgatac      480
caagagcaac gtgtacggca agaaccacga taccggcgtg agtccggtgt ttgccggcgg      540
tgtggagtat gcaatcaccc cggaaattgc cacacgtaag cttgaaaacc tgtacttcca      600
aggtacgcgt caggtgcagc tgcaggaaag cggtggtggt ctggtgcagg ccggtggtag      660
cctgcgtctg agctgtgccg ccagcggtcg tacctttagc gaatatgcca tgggttggtt      720
tcgtcaggcc ccgggtaaag aacgtgaatt tgtggccacc attagctgga gcggtggtag      780
cacctattat accgatagcg tgaaaggtcg ttttaccatt agccgtgata atgccaaaaa      840
taccgtgtat ctgcagatga atagcctgaa accggatgat accgccgtgt attattgtgc      900
cgccgccggt ctgggtaccg tggtgagcga atgggattat gattatgatt attggggtca      960
gggtacccag gtgaccgtga gcagcggtag cggatccgaa aacctgtact tccaaggtga     1020
ctacaaggac gatgacgata gtggagcca tccgcagttt gagaaatcta gataaggtac     1080
cactcgagta aggatctcca ggcatcaaat aaaacgaaag gctcagtcga aagactgggc     1140
ctttcgtttt atctgttgtt tgtcggtgaa cgctctctac tagagtcaca ctggctcacc     1200
ttcgggtggg cctttctgcg tttatcccta gggtacgggt tttgctgccc gcaaacgggc     1260
tgttctggtg ttgctagttt gttatcagaa tcgcagatcc ggcttcagcc ggtttgccgg     1320
ctgaaagcgc tatttcttcc agaattgcca tgatttttc cccacgggag gcgtcactgg     1380
ctcccgtgtt gtcggcagct ttgattcgat aagcagcatc gcctgtttca ggctgtctat     1440
gtgtgactgt tgagctgtaa caagttgtct caggtgttca atttcatgtt ctagttgctt     1500
tgttttactg gtttcacctg ttctattagg tgttacatgc tgttcatctg ttacattgtc     1560
gatctgttca tggtgaacag ctttgaatgc accaaaaact cgtaaaagct ctgatgtatc     1620
tatctttttt acaccgtttt catctgtgca tatggacagt tttccctttg atatgtaacg     1680
gtgaacagtt gttctacttt tgtttgttag tcttgatgct tcactgatag atacaagagc     1740
cataagaacc tcagatcctt ccgtatttag ccagtatgtt ctctagtgtg gttcgttgtt     1800
tttgcgtgag ccatgagaac gaaccattga gatcatactt actttgcatg tcactcaaaa     1860
attttgcctc aaaactggtg agctgaattt ttgcagttaa agcatcgtgt agtgtttttc     1920
ttagtccgtt atgtaggtag gaatctgatg taatggttgt tggtattttg tcaccattca     1980
tttttatctg gttgttctca agttcggtta cgagatccat ttgtctatct agttcaactt     2040
ggaaaatcaa cgtatcagtc gggcggcctc gcttatcaac caccaatttc atattgctgt     2100
aagtgtttaa atctttactt attggtttca aaacccattg gttaagcctt ttaaactcat     2160
ggtagttatt ttcaagcatt aacatgaact taaattcatc aaggctaatc tctatatttg     2220
ccttgtgagt tttcttttgt gttagttctt ttaataacca ctcataaatc ctcatagagt     2280
atttgttttc aaaagactta acatgttcca gattatattt tatgaatttt tttaactgga     2340
aaagataagg caatatctct tcactaaaaa ctaattctaa ttttttcgctt gagaacttgg     2400 catagtttgt ccactggaaa atctcaaagc ctttaaccaa aggattcctg atttccacag     2460
ttctcgtcat cagctctctg gttgctttag ctaatacacc ataagcattt tccctactga     2520
tgttcatcat ctgagcgtat tggttataag tgaacgatac cgtccgttct ttccttgtag     2580
```

-continued

```
ggttttcaat cgtggggttg agtagtgcca cacagcataa aattagcttg gtttcatgct      2640
ccgttaagtc atagcgacta atcgctagtt catttgcttt gaaaacaact aattcagaca      2700
tacatctcaa ttggtctagg tgattttaat cactatacca attgagatgg gctagtcaat      2760
gataattact agtccttttc ccgggtgatc tgggtatctg taaattctgc tagacctttg      2820
ctggaaaact tgtaaattct gctagaccct ctgtaaattc cgctagacct ttgtgtgttt      2880
tttttgttta tattcaagtg gttataattt atagaataaa gaaagaataa aaaaagataa      2940
aaagaataga tcccagccct gtgtataact cactacttta gtcagttccg cagtattaca      3000
aaaggatgtc gcaaacgctg tttgctcctc tacaaaacag accttaaaac cctaaaggct      3060
taagtagcac cctcgcaagc tcgggcaaat cgctgaatat tccttttgtc tccgaccatc      3120
aggcacctga gtcgctgtct ttttcgtgac attcagttcg ctgcgctcac ggctctggca      3180
gtgaatgggg gtaaatggca ctacaggcgc cttttatgga ttcatgcaag gaaactaccc      3240
ataatacaag aaaagcccgt cacgggcttc tcagggcgtt ttatggcggg tctgctatgt      3300
ggtgctatct gactttttgc tgttcagcag ttcctgccct ctgattttcc agtctgacca      3360
cttcggatta tcccgtgaca ggtcattcag actggctaat gcacccagta aggcagcggt      3420
atcatcaaca ggcttacccg tcttactgtc cctagtgctt ggattctcac caataaaaaa      3480
cgcccggcgg caaccgagcg ttctgaacaa atccagatgg agttctgagg tcattactgg      3540
atctatcaac aggagtccaa gcgagctcga tatcaaatta cgccccgccc tgccactcat      3600
cgcagtactg ttgtaattca ttaagcattc tgccgacatg gaagccatca caaacggcat      3660
gatgaacctg aatcgccagc ggcatcagca ccttgtcgcc ttgcgtataa tatttgccca      3720
tggtgaaaac ggggggcgaag aagttgtcca tattggccac gtttaaatca aaactggtga      3780
aactcaccca gggattggct gagacgaaaa acatattctc aataaaccct ttagggaaat      3840
aggccaggtt ttcaccgtaa cacgccacat cttgcgaata tatgtgtaga aactgccgga      3900
aatcgtcgtg gtattcactc cagagcgatg aaaacgtttc agtttgctca tggaaaacgg      3960
tgtaacaagg gtgaacacta tcccatatca ccagctcacc gtctttcatt gccatacgaa      4020
attccggatg agcattcatc aggcgggcaa gaatgtgaat aaaggccgga taaaacttgt      4080
gcttattttt ctttacggtc tttaaaaagg ccgtaatatc cagctgaacg gtctggttat      4140
aggtacattg agcaactgac tgaaatgcct caaaatgttc tttacgatgc cattgggata      4200
tatcaacggt ggtatatcca gtgatttttt tctccatttt agcttcctta gctcctgaaa      4260
atctcgataa ctcaaaaaat acgcccggta gtgatcttat ttcattatgg tgaaagttgg      4320
aacctcttac gtgccgatca acgtctcatt ttcgccagat atc                        4363
```

<210> SEQ ID NO 10
<211> LENGTH: 4363
<212> TYPE: DNA
<213> ORGANISM: Artificial Sequence
<220> FEATURE:
<223> OTHER INFORMATION: Synthetic plasmid

<400> SEQUENCE: 10

```
gacgtcttga cagctagctc agtcctaggg attgtgctag caggtttaat cgaattgacg       60
tctttacggc tagctcagtc ctaggtacta tgctagcagg tttaatcgaa ttcaaaagat      120
cttttaagaa ggagatatac atatgaaagc caccaaactg gttctgggtg cagttattct      180
gggtagcacc ctgctggcag gttgtagcag caatgcaaaa attgatcagg cattaataaa      240
caacggtccg acacatgaaa atcagttagg tgccggtgca tttggtggtt atcaggttaa      300
```

-continued

```
tccgtatgtg ggttttgaaa tgggttatga ttggctgggt cgtatgccgt ataaaggtag      360
cgttgaaaat ggtgcatata aagcacaggg tgttcagctg accgcaaaac tgggttatcc      420
gattaccgat gatctggata tctatacccg tttaggtggt atggtttggc gtgcagatac      480
caaaagcaat gtgtatggca aaaatcatga taccggtgtt agtccggttt ttgccggtgg      540
tgttgaatat gcaattacac cggaaattgc aacccgcaaa ctggaaaatc tgtattttca      600
gggcacccgt caggttcagc tgcaagaaag cggtggtggt ctggttcagg caggcggtag      660
cctgcgtctg agctgtgcag caagcggtcg tacctttagc gaatatgcca tgggttggtt      720
tcgtcaggca ccgggtaaag aacgtgaatt tgttgcaacc attagctggt ctggtggtag      780
cacctattat accgatagcg ttaaaggtcg ttttaccatt agccgtgata atgccaaaaa      840
taccgtttac ctgcagatga atagcctgaa accggatgat accgcagtgt attattgtgc      900
agcagcaggt ctgggtacag ttgttagcga gtgggattat gattatgact attggggtca      960
gggtacacag gttaccgtta gcagcggtag cggtagtgag aacctgtatt tccaaggtga     1020
ttataaagat gacgatgata gtggtcccca tccgcagttt gaaaaaagcc gttaaggtac     1080
cactcgagta aggatctcca ggcatcaaat aaaacgaaag gctcagtcga aagactgggc     1140
ctttcgtttt atctgttgtt tgtcggtgaa cgctctctac tagagtcaca ctggctcacc     1200
ttcgggtggg cctttctgcg tttataccta gggtacgggt tttgctgccc gcaaacgggc     1260
tgttctggtg ttgctagttt gttatcagaa tcgcagatcc ggcttcagcc ggtttgccgg     1320
ctgaaagcgc tatttcttcc agaattgcca tgattttttc cccacgggag gcgtcactgg     1380
ctcccgtgtt gtcggcagct ttgattcgat aagcagcatc gcctgtttca ggctgtctat     1440
gtgtgactgt tgagctgtaa caagttgtct caggtgttca atttcatgtt ctagttgctt     1500
tgttttactg gtttcacctg ttctattagg tgttacatgc tgttcatctg ttacattgtc     1560
gatctgttca tggtgaacag ctttgaatgc accaaaaact cgtaaaagct ctgatgtatc     1620
tatctttttt acaccgtttt catctgtgca tatggacagt tttccctttg atatgtaacg     1680
gtgaacagtt gttctacttt tgtttgttag tcttgatgct tcactgatag atacaagagc     1740
cataagaacc tcagatcctt ccgtatttag ccagtatgtt ctctagtgtg gttcgttgtt     1800
tttgcgtgag ccatgagaac gaaccattga gatcatactt actttgcatg tcactcaaaa     1860
attttgcctc aaaactggtg agctgaattt ttgcagttaa agcatcgtgt agtgtttttc     1920
ttagtccgtt atgtaggtag gaatctgatg taatggttgt tggtattttg tcaccattca     1980
tttttatctg gttgttctca agttcggtta cgagatccat ttgtctatct agttcaactt     2040
ggaaaatcaa cgtatcagtc gggcggcctc gcttatcaac caccaatttc atattgctgt     2100
aagtgtttaa atctttactt attggtttca aaacccattg gttaagcctt ttaaactcat     2160
ggtagttatt ttcaagcatt aacatgaact aaaattcatc aaggctaatc tctatatttg     2220
ccttgtgagt tttcttttgt gttagttctt ttaataacca ctcataaatc ctcatagagt     2280
atttgttttc aaaagactta acatgttcca gattatattt tatgaatttt tttaactgga     2340
aaagataagg caatatctct tcactaaaaa ctaattctaa ttttttcgctt gagaacttgg     2400 catagttttgt ccactggaaa atctcaaagc ctttaaccaa aggattcctg atttccacag     2460
ttctcgtcat cagctctctg gttgctttag ctaatacacc ataagcattt tccctactga     2520
tgttcatcat ctgagcgtat tggttataag tgaacgatac cgtccgttct ttccttgtag     2580
ggttttcaat cgtgggggttg agtagtgcca cacagcataa aattagcttg gtttcatgct     2640
```

-continued

```
ccgttaagtc atagcgacta atcgctagtt catttgcttt gaaaacaact aattcagaca    2700
tacatctcaa ttggtctagg tgattttaat cactatacca attgagatgg gctagtcaat    2760
gataattact agtccttttc ccgggtgatc tgggtatctg taaattctgc tagacctttg    2820
ctggaaaact tgtaaattct gctagaccct ctgtaaattc cgctagacct ttgtgtgttt    2880
tttttgttta tattcaagtg gttataattt atagaataaa gaaagaataa aaaaagataa    2940
aaagaataga tcccagccct gtgtataact cactacttta gtcagttccg cagtattaca    3000
aaaggatgtc gcaaacgctg tttgctcctc tacaaaacag accttaaaac cctaaaggct    3060
taagtagcac cctcgcaagc tcgggcaaat cgctgaatat tccttttgtc tccgaccatc    3120
aggcacctga gtcgctgtct ttttcgtgac attcagttcg ctgcgctcac ggctctggca    3180
gtgaatgggg gtaaatggca ctacaggcgc cttttatgga ttcatgcaag gaaactaccc    3240
ataatacaag aaaagcccgt cacgggcttc tcagggcgtt ttatggcggg tctgctatgt    3300
ggtgctatct gacttttttgc tgttcagcag ttcctgccct ctgattttcc agtctgacca    3360
cttcggatta tcccgtgaca ggtcattcag actggctaat gcacccagta aggcagcggt    3420
atcatcaaca ggcttacccg tcttactgtc cctagtgctt ggattctcac caataaaaaa    3480
cgcccggcgg caaccgagcg ttctgaacaa atccagatgg agttctgagg tcattactgg    3540
atctatcaac aggagtccaa gcgagctcga tatcaaatta cgccccgccc tgccactcat    3600
cgcagtactg ttgtaattca ttaagcattc tgccgacatg gaagccatca caaacggcat    3660
gatgaacctg aatcgccagc ggcatcagca ccttgtcgcc ttgcgtataa tatttgccca    3720
tggtgaaaac gggggcgaag aagttgtcca tattggccac gtttaaatca aaactggtga    3780
aactcaccca gggattggct gagacgaaaa acatattctc aataaaccct ttagggaaat    3840
aggccaggtt ttcaccgtaa cacgccacat cttgcgaata tatgtgtaga aactgccgga    3900
aatcgtcgtg gtattcactc cagagcgatg aaaacgtttc agtttgctca tggaaaacgg    3960
tgtaacaagg gtgaacacta tcccatatca ccagctcacc gtctttcatt gccatacgaa    4020
attccggatg agcattcatc aggcgggcaa gaatgtgaat aaaggccgga taaaacttgt    4080
gcttattttt ctttacggtc tttaaaaagg ccgtaatatc cagctgaacg gtctggttat    4140
aggtacattg agcaactgac tgaaatgcct caaaatgttc tttacgatgc cattgggata    4200
tatcaacggt ggtatatcca gtgatttttt tctccatttt agcttcctta gctcctgaaa    4260
atctcgataa ctcaaaaaat acgcccggta gtgatcttat ttcattatgg tgaaagttgg    4320
aacctcttac gtgccgatca acgtctcatt ttcgccagat atc    4363
```

<210> SEQ ID NO 11
<211> LENGTH: 5590
<212> TYPE: DNA
<213> ORGANISM: Artificial Sequence
<220> FEATURE:
<223> OTHER INFORMATION: Synthetic plasmid

<400> SEQUENCE: 11

```
gacgtcttga cagctagctc agtcctaggg attgtgctag caggtttaat cgaattgacg     60
tctttacggc tagctcagtc ctaggtacta tgctagcagg tttaatcgaa ttcaaaagat    120
cttttaagaa ggagatatac atatgattac tcatggttgt tatacccgga cccggcacaa    180
gcataagcta aaaaaaacat tgattatgct tagtgctggt ttaggattgt ttttttatgt    240
taatcagaac tcatttgcaa atggtgaaaa ttattttaaa ttgggttcgg attcaaaact    300
gttaactcat gatagctatc agaatcgcct ttttttatacg ttgaaaactg gtgaaactgt    360
```

```
tgccgatctt tctaaatcgc aagatattaa tttatcgacg atttggtcgt tgaataagca      420
tttatacagt tctgaaagcg aaatgatgaa ggccgcgcct ggtcagcaga tcattttgcc      480
actcaaaaaa cttcccttg aatacagtgc actaccactt ttaggttcgg cacctcttgt      540
tgctgcgggt ggtgttgctg tcacacgaa taaactgact aaaatgtccc cggacgtgac      600
caaaagcaac atgaccgatg acaaggcatt aaattatgcg gcacaacagg cggcgagtct      660
cggtagccag cttcagtcgc gatctctgaa cggcgattac gcgaaagata ccgctcttgg      720
tatcgctggt aaccaggctt cgtcacagtt gcaggcctgg ttacaacatt atggaacggc      780
agaggttaat ctgcaaagtg gtaataactt tgacggtagt tcactggact tcttattacc      840
gttctatgat tccgaaaaaa tgctggcatt tggtcaggtc ggagcgcgtt acattgactc      900
ccgctttacg gcaaatttag gtgcgggtca gcgtttttc cttcctgcaa acatgttggg      960
ctataacgtc ttcattgatc aggatttttc tggtgataat acccgtttag gtattggtgg     1020
cgaatactgg cgagactatt tcaaaagtag cgttaacggc tatttccgca tgagcggctg     1080
gcatgagtca tacaataaga aagactatga tgagcgccca gcaaatggct tcgatatccg     1140
ttttaatggc tatctaccgt catatccggc attaggcgcc aagctgatat atgagcagta     1200
ttatggtgat aatgttgctt tgtttaattc tgataagctg caatcgaatc ctggtgcggc     1260
gaccgttggg gtaaactata ctccgattcc tctggtgacg atggggatcg attaccgtca     1320
tggtacgggt aatgaaaatg atctccttta ctcaatgcag ttccgttatc agtttgataa     1380
atcgtggtct cagcaaattg aaccacagta tgttaacgag ttaagaacat tatcaggcag     1440
ccgttacgat ctggttcagc gtaataacaa tattattctg gagtacaaga agcaggatat     1500
tctttctctg aatattccgc atgatattaa tggtactgaa cacagtacgc agaagattca     1560
gttgatcgtt aagagcaaat acggtctgga tcgtatcgtc tgggatgata gtgcattacg     1620
cagtcagggc ggtcagattc agcatagcgg aagccaaagc gcacaagact accaggctat     1680
tttgcctgct tatgtgcaag gtggcagcaa tatttataaa gtgacggctc gcgcctatga     1740
ccgtaatggc aatagctcta acaatgtaca gcttactatt accgttctgt cgaatggtca     1800
agttgtcgac caggttgggg taacggactt tacggcggat aagacttcgg ctaaagcgga     1860
taacgccgat accattactt ataccgcgac ggtgaaaaag aatggggtag ctcaggctaa     1920
tgtccctgtt tcatttaata ttgtttcagg aactgcaact cttggggcaa atagtgccaa     1980
aacggatgct aacggtaagg caaccgtaac gttgaagtcg agtacgccag gacaggtcgt     2040
cgtgtctgct aaaaccgcgg agatgacttc agcacttaat gccagtgcgg ttatattttt     2100
tgatggtgcg cccgggaagc ttgtcgacgg agctcgataa tccggcaaaa aagggcaagg     2160
tgtcaccacc ctgccctttt tctttaaaac cgaaaagatt acttcgcgtt atgcaggctt     2220
cctcgctcac tgactcgctg cgctcggtcg ttcggctgcg gcgagcggta tcagctcact     2280
caaaggcggt aatctcgagt cgatccaaac tcgagtaagg atctccaggc atcaaataaa     2340
acgaaaggct cagtcgaaag actgggcctt tcgtttatc tgttgtttgt cggtgaacgc     2400
tctctactag agtcacactg gctcaccttc gggtgggcct ttctgcgttt atacctaggg     2460
tacgggtttt gctgcccgca aacgggctgt tctggtgttg ctagtttgtt atcagaatcg     2520
cagatccggc ttcagccggt ttgccggctg aaagcgctat ttcttccaga attgccatga     2580
ttttttcccc acgggaggcg tcactggctc ccgtgttgtc ggcagctttg attccgataag     2640 cagcatcgcc tgtttcaggc tgtctatgtg tgactgttga ctgtaacaa gttgtctcag     2700
```

-continued

```
gtgttcaatt tcatgttcta gttgctttgt tttactggtt tcacctgttc tattaggtgt   2760
tacatgctgt tcatctgtta cattgtcgat ctgttcatgg tgaacagctt tgaatgcacc   2820
aaaaactcgt aaaagctctg atgtatctat cttttttaca ccgttttcat ctgtgcatat   2880
ggacagtttt ccctttgata tgtaacggtg aacagttgtt ctacttttgt ttgttagtct   2940
tgatgcttca ctgatagata caagagccat aagaacctca gatccttccg tatttagcca   3000
gtatgttctc tagtgtggtt cgttgttttt gcgtgagcca tgagaacgaa ccattgagat   3060
catacttact ttgcatgtca ctcaaaaatt ttgcctcaaa actggtgagc tgaatttttg   3120
cagttaaagc atcgtgtagt gttttttctta gtccgttatg taggtaggaa tctgatgtaa   3180
tggttgttgg tattttgtca ccattcattt ttatctggtt gttctcaagt tcggttacga   3240
gatccatttg tctatctagt tcaacttgga aaatcaacgt atcagtcggg cggcctcgct   3300
tatcaaccac caatttcata ttgctgtaag tgtttaaatc tttacttatt ggtttcaaaa   3360
cccattggtt aagcctttta aactcatggt agttattttc aagcattaac atgaacttaa   3420
attcatcaag gctaatctct atatttgcct tgtgagtttt cttttgtgtt agttctttta   3480
ataaccactc ataaatcctc atagagtatt tgttttcaaa agacttaaca tgttccagat   3540
tatattttat gaattttttt aactggaaaa gataaggcaa tatctcttca ctaaaaacta   3600
attctaattt ttcgcttgag aacttggcat agtttgtcca ctggaaaatc tcaaagcctt   3660
taaccaaagg attcctgatt tccacagttc tcgtcatcag ctctctggtt gctttagcta   3720
atacaccata agcattttcc ctactgatgt tcatcatctg agcgtattgg ttataagtga   3780
acgataccgt ccgttctttc cttgtagggt tttcaatcgt ggggttgagt agtgccacac   3840
agcataaaat tagcttggtt tcatgctccg ttaagtcata gcgactaatc gctagttcat   3900
ttgctttgaa aacaactaat tcagacatac atctcaattg gtctaggtga ttttaatcac   3960
tataccaatt gagatgggct agtcaatgat aattactagt ccttttcccg ggtgatctgg   4020
gtatctgtaa attctgctag acctttgctg gaaaacttgt aaattctgct agaccctctg   4080
taaattccgc tagacctttg tgtgttttttt ttgtttatat tcaagtggtt ataatttata   4140
gaataaagaa agaataaaaa aagataaaaa gaatagatcc cagccctgtg tataactcac   4200
tactttagtc agttccgcag tattacaaaa ggatgtcgca aacgctgttt gctcctctac   4260
aaaacagacc ttaaaaccct aaaggcttaa gtagcaccct cgcaagctcg ggcaaatcgc   4320
tgaatattcc ttttgtctcc gaccatcagg cacctgagtc gctgtctttt tcgtgacatt   4380
cagttcgctg cgctcacggc tctggcagtg aatggggggta aatggcacta caggcgcctt   4440
ttatggattc atgcaaggaa actacccata atacaagaaa agcccgtcac gggcttctca   4500
gggcgtttta tggcgggtct gctatgtggt gctatctgac tttttgctgt tcagcagttc   4560
ctgccctctg attttccagt ctgaccactt cggattatcc cgtgacaggt cattcagact   4620
ggctaatgca cccagtaagg cagcggtatc atcaacaggc ttacccgtct tactgtccct   4680
agtgcttgga ttctcaccaa taaaaaacgc ccggcggcaa ccgagcgttc tgaacaaatc   4740
cagatggagt tctgaggtca ttactggatc tatcaacagg agtccaagcg agctcgatat   4800
caaattacgc cccgccctgc cactcatcgc agtactgttg taattcatta agcattctgc   4860
cgacatggaa gccatcacaa acggcatgat gaacctgaat cgccagcggc atcagcacct   4920
tgtcgccttg cgtataatat ttgcccatgg tgaaacgggg ggcgaagaag ttgtccatat   4980
tggccacgtt taaatcaaaa ctggtgaaac tcacccaggg attggctgag acgaaaaaca   5040
tattctcaat aaacccttta gggaaatagg ccaggttttc accgtaacac gccacatctt   5100
```

-continued

```
gcgaatatat gtgtagaaac tgccggaaat cgtcgtggta ttcactccag agcgatgaaa   5160
acgtttcagt ttgctcatgg aaaacggtgt aacaagggtg aacactatcc catatcacca   5220
gctcaccgtc tttcattgcc atacgaaatt ccggatgagc attcatcagg cgggcaagaa   5280
tgtgaataaa ggccggataa aacttgtgct tatttttctt tacggtcttt aaaaaggccg   5340
taatatccag ctgaacggtc tggttatagg tacattgagc aactgactga aatgcctcaa   5400
aatgttcttt acgatgccat tgggatatat caacggtggt atatccagtg attttttttct   5460 ccattttagc ttccttagct cctgaaaatc tcgataactc aaaaaatacg cccggtagtg   5520
atcttatttc attatggtga aagttggaac ctcttacgtg ccgatcaacg tctcattttc   5580
gccagatatc                                                          5590
```